(12) United States Patent
Karaolis

(10) Patent No.: US 7,592,326 B2
(45) Date of Patent: *Sep. 22, 2009

(54) METHOD FOR STIMULATING THE IMMUNE, INFLAMMATORY OR NEUROPROTECTIVE RESPONSE

(76) Inventor: David K. R. Karaolis, 4 Club Rd., Baltimore, MD (US) 21210-2227

( * ) Notice: Subject to any disclaimer, the term of this patent is extended or adjusted under 35 U.S.C. 154(b) by 354 days.

This patent is subject to a terminal disclaimer.

(21) Appl. No.: 11/669,006

(22) Filed: Jan. 30, 2007

(65) Prior Publication Data
US 2007/0281897 A1 Dec. 6, 2007

Related U.S. Application Data

(63) Continuation-in-part of application No. 11/079,886, filed on Mar. 15, 2005.

(60) Provisional application No. 60/552,721, filed on Mar. 15, 2004, provisional application No. 60/563,692, filed on Apr. 20, 2004.

(51) Int. Cl.
*A01N 43/04* (2006.01)
*A61K 31/70* (2006.01)

(52) U.S. Cl. .............................. 514/47; 514/45; 514/46; 514/48

(58) Field of Classification Search ...................... None
See application file for complete search history.

(56) References Cited

FOREIGN PATENT DOCUMENTS

WO 2005030182 A2 4/2005

OTHER PUBLICATIONS

Klinman Nature Reviews: Immunology (Apr. 2004), vol. 4, pp. 1-10.*
Tischler et al., Cyclic diguanylate (c-di-GMP) regulates *Vibrio cholerae* biofilm formation, Molecular Microbiology, 53 (3)857-869 (2004).

* cited by examiner

*Primary Examiner*—Patrick T Lewis
(74) *Attorney, Agent, or Firm*—Browdy and Neimark, P.L.L.C.

(57) ABSTRACT

Cycic di-GMP, or a cyclic dinucleotide analogue thereof that has the same effect as cyclic di-GMP, stimulates or enhances immune or inflammatory response in a patient or enhances the immune response to a vaccine by serving as an adjuvant. Cyclic di-GMP, or a cyclic dinucleotide analogue thereof, also has neuroprotective properties for use as a neuroprotective agent to inhibit, treat, or ameliorate the effects of injuries, diseases,

29 Claims, 13 Drawing Sheets

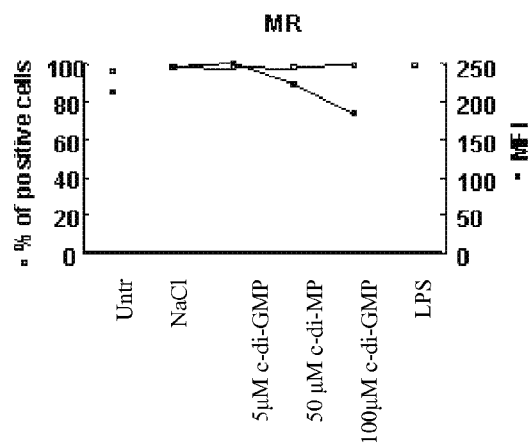
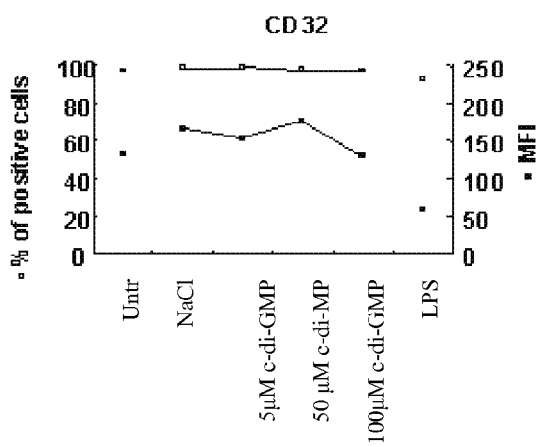
FIG. 1G    FIG. 1H
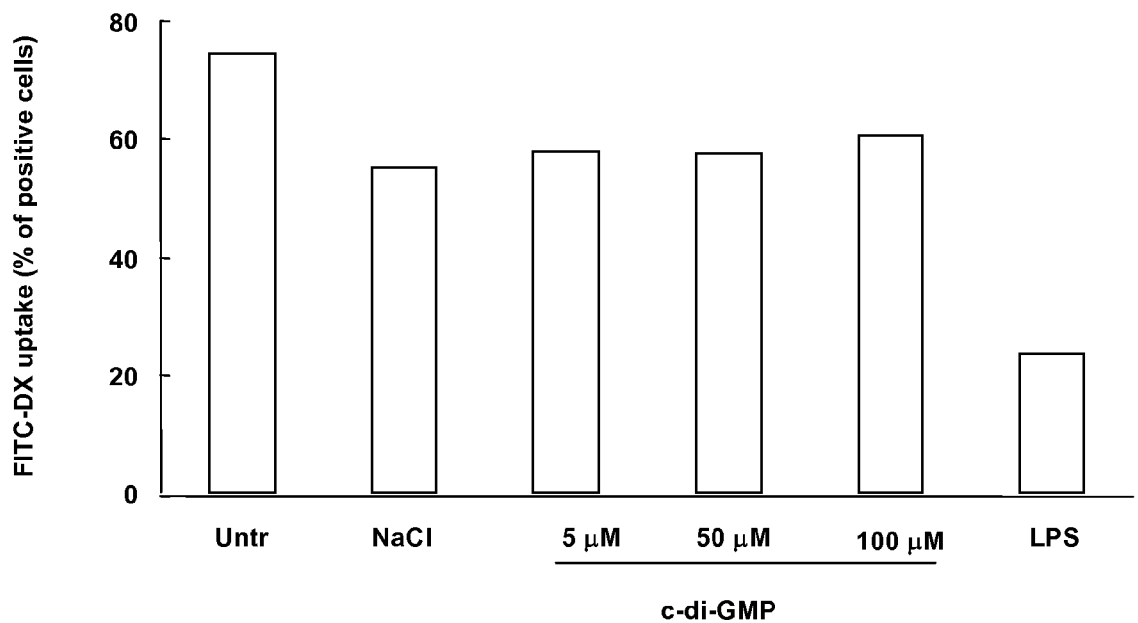
FIG. 2 a, data statistically compared to control group
b, data statistically compared to STS-treated group
*, p < 0.05 and **, p < 0.01 according to ANOVA

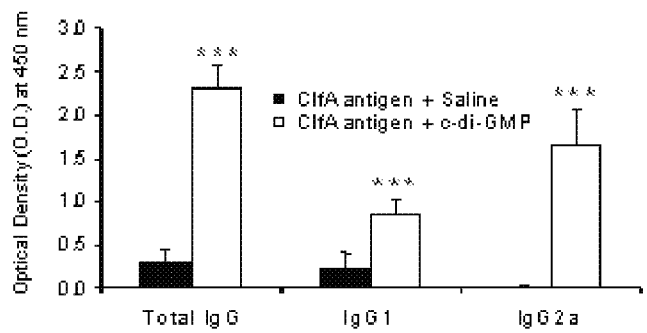
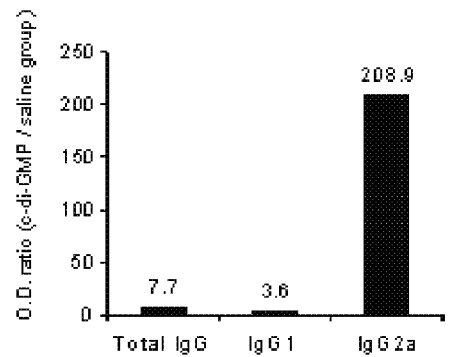
Fig. 7A                Fig. 7B
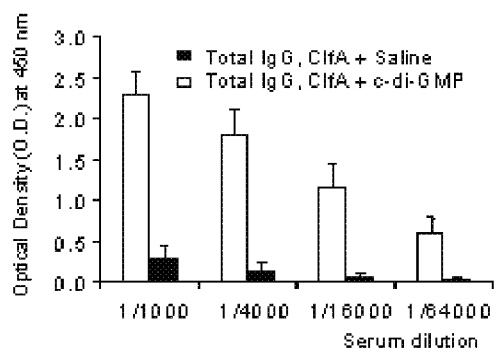
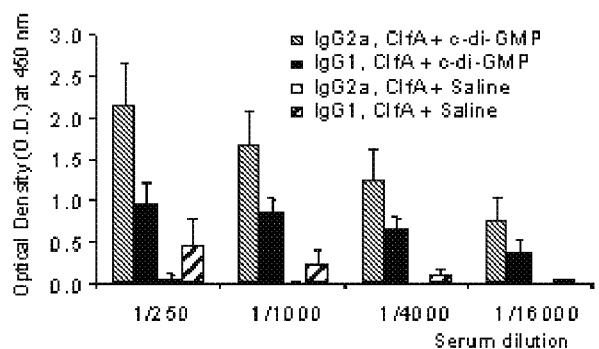
Fig. 7C                Fig. 7D
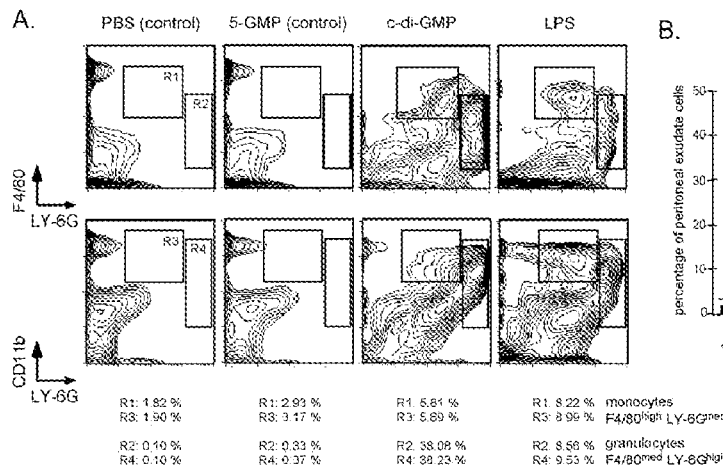
Fig. 8A                Fig. 8B

```
                     SEQUENCE LISTING

<160> NUMBER OF SEQ ID NOS: 15

<210> SEQ ID NO 1
<211> LENGTH: 21
<212> TYPE: DNA
<213> ORGANISM: Artificial
<220> FEATURE:
<223> OTHER INFORMATION: synthetic

<400> SEQUENCE: 1
ccagtgagaa tgagggccat a                                              21

<210> SEQ ID NO 2
<211> LENGTH: 19
<212> TYPE: DNA
<213> ORGANISM: Artificial
<220> FEATURE:
<223> OTHER INFORMATION: synthetic

<400> SEQUENCE: 2
ctcaacacgt gggcaggat                                                 19

<210> SEQ ID NO 3
<211> LENGTH: 21
<212> TYPE: DNA
<213> ORGANISM: Artificial
<220> FEATURE:
<223> OTHER INFORMATION: synthetic

<400> SEQUENCE: 3
tttgggcatc atcttcctgg a                                              21
```

```
<210> SEQ ID NO 4
<211> LENGTH: 20
<212> TYPE: DNA
<213> ORGANISM: Artificial
<220> FEATURE:
<223> OTHER INFORMATION: synthetic

<400> SEQUENCE: 4
cagccgatgg gttgtacctt                                               20

<210> SEQ ID NO 5
<211> LENGTH: 21
<212> TYPE: DNA
<213> ORGANISM: Artificial
<220> FEATURE:
<223> OTHER INFORMATION: synthetic

<400> SEQUENCE: 5
tgtgggtgag gagcacgtag t                                             21

<210> SEQ ID NO 6
<211> LENGTH: 27
<212> TYPE: DNA
<213> ORGANISM: Artificial
<220> FEATURE:
<223> OTHER INFORMATION: synthetic

<400> SEQUENCE: 6
tcccaggttc tcttcaaggg acaaggc                                       27

<210> SEQ ID NO 7
<211> LENGTH: 23
<212> TYPE: DNA
<213> ORGANISM: Artificial
<220> FEATURE:
<223> OTHER INFORMATION: synthetic

<400> SEQUENCE: 7
gaacatccag agcttgagtg tga                                           23

<210> SEQ ID NO 8
<211> LENGTH: 25
<212> TYPE: DNA
<213> ORGANISM: Artificial
<220> FEATURE:
<223> OTHER INFORMATION: synthetic

<400> SEQUENCE: 8
ccttgagagt ggctatgact tctgt                                         25

<210> SEQ ID NO 9
<211> LENGTH: 19
<212> TYPE: DNA
<213> ORGANISM: Artificial
<220> FEATURE:
<223> OTHER INFORMATION: synthetic

<400> SEQUENCE: 9
cccccaggac cccactgcg                                                19

<210> SEQ ID NO 10
<211> LENGTH: 20
<212> TYPE: DNA
<213> ORGANISM: Artificial
<220> FEATURE:
<223> OTHER INFORMATION: synthetic
```

```
<400> SEQUENCE: 10
agaccctgcc cattgaactg                                           20

<210> SEQ ID NO 11
<211> LENGTH: 26
<212> TYPE: DNA
<213> ORGANISM: Artificial
<220> FEATURE:
<223> OTHER INFORMATION: synthetic

<400> SEQUENCE: 11
gaagctggtg ctgtagttct catatt                                    26

<210> SEQ ID NO 12
<211> LENGTH: 22
<212> TYPE: DNA
<213> ORGANISM: Artificial
<220> FEATURE:
<223> OTHER INFORMATION: synthetic

<400> SEQUENCE: 12
cgttggaagc acggcagcag aa                                        22

<210> SEQ ID NO 13
<211> LENGTH: 22
<212> TYPE: DNA
<213> ORGANISM: Artificial
<220> FEATURE:
<223> OTHER INFORMATION: synthetic

<400> SEQUENCE: 13
ccgtgaaaag atgacccaga tc                                        22

<210> SEQ ID NO 14
<211> LENGTH: 20
<212> TYPE: DNA
<213> ORGANISM: Artificial
<220> FEATURE:
<223> OTHER INFORMATION: synthetic

<400> SEQUENCE: 14
cacagcctgg atggctacgt                                           20

<210> SEQ ID NO 15
<211> LENGTH: 25
<212> TYPE: DNA
<213> ORGANISM: Artificial
<220> FEATURE:
<223> OTHER INFORMATION: synthetic

<400> SEQUENCE: 15
tttgagacct tcaacacccc agcca                                     25
```

METHOD FOR STIMULATING THE IMMUNE, INFLAMMATORY OR NEUROPROTECTIVE RESPONSE

CROSS-REFERENCE TO RELATED APPLICATIONS

This application is a continuation-in-part of U.S. application Ser. No. 11/079,886, filed Mar. 15, 2005, which claims the benefit of priority under 35 U.S.C. §119(e) from U.S. provisional application Nos. 60/552,721, filed Mar. 15, 2004, and 60/563,692, filed Apr. 20, 2004, the entire contents of which are hereby incorporated by reference.

BACKGROUND OF THE INVENTION

1. Field of the Invention

The present invention relates to immunomodulation and to the stimulation and enhancement of the immune or inflammatory response, including the use of adjuvants to enhance immune response to a vaccine. The present invention also relates to treatment of injuries, diseases, disorders and conditions that result in neurodegeneration.

2. Description of the Related Art

Millions worldwide are affected with infectious diseases, cancer, lymphomas, HIV, AIDS, rheumatoid arthritis, asthma, immunodeficiency disorders and diseases involving defective immune, allergic, or inflammatory responses. Many diseases and their disease outcomes involve immune or inflammatory responses and are associated with the stimulation of dendritic cells (DCs), T cells, the production or suppression of various cytokines, chemokines and interferons, and the increase or decrease in the availability of cytokines and chemokine receptors. In addition, many neurological and neurodegenerative diseases involve damage to nerve or neuronal cells.

Dendritic Cells

Dendritic cells (DCs) are the most potent antigen-presenting cells and they play a crucial role in the generation and regulation of immunity (Banchereau and Steinman, 1998; Sallusto and Lanzavecchia, 1994). Their priming ability is acquired upon maturation and is characterized by the activation of transcription factors, antigen processing, control of migration and regulation of inflammatory responses (Shutt et al., 2000; Granucci et al., 2001; Sallusto et al., 1999; Ouaaz et al., 2002). Regulated migration of DCs is central to the induction of physiological immune responses. The expression of surface molecules on DCs known to be critical for antigen-presenting function include HLA-DR, CD40, CD83, CXCR4 and CD80 and CD86 and this is associated with increased cytokine and chemokine production and stimulatory capacity.

DCs link innate and adaptive immunity by sensing pathogens or vaccinogens and signaling a variety of defense responses. DCs comprise a family of cells specializing in antigen capture and presentation to T cells, play a role in bacterial uptake across mucosal surfaces, can open tight junctions and sample antigens directly across epithelia (Rimoldi et al., 2004). DCs sample enteric antigens in the lamina propria and Peyer's patches, and transport them to mesenteric nodes where they are presented to lymphocytes (Macpherson et al., 2004). DCs are potent antigen-presenting cell that are able to initiate and modulate immune responses and are hence often exploited as cellular vaccine components for applications such as immunotherapy. Their ability to migrate from peripheral tissues to the T cell areas of draining lymph nodes is crucial for the priming of T lymphocytes. Signal molecules that promote DCs to acquire potent Th-1 cell stimulatory activity and substantial chemotactic responsiveness to chemokines would be useful in the development of vaccines and for tumor immunotherapy (Scandella et al., 2002).

DCs are the first target of HIV and, by clustering and activating T cells, may both activate antiviral immunity and facilitate virus dissemination (Sewell and Price, 2001; Frank and Pope, 2002). During HIV infection, there is loss of immune control and dysfunction of DCs may contribute to immune suppression associated with AIDS progression (Quaranta et al., 2004). Activation of immature DCs by manipulating their phenotypical, morphological and functional developmental program would have useful clinical applications for therapeutic intervention for AIDS patients.

Cytokines and Costimulatory Molecules

Cytokines are proteins that regulate immune and inflammatory reactions. Cytokines play an essential role in the activation and maintenance of both innate and acquired immune responses. Cytokines and chemokines have been used as vaccine adjuvants with both traditional and DNA vaccines. Cytokines are small proteins (~25 kDa) that are released by various cells in the body, usually in response to an activating stimulus, and induce responses through binding to specific receptors. They can act in an autocrine manner, affecting the behavior of the cell that releases the cytokine, or in a paracrine manner, affecting the behavior of adjacent cells. Some cytokines can act in an endocrine manner, affecting the behavior of distant cells, although this depends on their ability to enter the circulation and on their half-life.

Interleukin-12 (IL-12) is a potent enhancer of cellular responses. IL-12 is a potent proinflammatory cytokine with potent antitumor effects that enhances cytotoxic T lymphocytes (CTL) and natural killer (NK) cell activity. IL-12 treatment of mice augments antibody responses to T independent polysaccharide antigen (Buchanan et al., 1998). IL-12 and IL-1 have been shown to induce systemic immunity to mucosally administered vaccines (Boyaka and McGhee, 2001). Studies have shown the regression of established neuroblastoma in mice vaccinated with IL-12 transduced dendritic cells (Redlinger et al., 2003). Another study with syngeneic A/J mice using intratumorally injected IL-12 transduced cells showed that mice underwent tumor regression indicating that increased IL-12 production by DCs induces a significant antitumor response in a poorly immunogenic murine model of neuroblastoma (Shimizu et al., 2001). These results clearly show the vital role of DCs in the immunobiology of neuroblastoma, and that protection of these cells from tumour induced apoptosis is a critical aspect for immunotherapies treating aggressive tumors. Co-expression of cytokines, chemokines and costimulatory molecules enhances the immunogenicity of DNA vaccines.

As is true for most intracellular pathogens, immunization with live *Chlamydia trachomatis* induces a stronger protective immunity than immunization with inactivated organism and is associated with high levels of the proinflammatory cytokine IL-12 and the enrichment of DCs among mice immunized with viable organisms (Zhang, et al., 1999). These results indicate that the induction of proinflammatory cytokines and activation and differentiation of DCs is important for inducing active immunity to *C. trachomatis* infection.

Chemokines are a class of cytokines that have chemoattractant properties, inducing cells with the appropriate receptors to migrate toward the source of the chemokine. Certain chemokines may recruit cells to sites of infection. Chemokines such as RANTES may promote the infiltration into tissues of a range of leukocytes including effector T cells. Effector T cells that recognize pathogen antigens in the tissues produce cytokines such as TNF-α, which activates endothelial cells to express E-selectin, VCAM-1, and ICAM-1, and chemokines such as RANTES, which can then act on effector T cells to activate their adhesion molecules.

Chemokines exert their effects through at least nineteen G protein-coupled receptors (GPCRs). The nomenclature of the chemokine receptors follows the notation used for the chemokine subfamilies and they are termed CCR1-10 (CC chemokine receptor 1-10), CXCR1-6, XCR1 and CX3CR1. A remarkable feature of the chemokine receptors is their relative lack of selectivity in ligand binding, with many chemokine receptors binding more than one chemokine with high affinity. For example, eleven chemokines are reported to bind to the CCR1 receptor, including MIP-1α (macrophage inflammatory protein 1α), MIP-1β, MIP-1δ, RANTES (regulated on activation normal T cell expressed and secreted), MCP-1 (monocyte chemotactic peptide 1), MCP-2, MCP-3, MCP-4, Lkn-1 (leukotactin-1), MPIF-1 (myeloid progenitor inhibitory factor 1) and HCC-1 (hemofiltrate CC chemokine 1), with varying affinities and acting with different degrees of agonism. Similarly, individual chemokines act as ligands for different receptors. For example, MCP-3 acts as a ligand for CCR1, CCR2, CCR3 and CCR5. This promiscuity and the apparent redundancy of signaling that may arise poses many questions as to the control of chemokine signaling in different tissues expressing different combinations of chemokines, receptors and effectors (*ACTA BIOCHIMICA et BIOPHYSICA SINICA* 2003, 35(9):779-788).

There are different variants of HIV, and the cell types that they infect are determined to a large degree by which chemokine receptor they bind as co-receptor. The variants of HIV that are associated with primary infections use CCR5, which binds the CC chemokines RANTES, MIP-1α, and MIP-1β, as a co-receptor, and require only a low level of CD4 on the cells they infect. These variants of HIV infect dendritic cells, macrophages, and T cells in vivo.

Despite the apparent complexities of the chemokine signaling systems, the importance of individual chemokine receptors is gradually emerging from detailed studies on knockout mice, targeted gene disruption and the application of specific chemokine antagonists. As an example, CCR1 knockout mice have been reported to have disordered trafficking and proliferation of myeloid progenitor cells and to display impaired inflammatory responses to a variety of stimuli. Control of the CCR1 signaling system was demonstrated to have clinical significance as CCR1 knockout mice display significantly reduced rejection responses to cardiac allografts. This suggests that a strategy of blocking CCR1 signaling pathways may be useful in preventing rejection of transplanted tissues (*ACTA BIOCHIMICA et BIOPHYSICA SINICA* 2003, 35(9) :779-788).

CCR5 has generated widespread interest because of its role as a co-receptor for HIV. The identification of a naturally occurring mutant of this receptor, CCR5Δ32, and observations that homo and heterozygotes for this mutant have increased resistance to HIV infection and the development of AIDS has highlighted the potential benefits to human health that could accrue from controlling the ability of CCR5 to bind ligands (*ACTA BIOCHIMICA et BIOPHYSICA SINICA* 2003, 35(9):779-788).

Immunotherapy

Costimulatory molecules are important regulators of T cell activation and thus are the favored targets for therapeutic manipulation of the immune response. One of the key costimulatory receptors is CD80, which binds T cell ligands, CD28, and CTLA-4. It has been shown that expression of the costimulatory molecules CD80, CD86 and CD83 plays an important role in adjuvant activity and it is known that expression of CD86 is a feature of CT-based adjuvants (Lyke, 2004). Thus, molecules or compounds that affect CD80 expression represent promising novel therapeutic and immunotherapy agents that might induce protective immunity. A number of immunomodulatory therapies are being developed for clinical applications. These include approaches targeting antigen presentation and costimulation, T cell activation, action of proinflammatory mediators and modulating the cytokine balance (Asadullah et al., 2002). Tumor necrosis factors (TNFs) are known to be cytotoxic cytokines produced by macrophages and lymphocytes and are found to be suppressed in cancer patients or those who are pregnant.

Immunotherapy for Cancer

Immunosuppression is a hallmark of advanced malignancies in man (Lentz, 1999). Immunotherapy is the name given to cancer treatments that use the immune system to attack cancers. That is, the immune system can be stimulated to slow down the growth and spread of cancer. Immunotherapies involving certain cytokines and antibodies have now become part of standard cancer treatment. Immunotherapy of cancer began approximately 100 years ago when Dr. William Coley showed that cancer could be controlled by injections of bacterial products and components known as Coley's toxin. It is now known that the active anti-cancer component of Coley's toxin are bacterial oligonucleotides.

Systemic immunotherapy refers to immunotherapy that is used to treat the whole body and is more commonly used than local immunotherapy which is used to treat one "localized" part of the body, particularly when a cancer has spread. The suppressive milieu present within established tumors inhibits effective immune responses and new strategies are emerging to manipulate the local tumor environment to promote a proinflammatory environment, promote dendritic cell activation, and enhance antitumor immunity (Kaufman and Disis, 2004).

Immunotherapy is a potential useful strategy for the treatment of brain tumors because it offers a degree of specificity, the ability to extravasate into solid tumors, and the potential for eliciting a long-term protective immune response. Several approaches have been developed including the use of cytokines. In studies on the treatment of brain tumors, T cell stimulation with the proinflammatory cytokine IL-12 can elicit antitumor immunity (Gawlick et al., 2004). As such, cytokine treatments combined with tumor-targeted costimulation, or methods that stimulate cytokine production and the proinflammatory response, may be a useful adjunct treatment for brain tumors.

Immunotherapy for Infectious Diseases

In order to combat the increasing prevalence of drug-resistant *Mycobacterium tuberculosis* infection, new drugs are being developed. One promising strategy is to treat patients with refractory mycobacteriosis using ordinary antimycobacterial drugs in combination with appropriate immunomodulators in order to mobilize the cytokine network in response to mycobacterial infection such as using immunomodulating cytokines (especially Th-1 and Th-1-like cytokines such as IL-12 and proinflammatory cytokines such as TNF-α (Tomioka 2004). The Th-1 response participates in cell-mediated immunity and is essential in controlling infections due to intracellular pathogens and viruses.

Although *Cryptococcus neoformans* is a fungal pathogen that causes human disease predominantly in the immunocompromised host, severe infection can occur in immunocompetent individuals. Activation of cellular immunity plays a key role in anticryptococcal defense, and therefore, immunotherapy to increase the immune and proinflammatory response would be a useful treatment to restore immunological parameters and sustained clinical recovery for refractory cryptococcal meningitis (Netea et al., 2004).

The bacterium *Bacillus anthracis* causes the disease anthrax, which if left untreated, can result in bactermia, multisystem dysfunction and death. Anthrax lethal toxin severely impairs the function of dendritic cells—which are pivotal to the establishment of immunity against pathogens—and host immune responses (Agrawal et al., 2003). Dendritic cells exposed to lethal toxin and then exposed to lipopolysaccharide do not upregulate costimulatory molecules, secrete greatly diminished amounts of proinflammatory cytokines, and do not effectively stimulate T cells (Agrawal et al., 2003). Methods to stimulate dendritic cells and the proinflammatory response might be a useful strategy to stimulate the immune response and in the immunotherapy of anthrax infection.

Host defenses against systemic mycoses is multifactorial, depending on innate, as well as acquired mechanisms in which innate resistance includes inflammatory responses whereby production of proinflammatory cytokines increase the capacity of host defenses for killing (Clemons and Stevens, 2001). Therefore, a strong Th-1 response can provide protective immunity suggesting that immunotherapy has utility as a basis in treating or inhibiting mycoses.

Studies on the intracellular activities occurring during *Salmonella* infection in DCs show that the bacteria suppress T cell proliferation (Cheminay et al., 2005). This suggests that immunotherapy might be a useful approach in the inhibition or treatment of infections caused by intracellular bacteria such as *Salmonella*.

Chemokines that bind to HIV co-receptors are potent and selective inhibitors of HIV infection and can be used in controlling HIV infection in concert with humoral and cellular immune and inflammatory responses (Garzino-Demo et al., 2000). This indicates that methods or molecules that promote the immunostimulation of chemokines can be used to inhibit or treat HIV infection.

*Klebsiella pneumoniae* is an encapsulated, highly virulent Gram-negative bacteria that is a leading cause of both community-acquired and nosocomial pneumonia. A frequent complication of pulmonary infection due to *K. pneumoniae* is the propensity of this organism to spread from the lung into the bloodstream, resulting in widespread systemic dissemination and death. Innate immunity is the principal pathway for elimination of virulent extracellular Gram-positive and Gram-negative pathogens, including *K. pneumoniae*, from the lung (Nelson et al., 1995). The two main phagocytic cells that constitute pulmonary innate immunity are resident alveolar macrophages (AM) and recruited neutrophils (PMN) (Lipscomb et al., 1983; and Towes et al., 1980). Both cell types are essential in host defense against bacterial pneumonia, such as that caused by *K. pneumoniae*, as the selective depletion of either cell population results in profound defects in the clearance of bacteria from the alveolar space (Broug-Holub et al., 1997; and Tsai et al., 2000). In addition, local and rapidly recruited lung DC internalize bacteria, which promotes DC maturation, expression of type 1 promoting cytokines (e.g., interleukin 12 (IL-12), type 1 interferons, and chemokines), co-stimulatory molecules, and migration to regional lymph nodes (Banchereau et al., 1998; Kikuchi et al., 2005; Kradin et al., 2000; Liu et al., 2006; and Mc William et al., 1994). Presentation of microbial antigens to naive T cells leads to the antigen-specific production of interferon-gamma (IFN-gamma) and the development of humoral immunity. Interferon-gamma can also be expressed early in infection in a non-antigen specific fashion by lung macrophages, NK cells, NKT cells, and γδ T cells, either directly in response to microbial signals or in a paracrine fashion in response to host-derived cytokines such as IL-12 (Deng et al., 2004; Ferlazzo et al., 2003; Johnston et al., 2003; and Moore et al., 2000). The type 1 cytokines IL-12, IFN-gamma, and IP-10 are required for host defense against both intracellular and extracellular bacterial pathogens (Brieland et al., 1998; Deng et al., 2001; Greenberger et al., 1996; Moore et al., 2002; Skerrett et al., 1994; Tateda et al., 1998 and 2001; Zeng et al., 2005; and Yoshida et al., 2001). Molecules that modulate (e.g., stimulate) the immune response might have clinical application in the inhibition (pretreatment) or therapy (treatment) of pneumonia.

Oligonucleotide Molecules as Anti-Cancer Agents

The use of unmethylated (CpG) oligonucleotides in the treatment or prevention of cancer has been reported. Synthetic oligonucleotides containing CpG with appropriate flanking regions (CpG motif) have been found to activate macrophages, dendritic cells and B cells to secrete a variety of immunomodulatory cytokines such as IL-6, IL-12, IL-18 and gamma interferon (Krieg, 2002). CpG DNA has also been shown to activate costimulatory molecules such as CD80 and CD86. CpG DNA induces strong innate immunity at mucosal surfaces. The immunostimulatory property of CpG DNA produces long-term vaccine-like effects due to its adjuvant properties. CpG oligonucleotides influence both antibody and cell-mediated immunity and applications include vaccine adjuvants, taming allergic reactions and potentiating monoclonal antibodies and cytotoxic immune cells. They also enhance the antitumor effects of chemotherapeutic agents and improve survival after surgical section of a solid tumor (Weigel et al., 2003). For CpG oligonucleotides, the antitumor effect is mediated via activation of the host immune system, not through direct anti-tumor effects. Data demonstrate that systemic application of proinflammatory reagents drastically enhances extravasation of effector cells into tumor tissue, an observation that is of general importance for immunotherapy of solid tumors in a clinical setting (Garbi et al., 2004). Based on their immunotherapeutic properties, CpG oligonucleotides have been used to treat and prevent various cancers and used in cancer vaccines. (U.S. Pat. Nos: 6,653,292; 6,429,199; 6,406,705; and 6,194,388).

Immunotherapy for Neurodegenerative Disease

The nervous system comprises the central and the peripheral nervous system. The central nervous system (CNS) is composed of the brain and spinal cord and the peripheral nervous system (PNS) consists of all of the other neural elements, namely the nerves and ganglia outside of the brain and spinal cord.

Damage to the nervous system may result from a traumatic injury, such as penetrating trauma or blunt trauma, or a disease or disorder, including but not limited to Alzheimer's disease, Parkinson's disease, Huntington's disease, amyotrophic lateral sclerosis (ALS), diabetic neuropathy, senile dementia, and ischemia.

Maintenance of central nervous system integrity is a complex "balancing act" in which compromises are struck with the immune system. In most tissues, the immune system plays an essential part in protection, repair, and healing. In the central nervous system, because of its unique immune privilege, immunological reactions are relatively limited (Streilein, 1993 and 1995). A growing body of evidence indicates that the failure of the mammalian central nervous system to achieve functional recovery after injury is a reflection of an ineffective dialog between the damaged tissue and the immune system. For example, the restricted communication between the central nervous system and blood-borne macrophages affects the capacity of axotomized axons to regrow; transplants of activated macrophages can promote central nervous system regrowth (Lazarov Spiegler et al, 1996; Rapalino et al, 1998).

Activated T cells have been shown to enter the central nervous system parenchyma, irrespective of their antigen specificity, but only T cells capable of reacting with a central nervous system antigen seem to persist there (Hickey et al, 1991; Werkele, 1993; Kramer et al, 1995). T cells reactive to antigens of central nervous system white matter, such as myelin basic protein (MBP), can induce the paralytic disease experimental autoimmune encephalomyelitis (EAE) within several days of their inoculation into naive recipient rats (Ben-Nun, 1981a). Anti-MBP T cells may also be involved in the human disease multiple sclerosis (Ota, K. et al, 1990; Martin, 1997). However, despite their pathogenic potential, anti-MBP T cell clones are present in the immune systems of healthy subjects (Burns, 1983; Pette, M. et al, 1990; Martin et al, 1990; Schluesener et al, 1985). Activated T cells, which normally patrol the intact central nervous system, transiently accumulate at sites of central nervous system white matter lesions (Hirschberg et al, 1998).

A catastrophic consequence of central nervous system injury is that the primary damage is often compounded by the gradual secondary loss of adjacent neurons that apparently were undamaged, or only marginally damaged, by the initial injury (Faden et al, 1992; Faden 1993; McIntosh, 1993). The primary lesion causes changes in extracellular ion concentrations, elevation of amounts of free radicals, release of neurotransmitters, depletion of growth factors, and local inflammation. These changes trigger a cascade of destructive events in the adjacent neurons that initially escaped the primary injury (Lynch et al, 1994; Bazan et al, 1995; Wu et al, 1994). This secondary damage is mediated by activation of voltage-dependent or agonist-gated channels, ion leaks, activation of calcium-dependent enzymes such as proteases, lipases and nucleases, mitochondrial dysfunction and energy depletion, culminating in neuronal cell death (Yoshina et al, 1991; Hovda et al, 1991; Zivin et al, 1991; Yoles et al, 1992). The widespread loss of neurons beyond the loss caused directly by the primary injury has been called "secondary degeneration."

One of the most common mediators which cause self-propagation of the diseases even when the primary risk factor is removed or attenuated is glutamate, an excitatory amino acid capable of displaying dual activity: playing a pivotal role in normal central nervous system (CNS) functioning as an essential neurotransmitter, but becoming toxic when its physiological levels are exceeded. Elevation of glutamate has been reported in many CNS disorders. In its role as an excitotoxic compound, glutamate is one of the most common mediators of toxicity in acute and chronic (including optic nerve degeneration in glaucoma) degenerative disorders (Pitt et al., 2000 and Schoepp et al., 1996). Endogenous glutamate has been attributed to the brain damage occurring acutely after status epilepticus, cerebral ischemia or traumatic brain injury. It may also contribute to chronic neurodegeneration in such disorders as amyotrophic lateral sclerosis and Huntington's chorea.

Intensive research has been devoted to attenuating the cytotoxic effect of glutamate by the use of locally acting drugs, such as NMDA-receptor antagonists (Brauner-Osborne et al., 2000). Conventional therapy of this type is often unsatisfactory, however, as in neutralizing the toxic effect it is likely to interfere with the physiological functioning. In humans, such compounds have psychotropic and other side effects that make them unsuitable as therapeutic agents. They also have the disadvantage of interfering with the essential physiological functioning of glutamate as a ubiquitous CNS neurotransmitter. Because glutamate activity is essential for normal physiological functioning, yet is potentially devastating after acute injury or in chronic CNS disorders, any attempt to neutralize its harmful effect must do so without eliminating its essential activity at other sites in the body.

Another tragic consequence of central nervous system injury is that neurons in the mammalian central nervous system do not undergo spontaneous regeneration following an injury. Thus, a central nervous system injury causes permanent impairment of motor and sensory functions.

Spinal cord lesions, regardless of the severity of the injury, initially result in a complete functional paralysis known as spinal shock. Some spontaneous recovery from spinal shock may be observed, starting a few days after the injury and tapering off within three to four weeks. The less severe the insult, the better the functional outcome. The extent of recovery is a function of the amount of undamaged tissue minus the loss due to secondary degeneration. Recovery from injury would be improved by neuroprotective treatment that could reduce secondary degeneration. For example, alleviation of the effect of glutamate is a frequent target of neuroprotective drug development. Among the drugs which are being developed for this purpose are N-methyl-D-aspartate (NMDA)-receptor or alpha-amino-3-hydroxy-5-methyl-4-isox-azoleproprionic acid (AMPA)-receptor antagonists. These drugs will inevitably have severe side effects as they interfere with the functioning of NMDA and AMPA receptors, which are crucial for CNS activity. One of the most intensely studied NMDA-receptor antagonists is MK801, which provides effective neuroprotection but with severe side effects. In animal models of cerebral ischemia and traumatic brain injury, NMDA and AMPA receptor antagonists protect against acute brain damage and delayed behavioral deficits. Such compounds are undergoing testing in humans, but therapeutic efficacy has yet to be established. Other clinical conditions that may respond to drugs acting on glutamatergic transmission include epilepsy, amnesia, anxiety, hyperalgesia and psychosis (Meldrum, 2000).

Glaucoma may be viewed as a neurodegenerative disease and consequently amenable to any therapeutic intervention applicable to neurodegenerative diseases. There is evidence that neuroprotection can be achieved both pharmacologically and immunologically where immunologic intervention boosts the body's repair mechanisms for counteracting the toxicity of physiologic compounds acting as stress signals and that boosting of a T cell-based mechanism promotes recovery of the damaged optic nerve. (Schwartz, 2003; Schwartz, 2004).

In rat cerebral cortical cultures, neuronal killing was partially or completely prevented by chemokines that stimulate the CXCR4, CCR3 or CCR5 chemokine receptors (Brenneman et al., 1999). Cytokines have been shown to be involved in nerve regeneration (Stoll et al., 2000).

Vaccines and Adjuvants

Vaccination is the single most valuable tool in the prevention of disease caused by infectious agents. Vaccination to protect against various infectious diseases may be enhanced by using adjuvants that can selectively stimulate immunoregulatory responses. Compared to injection of an antigen alone, injection of antigen plus an adjuvant generally permits use of a much smaller quantity of antigen and increases the antibody titer. Attenuated viruses and recombinant proteins are poorly immunogenic and absolutely require adjuvants for efficient immunostimulation, as do other antigens such as synthetic peptides, subunit vaccines, polysaccharides, killed cell preparations and plasmid DNA. For example, tetanus toxoid is not immunogenic in the absence of adjuvants. Some of these antigens require high production costs due to purification processes that are necessary to avoid contamination from cell products. The adjuvant may aid the immune response by forming a depot of antigen at the site of interest, it may serve as a vehicle to help deliver the antigen to the spleen or lymph nodes where antigen is trapped by follicular DCs, or it may activate the various cells involved in the immune response, either directly or indirectly. Many bacteria contain substances or products (e.g., endotoxin or cell wall constituents) that activate cells of the immune system. Safe and potent new adjuvants are needed for vaccines. These include vaccines that are administered at mucosal surfaces. The development of methods to enhance antigen presentation by DC is required for successful vaccines, particularly in immunocompromised patients. Activation of DCs is crucial for priming cytotoxic T lymphocytes (CTL), which have a critical role in tumor immunity, and it is considered that adjuvants are necessary for activation of DCs and for enhancement of cellular immunity. A Th-1 oriented immune response is important for an adequate cell mediated immune response and for protection induced by natural infection or vaccination with vaccines. Desirable properties of an adjuvant other than a strong and sustained immunostimulatory ability that should be considered are its safety, biodegradability, stability, ease of mixing and use, broad range of antigens and administration routes that can be used, and its economical manufacture.

A number of adjuvants have been developed. Complete Freund's adjuvant (FCA) is a mixture of a non-metabolizable oil (mineral oil), a surfactant, and killed mycobacterial cells and has been used for many years to enhance the immunologic responses to antigens. Although FCA is effective for production of antibodies, there are problems and hazards associated with its use including a chronic inflammatory response at the site of injection that may be severe and painful which might result in granulomas (Broderson, 1989). FCA is also a hazard for laboratory personnel (Chapel and August, 1976). Incomplete Freund's adjuvant (FIA) does not contain any mycobacterial cells and while it shows adjuvant properties, it is considered less potent than FCA. A number of experimental adjuvants have been reported in recent years (McCluskie and Weeratna, 2001) which include: bacterial toxins such as cholera toxin (CT), *Escherichia coli* labile toxin (LT), IL-12, LPS-derivatives, and oligonucleotides containing CpG motifs. Their mode of action differ but include: a) enhancement of immunological half-life of the co-administered vaccine antigen; b) increased antigen uptake and presentation; and c) modulatory effects on the production of immunomodulatory cytokines resulting in the preferential development of certain types of immune responses (e.g., Th-1 versus Th-2, mucosal, cell mediated, etc). Adjuvants can be classified into two groups: i) immunostimulatory molecules such as CpG oligonucleotides, bacterial toxins and derivatives, the lipopolysaccharide derivative lipid A, cytokines and hormones; and ii) delivery systems which possess inherent immunostimulatory activity such as liposomes, emulsions, microparticles.

With cancer vaccines, the objective is to get the body to elicit its own immune response. Cancer vaccines would typically consist of a source of cancer-associated material or cells (antigen) that may be autologous (from self) or allogenic (from others) to the patient, along with other components (e.g., adjuvants) to further stimulate and boost the immune response against the antigen. Cancer vaccines cause the immune system to produce antibodies to one or several specific antigens, and/or to produce killer T cells to attack cancer cells that have those antigens. T cells in the body react with cancer cells so stimulation of a patient's T cells would increase the ability of T cells to recognize cancer cells. In addition, dendritic cells which are specialized antigen presenting cells, help the immune system to recognize cancer cells by presenting cancer antigens to T cells, making it easier for the immune system cells to react with and attack them. Dendritic cells are the most effective antigen-presenting cells known. Dendritic cells link innate immunity and adaptive immunity. Dendritic cells can efficiently present cancer proteins to activate the immune response, so agents that activate or turn on dendritic cells and the immune response, have clinical applications in preventing or treating cancer and in immunotherapy.

Studies on antitumor immunity have shown that a nontoxic cholera toxin subunit can up-regulate the secretion of IL-12 from DCs suggesting DC maturation and that this molecule acts as an adjuvant to enhance immunity through DC maturation and may be considered a useful adjuvant to raise immunity in a clinical application (Isomura et al., 2005). IL-12 can act as a mucosal adjuvant for coadministered antigens. Studies have shown that proinflammatory cytokines such as IL-12 can replace cholera toxin (CT) as a mucosal adjuvant for antibody induction and are important candidates for use as mucosal adjuvants with HIV and other vaccines (Bradney et al., 2002).

DNA containing an unmethylated CpG motif (CpG oligonucleotides) are a potent immunostimulator and can trigger innate immune responses which promote the combating of infection. Oligonucleotides containing unmethylated CpG motifs act as immune adjuvants, accelerating and boosting antibody responses promoting the production of Th-1 proinflammatory cytokines and inducing the maturation/activation of DCs (Klinman, 2003). CpG oligonucleotides have become a promising immunotherapeutic candidate to assist and direct immune responses such as vaccination or modulation of allergic responses (Dalpke, et al., 2002). CpG oligonucleotides are a strong inducer of IL-12 indicating that it acts as a Th-1 polarizing agent that can be utilized as a potent vaccine adjuvant (Dalpke et al., 2002). Infection such as those caused by intracellular bacteria and viruses, induces innate immunity by causing the infected cells to produce proinflammatory cytokines that directly combat bacterial invaders and to express costimulating surface molecules, which develop adaptive immunity by inducing T cell differentiation. CpG DNA immunostimulatory responses are consistent between in vitro and in vivo studies (Zelenay et al., 2003). Coadministration of CpG DNA with a variety of vaccines has improved protective immunity in animal challenge models and are safe and well-tolerated (Klinman, 2003). A study addressing tumor immune therapy has shown that stimulation of T helper cells with syngeneic tumor cells and antigen-presenting cells in the presence of CpG DNA allows the generation of large numbers of strongly polarized, tumor-specific Th-1 cells, indicating the eradication of established tumors and lymphoma by activating proinflammatory responses and based on this immunostimulatory ability, has clinical utility in immunotherapy (Egeter et al., 2000).

While certain treatments for infectious diseases, cancer, immunodeficiciency and inflammatory disorders and neurological and neurodegenerative diseases are available, improved treatments are needed. Also needed are the development of improved vaccines for a variety of diseases through the use of better vaccine adjuvants.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a method of stimulating and/or modulating the immune and inflammatory response such as a method for stimulating or enhancing immune or inflammatory response or for preventing or treating allergic reactions (e.g., asthma) in a patient which involves administering an effective amount of cyclic di-GMP or a cyclic dinucleotide analogue thereof to a patient in need thereof. Encompassed by this method is enhancement of immune response to a vaccine by administering an effective amount of cyclic di-GMP or a cyclic dinucleotide analogue thereof serving as an adjuvant for the administered vaccine.

The present invention also provides a method for stimulating or enhancing an immune response in a patient by activating dendritic cells or T cells with antigen and with cyclic di-GMP or a cyclic dinucleotide analogue thereof prior to administering the activated dendritic cells or T cells as a cellular vaccine to a patient.

Further provided by the present invention is a method for inhibiting, treating or ameliorating the effects of an injury, disease, disorder, or condition that result in neuronal degeneration by administering to a patient in need thereof an effective amount of cyclic di-GMP or a cyclic dinucleotide analogue thereof to inhibit, treat or ameliorate the effects of the injury, disease, disorder, or condition that result in neuronal degeneration.

Additional aspects of the present invention include a pharmaceutical composition for stimulating or enhancing immune or inflammatory response containing cyclic di-GMP or a cyclic dinucleotide analogue thereof and an immunizing composition containing a vaccine and cyclic di-GMP or a cyclic dinucleotide analogue thereof.

BRIEF DESCRIPTION OF THE DRAWINGS

FIGS. 1A-1H are graphs of the surface phenotype of DCs exposed to c-di-GMP. DCs were left untreated (Untr) or were treated with NaCl, c-di-GMP or LPS for 24 h. DCs were then analysed for expression of the indicated markers, HLA-DR (FIG. 1A), CD83 (FIG. 1B), CXCR4 (FIG. 1C), CCR7 (FIG. 1D), CD80 (FIG. 1E), CD86 (FIG. 1F), MR (FIG. 1G), and CD32 (FIG. 1H), by staining with PE- or FITC-conjugated mAbs. Isotype controls for direct stains exhibited mean fluorescence<5. Results are expresses as percentage of positive cells (□) and as mean fluorescence intensity (MFI, ■).

FIG. 2 is a graph showing endocytic activity of DCs exposed to c-di-GMP. DCs were left untreated (Untr) or were treated with NaCl, c-di-GMP or LPS for 24 h. Mannose receptor-mediated endocytosis was evaluated as the cellular uptake of FITC-dextran (DX) and measured using FACS. Results are expressed as percentage of positive cells.

FIG. 3B) DCs was determined by ELISA. Supernatants were harvested after 24 h of treatment and tested for TNF-α, IL-6, IL-1β, IL-10 and IL-12 Results are expressed as pg/ml. IL-12 concentration was undetectable in immature DC culture supernatants. iDC=immature DC; mDC=mature DC.

FIGS. 7A-7D are graphs showing adjuvant effects of c-di-GMP. (FIG. 7A) Antibodies in serum of mice vaccinated with the ClfA antigen, with or without concomitant administration of c-di-GMP, as detected by ELISA. The histogram shows optical densities for serum samples that were diluted 1/1000 (***, $P<0.001$). (FIG. 7B) Optical density ratios (c-di-GMP/saline group) for results shown in A. (FIG. 7C) Total IgG, and (FIG. 7D) IgG2a and IgG1 isotypes for serum samples diluted as shown. In (FIG. 7C) and (FIG. 7D), for each particular type of antibody assay and dilution tested, O.D. results for mice injected with c-di-GMP versus saline are statistically different from each other ($P<0.001$), as found by one way analysis of variance used in conjunction with the Bonferroni post-hoc test.

FIGS. 8A and 8B show intraperitoneal injection of c-di-GMP activates monocytes and granulocyte recruitment. Peritoneal fluid was analyzed by FACs analysis 18 hours after injection of 200 nmol c-diGMP or 50 μg of LPS. (FIG. 8A) Contour plot of F4/80/LY-6G and CD11b/LY-6G showing recruitment of F4/80$^{high}$ LY-6G$^{med}$ (monocytes) and F4/80$^{med}$ LY-6G$^{high}$ (granulocytes). (FIG. 8B) Histogram showing recruitment of macrophages and granulocytes. These results are representative of 3 independent experiments with 3 animals per group. Difference in relation to controls are denoted by an asterisk for $P<0.05$.

(FIG. 9A) Murine splenic DCs were stimulated with 200 uM c-di-GMP for 24 hours and stained with PE-or FITC-conjugated antibodies specific for CD80 and CD86. The concentrations of the cytokines IL-8 (FIG. 9C) and TNF (FIG. 9B) in the above supernatants were measured by ELISA. The results shown are representative of three similar experiments.

(FIG. 10A) Human immature DCs were stimulated with 200 uM c-di-GMP for 24 hours. Cells were stained with PE-conjugated antibody specific for CD83 or isotype control and were examined by flow cytometry. (FIG. 10B) Dose response of DCs to c-di-GMP. This is a representative histogram of CD83 staining of LPS and c-di-GMP treated immature DCs. (FIG. 10C) Immature DCs were treated with 200 uM c-di-GMP for 24 hours and stained with PE- or FITC-conjugated antibodies specific for CD80, CD86, CCR7, or MHC class II. LPS stimulation of immature DCs was used as a positive control in all experiments. The bar graph represents the ratio of the mean fluorescence intensity (MFI) of the marker specific antibodies to the MFI of the isotype control. The results shown are from a single experiment with a single donor and are representative of three similar experiments. *P<0.01, as determined by Student t test and error bars indicate standard deviation of triplicate measurements.

(FIG. 13A) Activation of p38 MAPK in human dendritic cells. Immature dendritic cells starved overnight were incubated in the absence or presence of c-di-GMP or GMP at specified concentration (µM) for 5 or 30 min. Similar results were found in three independent experiments. (FIG., 13B) Activation of ERK in human macrophages. Macrophages were exposed to c-di-GMP for 5 min. Following exposure to c-di-GMP, dendritic cells and macrophages were harvested to make cell lysates. Identical amount of cell lysates was separated on a 4~12% gradient PAGE gel, transferred onto a piece of PVDF membrane, and analyzed by Western blot with the use of antibodies.

FIG. 16A, lung CFU; FIG. 16B, blood CFU. Bacterial CFU in lung is shown in algebraic scale on x-axis, whereas blood CFU is shown in $log_{20}$+SEM on x-axis and composited from 2 different experiments. * p<0.01 compared to i.n. control GMP (experimental n=6-9 per group).

DETAILED DESCRIPTION OF THE INVENTION

Figure 1A:
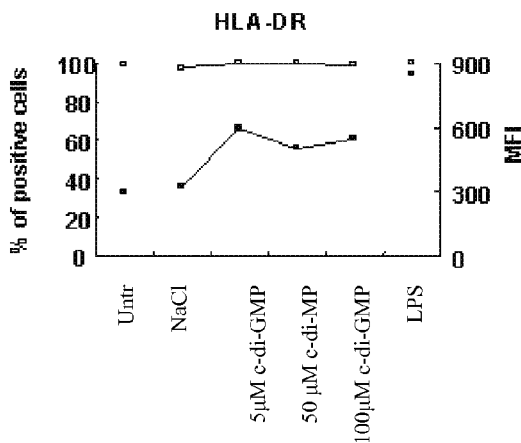

The results shown in Examples 1 and 9 presented hereinbelow show that c-di-GMP stimulates and activates DCs, T cells and the Th-1 response, up-regulates the expression of important costimulatory molecules and the proinflammatory response and show that c-di-GMP has neuroactivity and is neuroprotective against nerve damage.

Stimulation or enhancement (immunostimulation) of the immune and inflammatory response can be achieved by exogenous cyclic di-GMP or cyclic dinucleotides and cyclic dinucleotide analogs. Accordingly, cyclic di-GMP and cyclic dinucleotide analogues thereof can also be used in the development of a drug platform technology against a variety of diseases and immunological and inflammatory diseases including but not limited to infectious disease (such as microbial, bacterial, fungal, viral, and parasitic infections), cancer, HIV and AIDS, rheumatoid arthritis, and Hodgkin's disease. Fungal infections exemplified hereinbelow which can be inhibited or treated with c-di-GMP and cyclic dinucleotide analogues thereof are those caused by *Cryptococcus neoformans, Candida albicans, Pneumocystis carinii*, and species of *Histoplasma, Blastomyces*, and *Coccidioides*. Influenza viral infection, presented in Example 5 hereinbelow, is an example of a respiratory virus that causes an upper respiratory tract viral infection which can be inhibited or treated with c-di-GMP and cyclic dinucleotide analogues thereof. Moreover, not only does c-di-GMP and cyclic dinucleotide analogues thereof inhibit or treat upper respiratory tract viral infections but they also can inhibit or treat secondary pneumonia that sometimes follow an upper respiratory tract viral infection, such as caused by *Haemophilus influenza, Staphylococcus aureus, Streptococcus pyogenes, Mycoplasma pneumoniae*, and *Streptococcus pneumoniae*. In the Examples hereinbelow, infections caused by *Klebsiella pneumoniae* and *Francisella tularensis* are also exemplified as bacterial infections that can be treated by c-di-GMP and cyclic dinucleotide analogues thereof.

Cyclic di-GMP and cyclic dinucleotide analogues thereof are also useful as immunotherapeutic agents against cancers and allergic reactions, and as a vaccine adjuvant (e.g., in DNA vaccines, live attenuated vaccines, killed vaccines). Cyclic di-GMP and cyclic dinucleotide analogues thereof are also useful in affecting neuroactivity and in the inhibition or treatment of various brain, nervous and neural disorders.

Several chemotactic cytokines, or chemokines, inhibit HIV replication by blocking or down regulating chemokine receptors that serve as entry cofactors for the virus. The role of chemokine receptors in HIV pathogenesis has been the subject of intense interest.

Cyclic dinucleotides can alter cytokine and chemokine production and therefore activities of their associated receptors. An aspect of the present invention relates to the immunotherapeutic use of cyclic di-GMP or cyclic dinucleotide analogues thereof in the treatment and/or inhibition of diseases such as HIV and AIDS, rheumatoid arthritis, colon cancer, breast cancer, Hodgkin's disease and lymphomas.

The cyclic dinucleotide compounds described herein alter the expression of DCs, T cells, cytokines, chemokines, costimulatory molecules, and nerve cells. The expression or activity of other proteins, including other receptors, may also be altered by the presence of cyclic dinucleotides, such as c-di-GMP, or cyclic dinucleotide analogues of c-di-GMP.

The present invention therefore provides a method for stimulating or enhancing immune or inflammatory response in a patient. This method involves administering to a patient in need thereof an amount of cyclic di-GMP, or a cyclic dinucleotide analogue thereof, effective to stimulate or enhance the immune or inflammatory response in the patient. The immune response stimulated or enhanced in the present invention preferably includes a Th1 oriented immune response.

By stimulating or enhancing immune or inflammatory response, the present invention is able to treat immunological or inflammatory diseases or disorders such as, but not limited to, arthritis, cancer (e.g., breast cancer, colon cancer, lymphomas, etc.) an autoimmune disease or disorder (e.g., rheumatoid arthritis, multiple sclerosis, lupus erythematosus, etc.), an allergic reaction (e.g., asthma, etc.), a chronic infectious disease (e.g., tuberculosis, cryptococcal infections, etc.), an infectious disease in which the pathogen or toxin produced impairs the immune response thereto (e.g., anthrax), and an immunodeficiency disease or disorder (e.g., HIV and AIDS, etc.). In the case of anthrax, cyclic di-GMP or a cyclic dinucleotide analogue thereof can be used to stimulate or enhance the immune or inflammatory response which has been impaired or inactivated by the anthrax lethal toxin. Thus, the use of cyclic di-GMP or a cyclic dinucleotide thereof is capable of restoring the function of dendritic cells impaired by the toxin. This use would also restore the patient's capacity to stimulate T cells, to upregulate costimulatory molecules and to produce proinflammatory cytokines that were diminished by the toxin.

Based on the ability of c-di-GMP to directly inhibit cancer cell proliferation (Karaolis et al., 2005), an increased host response in fighting infection as seen by an increased ability of antimicrobial activity in vivo compared to in vitro, as well as its ability to biologically modulate the immunological and inflammatory response, small-molecule cyclic dinucleotides, such as c-di-GMP and cyclic dinucleotide analogues thereof, can be used for immunotherapy and to prevent or treat cancer.

Local immunotherapy relates to treating one part of the body. When body tissues become inflamed, the cells of the immune system become stimulated to fight pathogenic bacteria, viruses and other "foreign" cells. Cancer cells are viewed as foreign cells by the immune system so cyclic dinucleotides can be used for local immunotherapy. In this case, the cancer or tumors might be surgically removed and the cyclic dinucleotide (alone or in combination with other drugs) is administered at the site using a syringe or catheter. Cyclic di-GMP or a cyclic dinucleotide analogue thereof can also be used clinically for systemic immunotherapy.

While there is ample evidence to indicate that c-di-GMP plays a key role in regulating virulence properties of bacteria, there is also emerging data from recent studies to indicate that this bacterial product might also modulate host cellular responses. Consistent with this notion, the present inventor and co-workers have shown that synthetic c-di-GMP inhibits basal and growth factor induced proliferation of human colon carcinoma cells (Karaolis et al., 2005). Furthermore, the present inventor and co-workers have recently demonstrated that c-di-GMP pretreatment has a protective effect and inhibits bacterial infection in vivo, promotes antigen-specific antibody responses in vivo, and that c-di-GMP treatment of human monocyte-derived DC in vitro significantly induces Th 1 DC cytokine and chemokine production and increases the cell-surface expression of maturation markers.

To further investigate the immunostimulatory role of c-di-GMP on the innate immune responses of the host in response to bacterial invasion, we used an established mouse model of virulent Gram-negative bacterial pneumonia. We provide additional direct evidence that c-di-GMP is an immunostimulator and acts as a danger signal to stimulate protective innate antibacterial immunity, as the intranasal (i.n.) administration of synthetic c-di-GMP results in improved lung bacterial clearance and prevention of the systemic sequelae caused by K. pneumoniae.

The present invention also provides a method for inhibiting, treating, or ameliorating the effects of an injury, disease, disorder or condition that result in neuronal degeneration. The method involves administering to a patient in need thereof an amount of cyclic-di-GMP, or a cyclic dinucleotide analogue thereof, effective to inhibit, treat, or ameliorate the effects of the injury, disease, disorder, or condition that result in neuronal degeneration. Cyclic di-GMP or a cyclic dinucleotide analogue thereof can be used to protect against neuronal damage and degeneration, such as following a primary nervous system injury or as a result of a neurodegenerative disease or disorder. In addition, such cyclic dinucleotides can be used to ameliorate the effects of disease or disorder that result in a degenerative process.

Non-limiting examples of neurodegeneration include degeneration occurring in either gray or white matter (or both) as a result of various diseases or disorders, including diabetic neuropathy, senile dementias, Alzheimer's disease, Parkinson's Disease, facial nerve (Bell's) palsy, glaucoma, Huntington's chorea, amyotrophic lateral sclerosis (ALS), status epilepticus, non-arteritic optic neuropathy, intervertebral disc herniation, vitamin deficiency, prion diseases such as Creutzfeldt-Jakob disease, carpal tunnel syndrome, peripheral neuropathies associated with various diseases, including uremia, porphyria, hypoglycemia, Sjorgren Larsson syndrome, acute sensory neuropathy, chronic ataxic neuropathy, biliary cirrhosis, primary amyloidosis, obstructive lung diseases, acromegaly, malabsorption syndromes, polycythemia Vera, IgA and IgG gammapathies, complications of various drugs (e.g., metronidazole) and toxins (e.g., alcohol or organophosphates), Charcot-Marie-Tooth disease, ataxia telangectasia, Friedreich's ataxia, amyloid polyneuropathies, adrenomyeloneuropathy, Giant axonal neuropathy, Refsum's disease, Fabry's disease, lipoproteinemia, etc.

Non-limiting examples of nervous system injury include closed head injuries and blunt trauma, such as those caused by participation in dangerous sports, penetrating trauma, such as gunshot wounds, hemorrhagic stroke, ischemic stroke, glaucoma, cerebral ischemia, damages caused by nerve damaging agents such as toxins, poisons, chemical (biowarfare) agents or damages caused by surgery such as tumor excision.

Bis(3'→5')-cyclic diguanylic acid (c-di-GMP), a cyclic dinucleotide, is the preferred embodiment used in the methods of the present invention. The chemical structure of c-di-GMP is presented below.

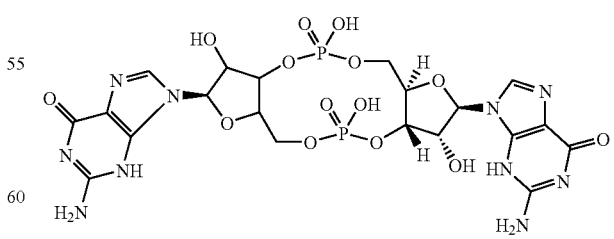

Methods of synthesis of c-di-GMP have been described, for example, by Kawai et al. (Kawai R, Nagata R, Hirata A, Hayakawa Y (2003) A new synthetic approach to cyclic bis (3'-->5')diguanylic acid. *Nucleic Acids Res Suppl.* 3:103-4; hereby incorporated by reference herein).

Besides c-di-GMP, a cyclic dinucleotide analogue thereof which acts as a c-di-GMP agonist, i.e., having the same effect as c-di-GMP, can be used. Non-limiting examples of cyclic dinucleotide analogues of c-di-GMP are presented below as compounds (I)-(XX):
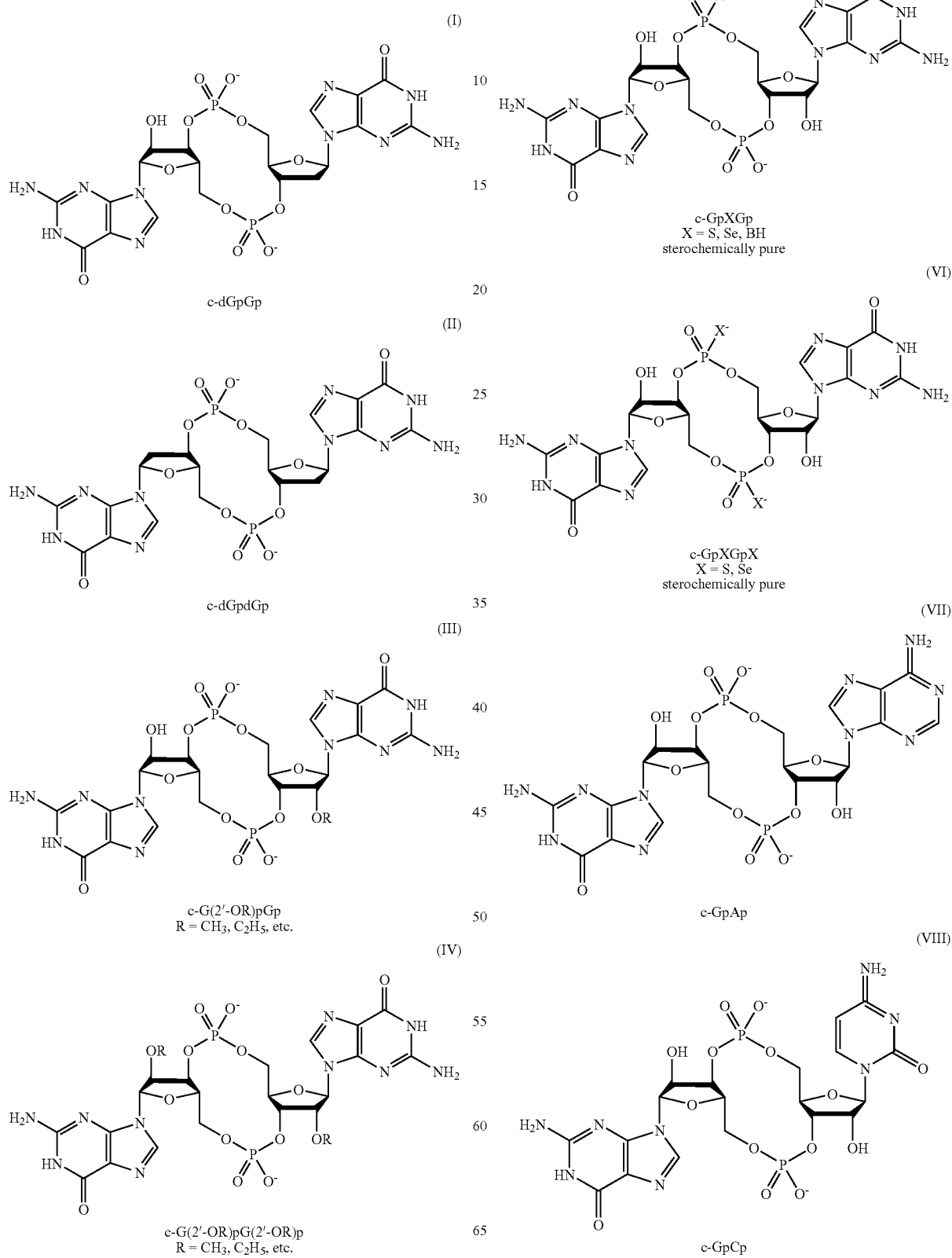

-continued
(IX)
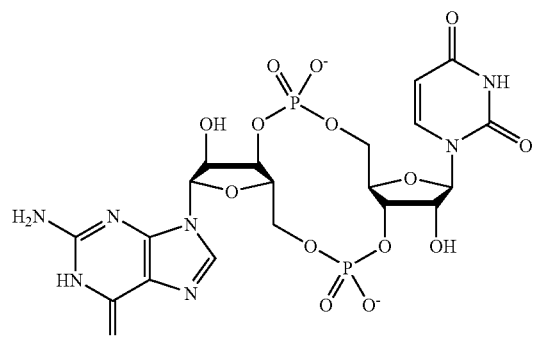
c-GpUp
(X)
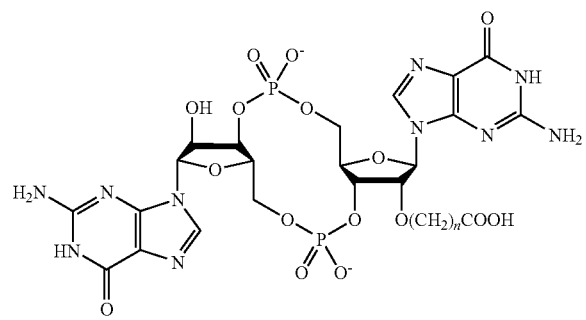
c-GpIp
(XI)
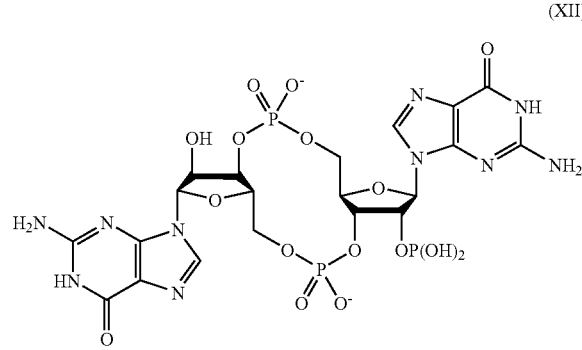
(XII)
-continued
(XIII)
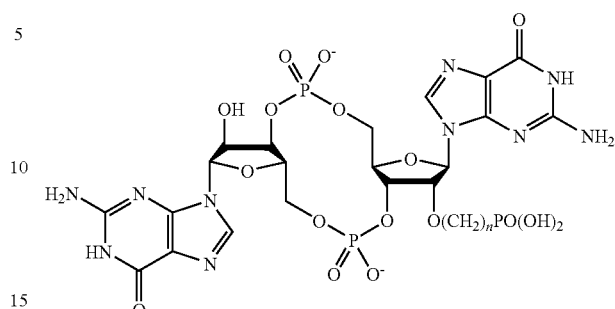
(XIV)
(XV)
(XVI)
(XVII)

-continued

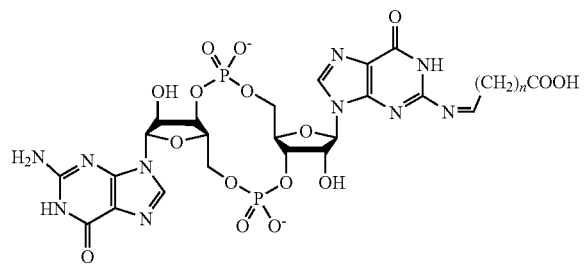

(XVIII)

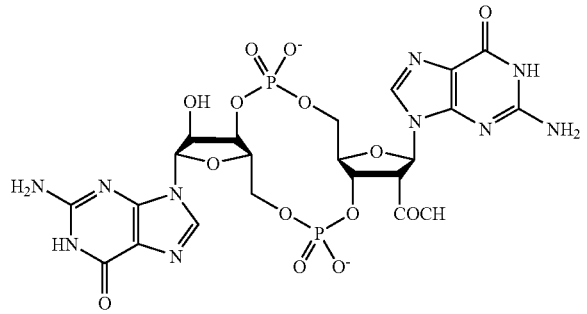

(XIX)

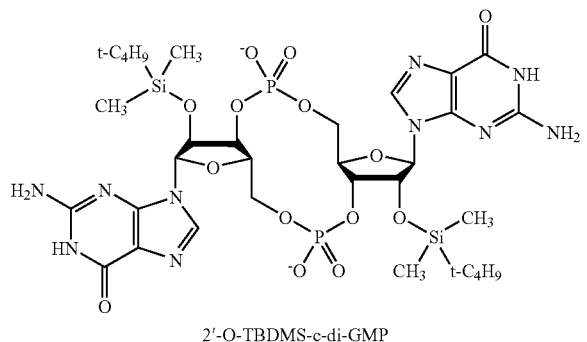

(XX)

2'-O-TBDMS-c-di-GMP

The above cyclic dinucleotides are only preferred embodiments of the cyclic dinucleotide analogues of c-di-GMP and are not intended to be limiting. For example, the guanine base can be substituted with other bases.

As cyclic dinucleotides may also be modified to yield cyclic dinucleotide analogues, these modified cyclic dinucleotide analogues, and methods of use thereof, are included as aspects of the present invention. c-di-GMP can be modified, for example at a C, N, O, or P, to yield a c-di-GMP analogue. c-di-GMP analogues for use in the present invention have an activity similar to that of c-di-GMP. For example, certain c-di-GMP analogues either increase or reduce the stimulation of DCs and T cells, expression of various cytokines, chemokines, and/or their associated receptors. The degree of reduced expression in the presence of the c-di-GMP analogue may be the same, less, or greater than the degree of reduced expression in the presence of c-di-GMP. Certain c-di-GMP analogues increase expression of certain cytokines. The degree of increased cytokine expression in the presence of the c-di-GMP analogue may be the same, less, or greater than the degree of increased cytokine expression in the presence of c-di-GMP.

A c-di-GMP analogue may be further modified, yielding another c-di-GMP analogue. The further modified c-di-GMP analogues will have properties similar to the original c-di-GMP analogue. These further modifications may result in desired properties, for example, altered toxicity, altered immune or inflammatory response, or uptake into cells.

MeSate-c-di-GMP is a cyclic dinucleotide analogue of cyclic di-GMP which has increased hydrophobicity and lipophilicity over c-di-GMP for increasing cellular uptake and cell-membrane permeability, and therefore, increased bioavailability. Modification of either one or both of the phosphodiester linkage in c-di-GMP by a phosphotriester, which is converted to the phosphodiester would occur via enzymatic cleavage inside the cell. This derivative (analogue) has the negative charge of the phosphate group transitorily masked with carboxyesterase labile S-acyl-2-thioethyl (SATE) groups. Once intracellular, such derivatives are expected to be hydrolyzed in the body to release the parent cyclic dinucleotide molecule. While the present invention relates to the use of cyclic dinucleotides (and not oligonucleotides), MeSate phosphotriester molecules have been synthesized to overcome the hurdle of poor uptake of oligonucleotides (Vives et al., 1999). The synthesized molecules are masked with a carboxyesterase labile S-Acyl-2-thioethyl (SATE) group to gain more lipophilicity. This SATE group effectively crosses the cell membrane. Particular oligonucleotide molecules bearing the enzymolabile SATE groups with acyl equal to acetyl were named MeSATE prooligos. MeSATE nucleoside monophosphates have also been synthesized (Peyrottes et al., 2004).

2'-O-TBDMS-c-di-GMP is a 2'-O-blocked derivative (analogue) of cyclic di-GMP that is expected to have similar chemical properties to those of natural c-di-GMP, but is also expected to have higher cell-membrane permeability than that of natural c-di-GMP. 2'-O-monopyrenylmethyl-c-di-GMP (fluorescently labeled) and 8-monotritium-labeled c-di-GMP (radioactively labeled) can be used for detection assays.

c-di-GMP is well-suited for therapeutic use. It is nontoxic on normal rat kidney cells exposed to 400 µM C-di-GMP for 24 h, and non-lethal in CD1 mice after 24 h when given 50 µl of 200 µM c-di-GMP. c-di-GMP is soluble in water physiological saline, and stable at physiological conditions (pH 10). The structure of the molecule is known, and it is small in size, approx. 700 Da. Analogues can be easily designed and synthesized.

Numerous c-di-GMP analogues can be readily synthesized. A collection of a number of c-di-GMP analogues will be considered to be a library of c-di-GMP analogues. A library of c-di-GMP analogues will be useful in the methods of the present invention. For example, a library of c-di-GMP analogues may be screened to identify a particular c-di-GMP analogue of a desired activity. A particular c-di-GMP analogue may undergo a variety of tests, including testing its ability to stimulate the immune system, testing its effect on DCs, cytokines, testing its ability to affect certain infectious diseases, cancer, immune and inflammatory disorders, testing its use as a vaccine adjuvant, testing its use against allergic reactions and its neuroprotective ability.

Standard techniques such as detection of antibodies to chemokines, protein labeling, binding assays, and functional assays may be used to detect cytokine, chemokine, and receptor expression in a cell.

Pharmaceutical compositions containing at least one of c-di-GMP or a cyclic dinucleotide analogue thereof, or mixtures thereof, for use in accordance with the methods of the present invention may be formulated in conventional manner using one or more physiologically acceptable carriers or excipients. The carrier(s) must be "acceptable" in the sense of being compatible with the other ingredients of the composition and not be deleterious to the recipient thereof. The carrier must be biologically acceptable and inert, i.e., it must permit the cell to conduct its metabolic reactions so that the compound of this invention may effect its inhibitory activity.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results. It will also be appreciated that c-di-GMP or a cyclic dinucleotide thereof may be used alone as the active ingredient or in combination with other active agents.

The term "carrier" refers to a diluent, adjuvant, excipient, or vehicle with which the c-di-GMP or cyclic dinucleotide thereof is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulfate; a glidant, such as colloidal silicon dioxide; a sweetening agent, such as sucrose or saccharin; and/or a flavoring agent, such as peppermint, methyl salicylate, or orange flavoring.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated, i.e., enterically-coated by methods well-known in the art.

Preparations for oral administration may be suitably formulated to give controlled release of the active compound.

For topical administration, c-di-GMP or a cyclic dinucleotide analogue thereof is incorporated into topically applied vehicles such as salves or ointments.

For buccal administration, the compositions may take the form of tablets or lozenges formulated in conventional manner.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

The compositions may also be formulated in rectal compositions such as suppositories or retention enemas, e.g., containing conventional suppository bases such as cocoa butter or other glycerides.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. A nasal spray, which does not require a pressurized pack or nebulizer as in an inhalation spray, can alternatively be used for intranasal administration. In the case of a pressurized aerosol, the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

A typical regimen for treatment includes administration of an effective amount over a period of several days, up to and including between one week and about six months.

In the present application, "patient" will encompass any mammal that requires immunostimulation or immunomodulation, requires prevention of disease, or is suffering from an immune or inflammatory disease involving production of cytokines, chemokines and/or associated receptors.

The effective dose for immunotherapy appears to be in the micromolar range, such as between about 1 µM and 200 µM, preferably about 5 µM to 100 µM, more preferably about 50 µM to 100 µM. The effective dose for protection from neurodegeneration (i.e., neuroprotection) is in a range of about 0.1 to 100 µM, preferably about 1 to 50 µM, more preferably about 1 to 10 µM. It is within the skill of those in the pharmaceutical art to determine with routine experimentation what dosage of c-di-GMP or a cyclic dinucleotide analogue thereof will be needed, depending on route of administration, to deliver such an effective dose. The desired dose may be administered as 1 to 6 or more subdoses administered at appropriate intervals as required. The compounds may be administered repeatedly, or may be slowly and constantly infused to the patient. Higher and lower doses may also be administered.

It is understood that the dosage of c-di-GMP or a cyclic dinucleotide analogue thereof administered in vivo may be dependent upon the age, sex, health, and weight of the recipient, kind of concurrent treatment, if any, frequency of treatment, and the nature of the pharmaceutical effect desired. The ranges of effective doses provided herein are not intended to be limiting and represent preferred dose ranges. However, the most preferred dosage may be tailored to the individual subject, as is understood and determinable by one skilled in the relevant arts. See, e.g., Berkow et al., eds., *The Merck Manual*, 16th edition, Merck and co., Rahway, N.J., 1992; Goodman et al., eds., *Goodman and Gilman's The Pharmacological Basis of Therapeutics*, 8th edition, Pergamon Press, Inc., Elmsford, N.Y. (1990); Katzung, *Basic and Clinical Pharamacology*, Appleton and Lange, Norwalk, Conn., (1992); *Avery's Drug Treatment: Principles and Practic of Clinical Pharmacology and Therapeutics*, 3rd edition, ADIS Press, LTD., Williams and Wilkins, Baltimore, Md. (1987), Ebadi, *Pharmacology*, Little, Brown and Col, Boston, (1985), *Remington's Pharmaceutical Sciences*, seventeenth edition, ed. Alfonso R. Gennaro, Mack Publishing Company, Easton, Pa. (1985) which references are entirely incorporated herein by reference.

The methods of the present invention may be practiced by administration of cyclic di-GMP or cyclic dinucleotide analogues thereof by themselves or in a combination with other active ingredients, including antiviral compounds and/or antibiotic agents in a pharmaceutical composition. Other active agents suitable for use herein are any compatible drugs that are effective by the same or other mechanisms for the intended purpose, or drugs that are complementary to those of the present agents. These include agents that are effective antibiotic agents.

Cyclic di-GMP or a cyclic dinucleotide thereof may be used in vaccine formulations as an adjuvant in order to boost, stimulate or modulate the immune response. Thus, one aspect of the method for stimulating or enhancing immune or inflammatory response according to the present invention is to enhance the immune response to a vaccine where an effective amount of a vaccine or antigen is administered to the patient in need thereof in combination with an amount of cyclic di-GMP or a cyclic dinucleotide analogue thereof effective to enhance the patient's immune response to the vaccine.

Antigens administered to a patient with cyclic di-GMP or a cyclic analogue thereof as adjuvant include purified or partially-purified preparations of protein, peptide, carbohydrate or lipid antigens, and/or antigens associated with whole cells, particularly dendritic cells that have been mixed with the antigen. On the whole, any pathogen or tumor and/or differentiation associated antigen can be considered as a possible immunogen to be given at the same time as cyclic di-GMP, or a cyclic dinucldotide analogue thereof, as adjuvant.

It is fully expected that the present invention will enhance the immune response to the administration of any vaccine, including a protein vaccine, a polysaccharide vaccine, a DNA vaccine, a killed or live attenuated bacterial or viral vaccine, an autologous or allogeneic cancer vaccine, a dendritic or T cell vaccine, etc. While the term "vaccine" is often used to refer only to vaccinations intended to induce prophylaxis, the term as used throughout the present specification and claims is intended to include vaccination for therapeutic purposes as well. For example, vaccines that comprise tumor-associated antigens are intended to induce an immune response against tumors. Vaccines to viral particles may be used not only to create prophylaxis against the virus, but also to eradicate an existing viral infection. Thus, for example, vaccines are available against HBV and others against AIDS and HCV, which are in active development. Active vaccination against amyloid-β plaques is also in development for the treatment of Alzheimer's disease. Thus, the term "vaccine" applies to the administration of any antigen for the purpose of inducing an immune response against that antigen or to a cross-reactive antigen that exists in situ. Preferred vaccines include an influenza, smallpox, anthrax, hepatitis B virus, human pappilloma virus, herpes simplex virus, polio, tuberculosis or anti-cancer vaccine.

The amount of antigen(s) present in each vaccine dose, is selected as an amount capable of inducing a protective immune response in vaccinated subjects. This amount will depend on the specific antigen and the possible presence of typical adjuvants, and can be identified by a person skilled in the art. In general, each dose will contain 1-1000 micrograms of antigen, preferentially 10-200 μg. Further components can be also present advantageously in the vaccine. The effective amount of cyclic di-GMP or a cyclic dinucleotide analogue thereof as adjuvant in an immunizing composition is in a range of about 1 to 200 μM, preferably about 5 to 100 μM, more preferably about 50 to 100 μM.

The vaccine composition can be formulated in any conventional manner, as a pharmaceutical composition comprising sterile physiologically compatible carriers such as saline solution, excipients, adjuvants (if any, in addition to the cyclic di-GMP or a cyclic dinucleotide analogue thereof), preservatives, stabilizers, etc.

The vaccine can be in a liquid or in lyophilized form, for dissolution in a sterile carrier prior to use. The presence of alum or liposome-like particles in the formulation are also possible, since they are useful for obtaining a slow release of the antigen(s). Other strategies for allowing a slow release of the vaccine can be easily identified by those skilled in the art and are included in the scope of this invention.

The pharmaceutically acceptable carrier, excipient, diluent or auxiliary agent can be easily identified accordingly for each formulation by a person skilled in the art.

This method of the present invention can be used in both prophylactic and therapeutic treatment of infectious diseases and cancer. In particular, the method can be used in a treatment for preventing viral and bacterial diseases (i.e., prophylactic vaccines) as well as for the treatment of severe chronic infection diseases (i.e., therapeutic vaccines). Moreover, the method can also be used in the prevention/inhibition and treatment of cancer or other diseases and conditions when suitable antigens are used.

This can be achieved by using antigens against infectious agents associated with human malignancies, e.g., EBV, HPV and *H. pilori*, or well defined tumor associated antigens such as those characterized in human melanoma, e.g., MAGE antigens, thyrosinase gap100, and MART, as well as in other human tumors.

Also encompassed by the present invention, as will be appreciated by those of skill in the art, is a method for stimulating or enhancing an immune response in a patient by activating dendritic cells or T cells (either autologous or allogeneic) ex vivo with an effective amount of antigen and with an effective amount of cyclic di-GMP or a cyclic dinucleotide thereof prior to administering the activated dendritic cells or T cells as a cellular vaccine to a patient.

Having now generally described the invention, the same will be more readily understood through reference to the following examples which are provided by way of illustration and is not intended to be limiting of the present invention.

EXAMPLE 1

Preparation of Cell Culture and Treatments

Peripheral blood mononuclear cells (PBMC) were isolated by Ficoll-Hypaque gradient separation of buffy coats obtained from healthy volunteer blood donors by the Transfusion Center of Università Degli Studi "La Sapienza" Rome. DCs were generated from monocytes purified from PBMC by positive selection using magnetic cell separation columns and CD14 Microbeads. Highly enriched monocytes (>95% CD14$^+$) were cultured at $6 \times 10^5$/ml in RPMI 1640 medium supplemented with 15% heat-inactivated fetal calf serum (FCS), L-glutamine and penicillin-streptomycin and 250 ng/ml granulocyte macrophage-colony stimulating factor (GM-CSF) and 500 U/ml interleukin (IL)-4 at 37° C. for 5 days. Differentiation to DC was assessed both by morphologic observation and the detection of specific surface markers by flow cytometry. These cells were CD14$^-$, CD1a$^+$, HLA-DR$^{intermediate}$, HLA-ABC$^{intermediate}$ CD80$^{low}$, CD86$^{low}$ consistent with an immature DC phenotype. Untreated immature DCs were used as controls. After 5 days of culture c-di-GMP and/or 200 ng/ml lipopolysaccharide (LPS) (*Escherichia coli* serotype 0111:B4) were added to immature DCs. LPS-treated DCs became stimulated/activated and produced CD83$^+$, HLA-DR$^{high}$, HLA-ABC$^{high}$ consistent with a mature DC phenotype.

A dose-response titration curve using 0.5, 5, 50, 100 and 200 uM c-di-GMP was performed. No effect was obtained using 0.5 µM c-di-GMP, and 200 µM gave inconsistent results. Only experiments performed using c-di-GMP at the concentration of 5, 50 and 100 µM are reported. Experiments using trypan blue exclusion tests were always performed in order to exclude any aspecific toxicity of c-di-GMP. NaCl (0.9%) used to resuspend the compound was always included as control.

c-di-GMP Stimulates and Activates Human Dendritic Cells

Cell staining was performed using mouse monoclonal antibodies FITC- or PE-conjugate. The following mAbs were used: CD14 (IgG1, PE), CD1a (IgG1, FITC), HLA-DR (IgG2a, FITC), HLA-ABC (IgG1, FITC), CD80 (IgG1, FITC), CD86 (IgG1, FITC); CD83 (IgG2b, PE), CXCR4 (IgG2aPE), CCR5 (IgG2a, FITC), CD32 (IgG2b, FITC). CD40, CCR7 and mannose receptor (MR) staining was performed using mouse mAb followed by FITC-conjugated affinity purified, isotype-specific goat anti-mouse Abs. Samples were analyzed using a FACScan flow cytometer and CellQuest software (Becton Dickinson). To investigate whether c-di-GMP induced phenotypic differentiation of human DCs, immature and mature DCs were cultured with c-di-GMP for 24 h and then analyzed for surface molecule expression.

Figure 1B:
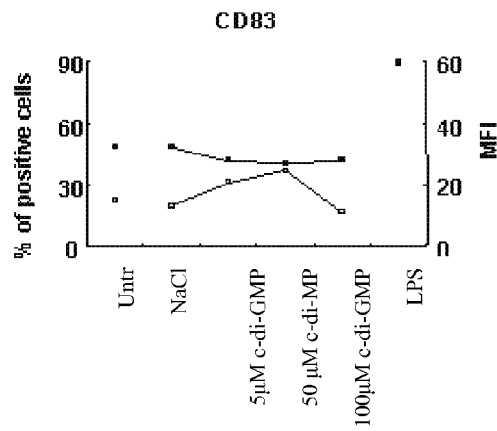
Figure 1C:
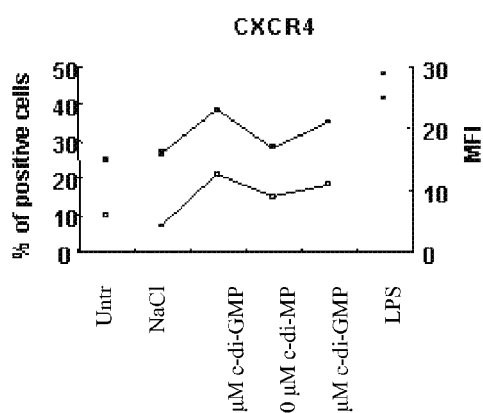
Figure 1D:
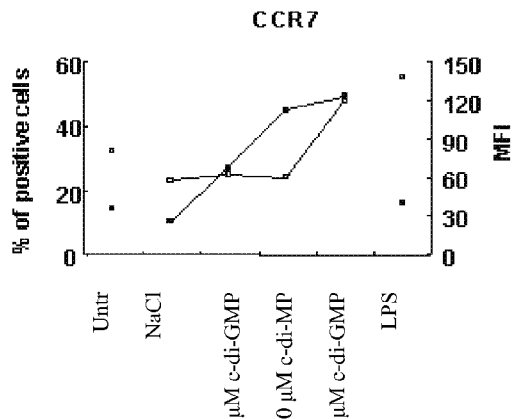
Figure 1E:
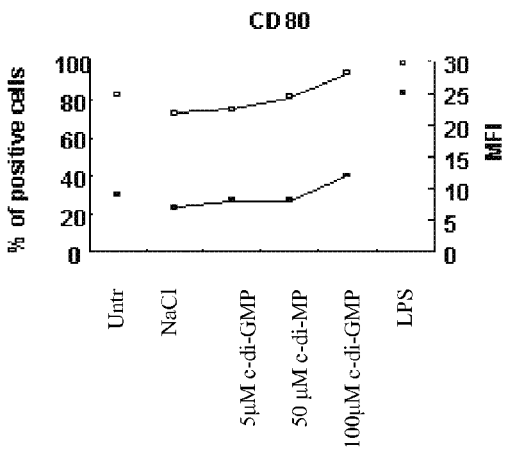
Figure 1F:
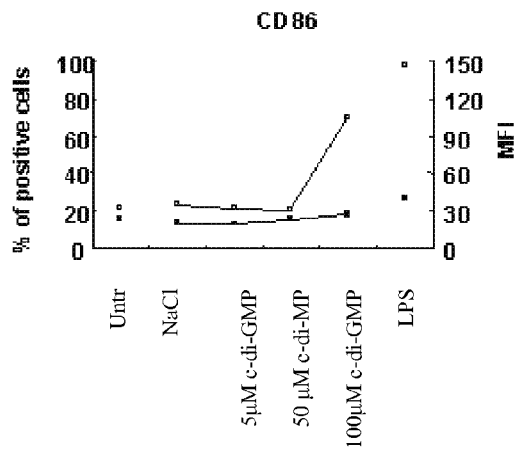

The results indicate that c-di-GMP stimulates immature DCs. In FIG. 1A, c-di-GMP up-regulated the expression of DC antigen-presenting cell MHC associated HLA-DR as seen by an increase in mean fluorescence intensity (MFI), and resulted in a high percentage of positive (expressing) cells similar to the result of LPS treatment. HLA-DR is an important molecule involved in the presentation of antigenic peptides to CD4$^+$ T cells. C-di-GMP significantly increased the expression of the chemokine receptors CXCR4 and CCR7 (as seen by a dramatic increase in both mean fluorescence and percentage of expressing cells in FIGS. 1C and 1D). These important chemokine receptors are known to be involved in the migration of mature DC towards lymph nodes. CXCR4 expressing cells are attracted to sites of inflammation and CCR7 is a marker of DCs so these findings suggest an increase in the proinflammatory response and the attraction of these cells to sites of inflammation. C-di-GMP slightly up-regulated the expression of CD83 in a dose-dependent manner (as seen by mean fluorescence of positive cells) with overstimulation resulting in no effect seen at high concentrations (FIG. 1B). CD83 is a maturation antigen. In FIG. 1F, c-di-GMP also up-regulated and stimulated DC antigen-presenting cell costimulatory molecule CD86 (B7-2) (as seen by an increase in the percentage of positive cells). C-di-GMP slightly increased the expression of the costimulatory molecule CD80 (B7-1) (as seen by mean fluorescence and the percentage of expressing cells) in a dose-dependent manner (FIG. 1E). In FIG. 1G, c-di-GMP reduced the expression of mannose receptor (MR) in a dose-dependent manner (as seen by mean fluorescence).

To determine whether the treatment of DCs with c-di-GMP modulates the expression of cell surface molecules that contribute to antigen uptake, the expression of MR and CD32 was tested. At the highest dose, c-di-GMP, similarly to LPS, but to a lower extent, down-regulated MR molecules on the surface of immature DCs (FIG. 1G), while CD32 expression was not affected (FIG. 1H). c-di-GMP did not interfere with LPS-induced maturation (data not shown). As c-di-GMP clearly has an activating effect on immature DC, it appears not to be able to up-regulate surface expression of markers that are already highly expressed on LPS-matured DC. Interestingly, c-di-GMP did not affect surface expression of CD1a and HLA-ABC, involved in the presentation of lipidic and antigenic peptides respectively; CCR5, a chemokine receptor involved in the migration of immature DC in inflamed tissue; and CD40, which transduces activation signals (data not shown).

Taken together, these data suggest that T cells are being activated by c-di-GMP. The results show that iDCs are being activated/matured by c-di-GMP. The results show that the costimulatory molecules CD80 and CD86 are up-regulated by c-di-GMP treatment. The finding that CD83 is not significantly affected (in contrast to LPS which affects most cells and molecules) suggests that c-di-GMP has the advantage of specificity and does not have a general effect on all cells of the immune response. The findings clearly indicate the stimulation of antigen-presenting cells and antigen-specific receptors such as signal 1 MHC factors (e.g., HLA-DR) and signal 2 costimulatory molecules (CD86 and CD80).

c-di-GMP Does Not Modulate DC Endocytic Activity

Mannose receptor (MR)-mediated endocytosis was measured as the cellular uptake of FITC-dextran (DX) and quantified by flow cytometry. A total of 2×10$^5$ cells per sample were incubated in media containing FITC-DX (1 mg/ml) (Mv 40,000). After 15 min of incubation at 37° C. or 4° C. (as negative control), cells were washed four times with cold PBS containing 1% FCS and 0.01% NaN3 and fixed in 1% formaldehyde. The background (cells pulsed at 4° C.) was always subtracted. As shown in FIG. 2, c-di-GMP did not induce any major effect. As expected, LPS down-regulated the uptake of FITC-DX, consistent with a mature phenotype.

c-di-GMP Stimulates/Up-Regulates Cytokine Production by Dendritic Cells

Analysis of supernatant cytokine content was performed both on treated (c-di-GMP) or untreated saline control (NaCl) immature DCs (iDC) and mature DCs (mDC). Culture supernatants were collected after 24 h treatment and IL-1β, IL-6, IL-10, IL-12, and TNF- α contents were measured using a sandwich ELISA according to the manufacturer's instructions.

Figure 3A:
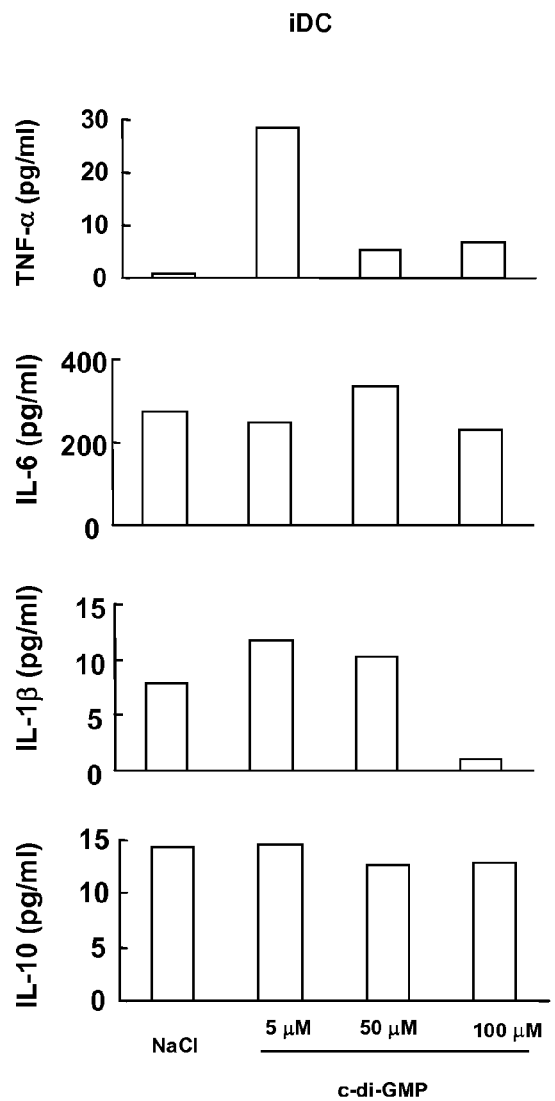
FIGS. 3A and 3B are graphs showing the effect of c-di-GMP on cytokine production. Analysis of cytokine supernatant concentration in NaCl (used as control) or c-di-GMP-treated immature (FIG. 3A) or mature (LPS-treated.
Figure 3B:
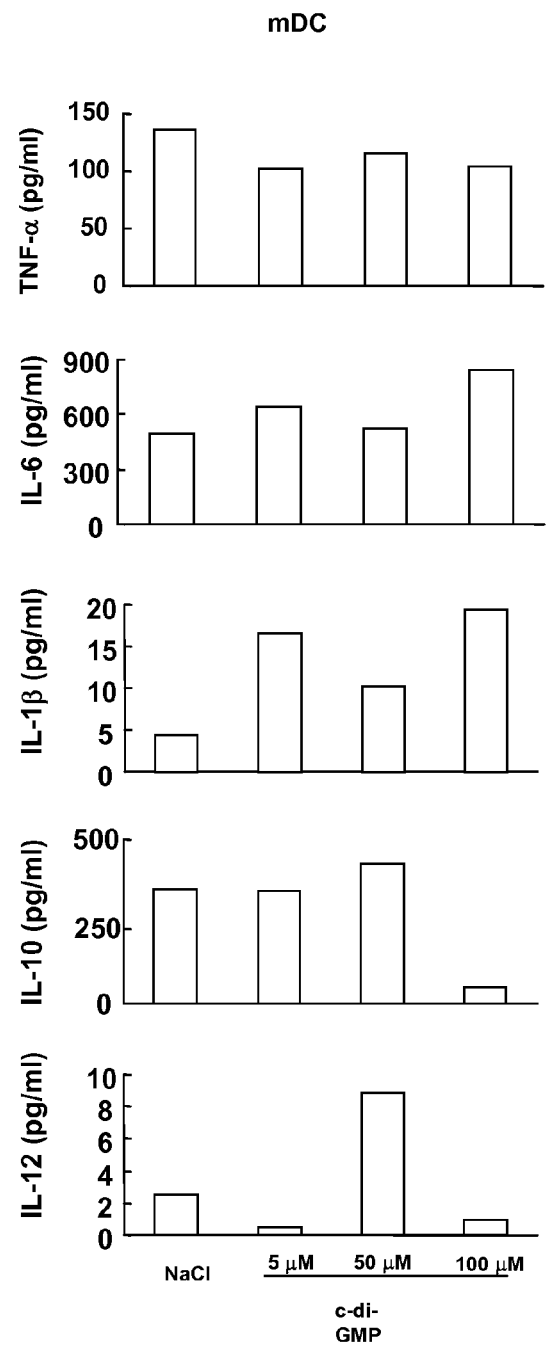

The results clearly indicated that c-di-GMP stimulates cytokine production in both iDCs and mDCs and clearly show that iMCs are being activated/matured by c-di-GMP (FIG. 3A). In iDCs, a 5 µM dose of c-di-GMP triggered a dramatic increase in the production of TNF-α, demonstrating an increase in the production of proinflammatory molecules. C-di-GMP induced an increase in IL-6 in mDCs at 100 µM and a major increase in IL-1β in mDCs, supporting the induction of a proinflammatory response (FIG. 3B). IL-12 is a central cytokine in the Th-1 response whose expression leads to IFN-γ production. IL-12 secretion was undetectable in immature DCs; however, c-di-GMP induced a dramatic increase in IL-12 production in mDCs at 50 µM. The increase in IL-12 further confirms and is consistent with immunostimulation and the induction of a proinflammatory response, particularly a Th-1 response. There was no major effect on IL-10 expression which is an anti-inflammatory molecule. This data is again consistent with the previous data that c-di-GMP treatment is immunostimulatory and induces a proinflammatory response and therefore can be used in various clinically therapeutic applications such as an immunotherapeutic agent or adjuvant in vaccine development.

c-di-GMP Up-Regulates the Immunostimulatory Capacity of Dendritic Cells

DCs were stimulated for 24 h with c-di-GMP or LPS and were then extensively washed and suspended in RPMI 1640 supplemented with 10% human serum, L-glutamine, and penicillin/streptomicin, irradiated (3,000 rad from a $^{137}$Cs source) and added in graded doses to $1 \times 10^5$ responder T cells in 96 flat-bottom microplates. Responder cells were autologous or allogeneic PBMC. After 5 days, cultures were pulsed for 18 h with 0.5☐Ci/well of [$^3$H]thymidine. Cells were then harvested onto glass fiber filters, and [$^3$H]thymidine incorporation was measured by liquid scintillation spectroscopy.

Figure 4A:
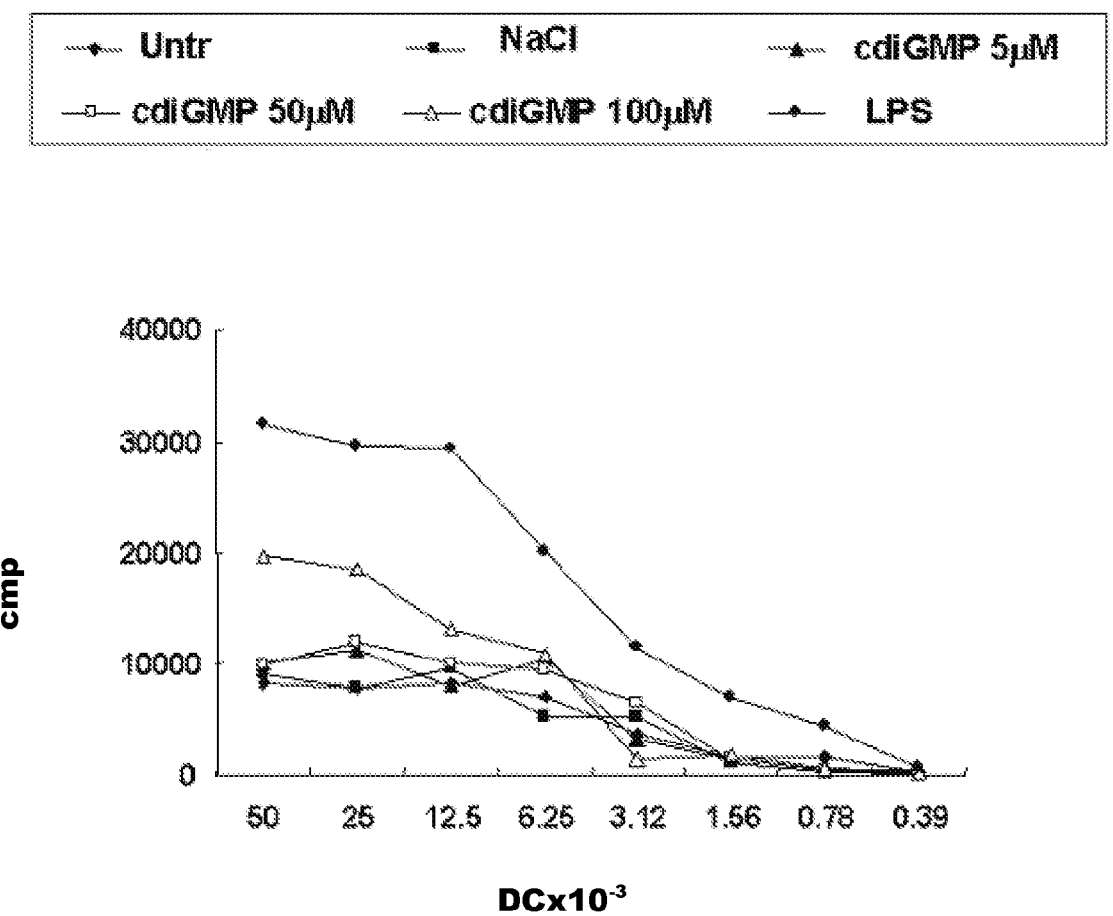
FIGS. 4A and 4B are graphs showing stimulation of autologous and allogeneic PBMC. DCs were left untreated (Untr) or were treated with NaCl, c-di-GMP or LPS for 24 h. A mixed leukocyte reaction, with irradiated DCs cultured at different cell numbers with 1×105 autologous (FIG. 4A) or allogeneic (FIG. 4B) PBMC, was then set up. [$^3$H] thymidine incorporation was measured after 5 days. Results are expressed as count per minutes (cpm).
Figure 4B:
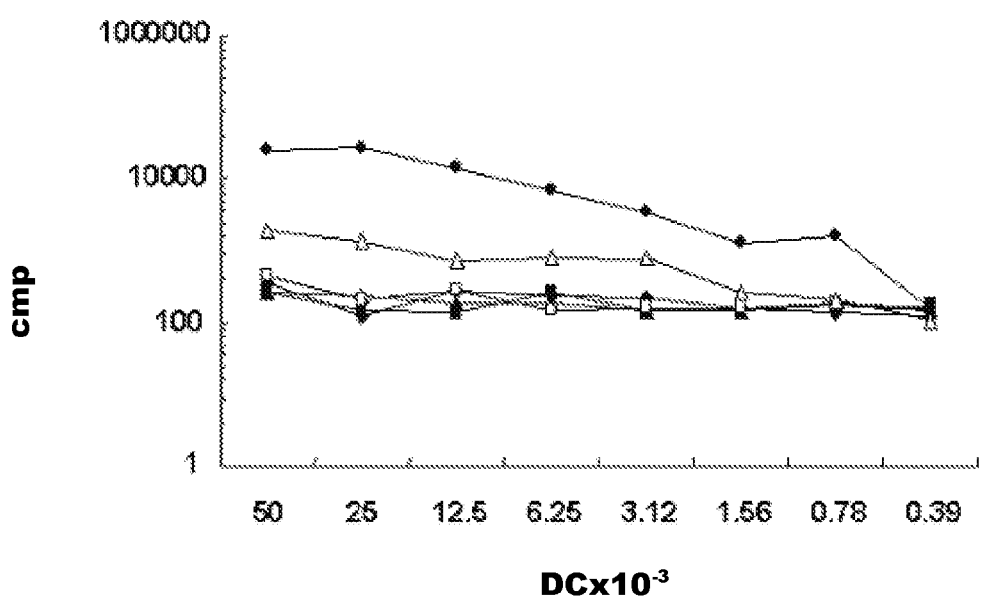

If DCs are activated and if proinflammatory cytokines are stimulated, then T cells are activated. If irradiated (i.e., dead) DCs are mixed with normal T cells, the proliferation of DCs is not expected; however, the proliferation of T cells is expected. Therefore, in this experiment, thymidine incorporation indicates the stimulation of T cells. The results in FIGS. 4A and 4B, demonstrating the proliferation of DCs, indicate that c-di-GMP treatment activates T cells. The results show that if cells are treated with LPS, T cells are highly activated consistent with its known T cell stimulatory activity. The results also show the ability of 100 μM c-di-GMP-treated immature DCs to induce both autologous (FIG. 4A) and heterologous (FIG. 4B) T cell proliferation compared to untreated DCs (five-fold and two-fold increase respectively). Taken together, and consistent with previous data, these results show that c-di-GMP treatment up-regulates and activates/stimulates the proliferation of T cells, further demonstrating that c-di-GMP is an innate stimulator and can be used clinically in immunotherapeutic applications.

c-di-GMP Does Not Modulate Dendritic Cell Apoptosis

FITC-Annexin V/Propidium Iodure (PI) double staining was used to detect apoptosis of DCs treated with c-di-GMP. Immature and mature DCs, untreated or treated with c-di-GMP for 24 h, were harvested and washed twice with ice cold PBS; specific binding of FITC-annexin V and staining with PI was performed with an apoptosis detection kit accordingly to the manufacturer's instructions. The cells were then analyzed by flow cytometry.

As shown in Table 1, c-di-GMP did not appear to have any effect on DC apoptosis. c-di-GMP did not modulate the percentage of annexin V$^-$/PI$^-$ (early apoptosis) and annexin V$^-$/PI$^+$ DCs (late apoptosis) after 24 h treatment. These results indicate a lack of an anti-inflammatory response and that there is no tolerance of DCs to c-di-GMP. These data are consistent with earlier data that show that c-di-GMP is clearly an immunostimulatory molecule and activates the proinflammatory response.

TABLE 1

|  | Early apoptosis (% of annexin V$^+$/PI$^-$ cells) | Late apoptosis (% of annexin V$^+$/PI$^+$ cells) |
| --- | --- | --- |
| Untreated | 29 | 56 |
| NaCl | 22 | 39 |
| cdiGMP 5 μM | 23 | 36 |
| cdiGMP 50 μM | 31 | 40 |
| cdiGMP 100 μM | 18 | 42 |
| LPS | 21 | 52 |
| LPS + NaCl | 28 | 38 |
| LPS + cdiGMP 5 μM | 32 | 33 |
| LPS + cdiGMP 50 μM | 31 | 46 |
| LPS + cdiGMP 100 μM | 29 | 47 | c-di-GMP has Desired Immunotherapy and Adjuvant Properties

The data obtained showing treatment with c-di-GMP is immunostimulatory, triggers a Th-1 response and induces a proinflammatory response, is clearly consistent with an increase in the host response in fighting infection in vivo. This cellular data is consistent with in vivo data from the laboratory of the present inventor showing that c-di-GMP attenuates virulence and inhibits bacterial infection in an animal model of infection. Cyclic dinucleotides such as c-di-GMP stimulate vertebrate immature immune cells to induce maturation and to produce various factors including TNF-α as well as Th-1 cytokines such as IL-12. Therefore, c-di-GMP functions as an adjuvant for regulating the initiation of the Th-1 response and has clinical utility in vaccine development.

Regarding its use as an adjuvant, the data overall also strongly indicate that if administered with an antigen, there is increased presentation of antigen through stimulation of HLA-DR. Cyclic di-GMP facilitates and induces costimulation via an increase in CD80 and CD86, facilitates activation of a Th-1 immune response as seen by the induction of IL-12, facilitates the stimulation of an overall proinflammatory pattern as seen by the increase in IL-1β and TNF-α and facilitates the stimulation of T cells as seen by the data in the mixed leukocyte reaction. C-di-GMP treatment, however, does not appear to stimulate CD83, which is desirable, as this suggests a degree of selectivity for DCs compared to LPS which is broadly hyperstimulatory and results in hyperreactions.

c-di-GMP is an Immunostimulatory Molecule

The hypothesis that c-di-GMP is not only an important microbial signaling molecule, but is also a novel immunostimulatory agent that can modulate the host immune response, was tested. It is now reported that c-di-GMP is an immunomodulatory (immunostimulatory) molecule triggering an innate and adaptive immune response. Intramammary treatment of mice with c-di-GMP 12-and 6 h prior to S. aureus challenge gave a protective effect and a 10,000-fold reduction in CFUs in tissues (P<0.001). Intramuscular vaccination of mice with two injections of c-di-GMP co-injected with S. aureus ClfA antigen produced serum with significantly higher anti-ClfA IgG antibody titers (P<0.001) compared to ClfA alone. Intraperitoneal injection of mice with c-di-GMP activated monocyte and granulocyte recruitment. Human immature dendritic cells (DCs) cultured in the presence of c-di-GMP showed increased expression of costimulatory molecules CD80/CD86 and maturation marker CD83, increased MHC-II and cytokines and chemokines such as IL-12, IFN-gamma, IL-8, MCP-1, IP-10 and RANTES, and altered expression of chemokine receptors including CCR1, CCR7 and CXCR4. c-di-GMP-matured DCs demonstrated enhanced T cell stimulatory activity. c-di-GMP activated p38 MAPK in human DCs and pERK in human macrophages. c-di-GMP is stable in human serum. It is proposed that c-di-GMP can be used clinically in humans and animals as an immune enhancer, immunotherapeutic, immunoprophylactic, or vaccine adjuvant.

Prophylactic pre-treatment of Mice With c-di-GMP Inhibits Infection In Vivo

The well-characterized mouse model of S. aureus-induced mastitis (see Brouillette et al., 2005 for review) was used to evaluate the capacity of c-di-GMP to act as a prophylactic agent. S. aureus is a Gram-positive bacterial pathogen. The protocol used here is similar to that described in a previous study (Brouillette et al., 2005), except that the c-di-GMP molecule was administered before infection of mammary glands, instead of after, in order to evaluate its prophylactic capacity. Briefly, 12- and 6 h before bacterial inoculation, saline, 50, or 200 nanomoles (nmol) of c-di-GMP was administered into the fourth pair of abdominal mammary glands of lactating CD-1 mice. Administration of 50 and 200 nmol of c-di-GMP corresponded to a dose of 1.0 and 4.1 mg of compound per kg of body weight, respectively, considering an average weight of 35 g for a mouse. For inoculation, 100 cfu of S. aureus Newbould 305 (ATCC 29740) were injected in each gland and the colonization allowed for 10 h. Raw bacterial cfu counts obtained after plating serial logarithmic dilutions of mammary gland homogenates were transformed in base-10 logarithm values. The experiment was repeated and data combined for a total of 9 mice (18 glands) per group. Since values passed the normality test, bacterial counts were analyzed for statistical significance using the One-way analysis of variance test combined with the Tukey post test (GraphPad Instat, version 3.06). The institutional ethics committee on animal experimentation of the Faculté des sciences of Université de Sherbrooke approved these experiments and were carried out following the guidelines of the Canadian Council on Animal Care.

Figure 6:
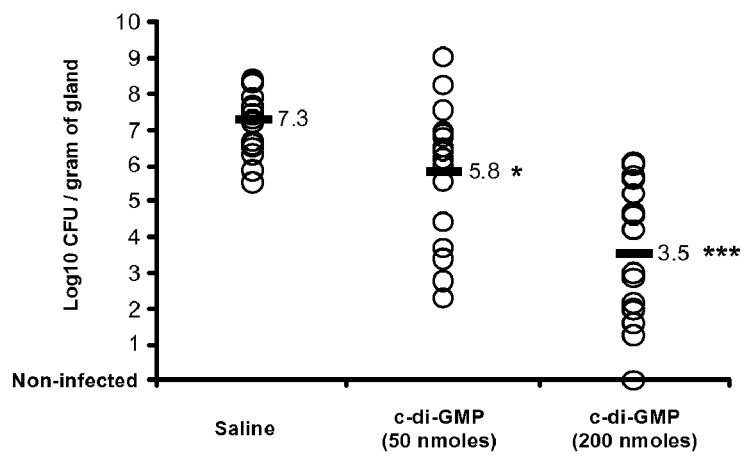
FIG. 6 is a graph showing pre-treatment protective effect of c-di-GMP. c-di-GMP was administered 12 and 6 h before infection with *S. aureus*. Lactating mice were infected by intramammary inoculation and the infection was allowed for 10 h before mammary glands were harvested for bacterial CFU determination. Each circle on the graph corresponds to the number of CFU per gram of gland for an individual gland. Mean values are indicated and show that prophylaxis with c-di-GMP significantly reduced the level of *S. aureus* colonization in a dose-dependent manner (*, $P<0.05$; ***  $P<0.001$).

It was previously reported that intramammary injections of c-di-GMP significantly decreased the colonization of the mouse mammary glands by S. aureus when the cyclic dinucleotide was administered twice, at the time of the bacterial challenge and at 4 h post-inoculation (Brouillette et al., 2005). Here, whether c-di-GMP had any prophylactic effect when provided hours before the bacterial inoculation of the mouse mammary glands was further investigated. An in vivo study was first performed to address the following questions: is c-di-GMP stable in tissues at the site of infection and will c-di-GMP stimulate a host innate immune response? In this study, c-di-GMP was given −12 h and −6 h prior to bacterial challenge. Even though the mammary glands were full of milk at the time of injection with infectious bacteria, FIG. 6 shows that pre-treatment with c-di-GMP 12 h and 6 h prior to bacterial challenge produces a significant prophylactic effect with a 1.5 and 3.8-log (~10,000-fold) reduction of the mean bacterial CFU in tissues using a 50 and 200 nmol dose, respectively, compared to the untreated control ($P<0.05$ and $P<0.001$, respectively). Had c-di-GMP only inhibited biofilm formation, as previously shown in our in vitro (Karaolis et al., 2005) and in vivo models (Brouillette et al., 2005), such dramatically reduced numbers of bacterial cells between pre-treated and non-treated mice would not have been expected to be found. These results suggest that c-di-GMP stimulates the innate immune response.

In the current study, pretreatment of mice with c-di-GMP was demonstrated to have a significant protective and prophylactic effect against S. aureus infection when c-di-GMP was administered 12-and 6 hours prior to bacterial inoculation in the mouse mammary glands. S. aureus infections such as bovine mastitis are difficult to treat and relapsing infections frequently occur (Gruet et al., 2001). The ability of S. aureus to enter and survive in phagocytic and non-phagocytic cells has been recognized and often correlates with the high frequency of relapse after antimicrobial therapy (Ferens et al., 2000; Lowy et al., 2000; and Brouillette et al., 2004).

The inhibition against experimental S. aureus infection in mice clearly establishes a general clinical use for the protective effect of c-di-GMP against infection (prevention). Since c-di-GMP targets the host immune response, these molecules would avoid drug resistance and also would be protected from most of the bacterial resistance mechanisms found in microorganisms that affect specific classes of antibiotics. It is proposed that cyclic dinucleotides, such as c-di-GMP, represent a new class of immunotherapeutic molecule. Another use is for increasing the immunity status of individuals or a population either at known risk of developing disease in order to reduce infection ("metaphylaxis"), or during periods of known disease susceptibility or immune suppression ("immune restoration") such as AIDS, transplant and cancer patients.

c-di-GMP has Adjuvant Properties

To evaluate the capacity of c-di-GMP to increase antibody production in the mouse (adaptive immune response), the cyclic dinucleotide was used as adjuvant for vaccination with S. aureus ClfA recombinant protein (a surface adhesion protein of S. aureus binding fibrinogen), as previously done for ClfA alone without adjuvant (Brouillette et al., 2002). Two groups of eight CD-1 female mice were vaccinated intramuscularly with 100 μl of saline containing 25 μg of ClfA. For one of the groups, the solution injected also contained 200 nmol of c-di-GMP. A volume of 50 ul was then injected into both quadriceps. This procedure was repeated two weeks after, for a second injection. Twelve days later, i.e. 26 days after the initial injections, blood samples were taken and incubated at 35° C. for an hour to allow coagulation, and then centrifuged at 13,000 g for 10 min at 4° C. Sera were harvested and kept at −20° C. until tested. The institutional ethics committee on animal experimentation of the Faculté des sciences of Université de Sherbrooke approved these experiments and were carried out following the guidelines of the Canadian Council on Animal Care.

Enzyme-linked immunosorbant assays (ELISA) were used to determine the presence of IgG antibodies against the ClfA antigen in the mouse serum, as previously described (Brouillette et al., 2002). Polystyrene Maxisorp 96-well plates (Nalge-Nunc International) were coated for 2 h with 50 μl of recombinant ClfA (domaine A) protein at a concentration of 10 μg/ml in carbonate/bicarbonate buffer at pH 9.6. Following saturation of the wells with a solution of powdered milk in PBS (5% w/v), overnight at 4° C., four-fold dilutions of sera (1/1000 to 1/64000) were added and incubated for 2 h at 35° C. and then overnight at 4° C. Biotinylated anti-mouse IgG (1/1000) was added and incubated for 2 h at 35° C. After 1 h of incubation with streptavidin-HRP (Amersham Pharmacia Biotech) diluted 1/500, 100 μl of Sure Blue TMB Peroxidase Substrate (KPL) was added. The enzyme reaction was stopped by the addition of 50 μl of 1N HCl after 6 min of incubation. Between each step, three washes with PBS-Tween 0.05% were carried out. The optical density (OD) was read on a plate reader (Bio-Tek Instruments) at 450 nm. Each sample was tested in triplicate and the OD of the negative control wells that did not contain antigen was subtracted from the ClfA-coated test wells.

ELISA assays were carried out as for the total IgG assay but the secondary antibody was either mouse anti-IgG1-HRP or mouse anti-IgG2a-HRP (BD Pharmingen) and four-fold dilutions of sera form 1/250 to 1/16000 were assayed. Quantitation of mouse antibodies was achieved as for the total IgG assay but the development of coloration was allowed for 10 min. Each sample was tested in triplicate and the OD of the negative control wells that did not contain antigen was subtracted from the ClfA-coated test wells. For the statistical analysis of ELISA results, the O.D. data for mice vaccinated with the c-di-GMP molecule as adjuvant were matched up to the corresponding data (isotype and dilution) where mice were injected with saline instead of c-di-GMP. One way analysis of variance (ANOVA) was used with the Bonferroni post-hoc test to account for multiple comparisons (Graphpad InStat software, version 3.06). For all isotypes and dilutions analyzed, statistical significance was found to be P<0.001 between the groups.

Based on in vivo results suggesting that c-di-GMP stimulates the host response and inhibits infection, additional experiments to address basic fundamental questions on the effects of c-di-GMP on the host immune response were performed. In order to evaluate the possibility that c-di-GMP could also act as an adjuvant, the cyclic dinucleotide was co-injected into mice with the recombinant ClfA antigen, a surface adhesion protein of $S.$ $aureus$ (Mc Devitt et al., 1997). Following vaccination with two intramuscular injections of a mixture of ClfA and c-di-GMP, serum samples analyzed 12 days after the last injection (i.e. day 26) showed significantly higher anti-ClfA IgG antibody titers (P<0.001) compared with injections of ClfA alone (FIG. 7). ELISA assays showed optical densities for total IgG and for the IgG1 and IgG2a isotypes that were above or around 0.5 at serum dilutions of 1/64000 and 1/16000, respectively, for the c-di-GMP treated group, whereas optical densities were below 0.5 for serum dilutions greater than 1/1000 for the group vaccinated with ClfA without c-di-GMP (FIG. 7D). In FIG. 7C and 7D, for each particular type of antibody assay and dilution tested, O.D. results for mice injected with c-di-GMP versus saline are statistically different from each other (P<0.001), as found by one way analysis of variance used in conjunction with the Bonferroni post-hoc test. Thus, in terms of optical density values at a serum dilution of 1/1000, c-di-GMP co-injection increased total IgG by 7.7 times, IgG1 by 3.6 times and IgG2a by 208.9 times (FIG. 7B). The relative increase in production of IgG2a in the presence of c-di-GMP may indicate an activation of the Th1 pathway. Although these experiments cannot confirm that without testing antigen-specific cytokine production, some of the other results indicate a similar tendency. In any case, the data clearly demonstrates that cyclic dinucleotides like c-di-GMP improve antibody production and augments the adaptive immune response.

To date it has been difficult to develop a highly protective vaccine for $S.$ $aureus$ (Lee, 1996; and Michie, 2002) and no vaccine that generates both humoral and cell-mediated responses that would be adequate for intracellular pathogens (Halpern et al., 1996; Portnoy, 1992; and Elkins et al., 1999) is available, although DNA-based vaccines are promising (Shkreta et al., 2004). Not only does c-di-GMP have a protective effect against $S.$ $aureus$ infection, but when given together with an antigen as part of a vaccine strategy, c-di-GMP promotes an antigen-specific immune response (adjuvant effect). This immunostimulatory effect is perhaps largely due to the capability of c-di-GMP to induce phenotypic and functional maturation/activation of myeloid DCs, but not pDCs.

In human and animal vaccine development, a major drawback to the development of novel vaccines has been the lack of safe, yet effective adjuvants. For example, biphasic lipid vesicles have been proposed for the delivery of oligo/polynucleotides (Alcon et al., 2006). The demonstration that c-di-GMP acted as an effective adjuvant for vaccination with $S.$ $aureus$ ClfA antigen when co-injected intramuscularly indicates good bioavailability without the requirement of specific delivery systems or formulations.

c-di-GMP Activates Monocyte and Granulocyte Recruitment In Vivo

C57BL/6 mice were injected with a volume of 500 ul containing 200 nmol c-di-GMP. Cervical dislocation was performed after 12 hours after which with 10 ml of cold PBS was injected and the fluid withdrawn and centrifuged at 1,400 rpm at 4° C. Fluid was incubated in PBS BSA azide +24G2 (anti Fc) for 15 min at 4° C., washed in PBS, washed in PBS then stained and analyzed by FACs analysis (PBS BSA azide, 30 min 4° C.). Cells were stained with directly coupled fluorescent mAbs combinations in 200 ml FACS buffer and further collected on a FACScalibur cytofluorometer (Becton Dickinson, BD). The following mAbs were purchased: fluorescein (FITC)-coupled M1/70 (anti-CD11b, BD Pharmingen), phycoerythrin (PE)-coupled 1A8 (anti-LY-6G, BD Pharmingen), 7/4 (Caltag), allophycocyanin (APC)-coupled F4/80 (Caltag). Cells were gated according to size and scatter to eliminate dead cells and debris from analysis.

In support of the immunomostimulatory activity mediated by c-di-GMP, studies in naive mice injected intraperitoneally (IP) with c-di-GMP shows that c-di-GMP induced the recruitment of $F4/80^{high}$ $LY$-$6G^{med}$ (monocytes) and $F4/80^{med}$ $LY$-$6G^{high}$ (granulocytes). FIG. 4 shows the results of studies in which FACS analysis using F4/80, LY-6G and CD11b antibody was used to identify monocytes and granulocytes in peritoneal lavage at 18 hours following intraperitoneal injection with 200 nmol c-di-GMP and 50 µg of LPS (positive control). The in vivo recruitment of monocytes and granulocytes into the peritoneal cavity in response to c-di-GMP is likely the outcome of local induction of certain chemokines (such as MCP-1) and the enhancement of adhesion molecules on either monocytes or endothelial cells. C-di-GMP also activated macrophage and granulocyte recruitment in vivo to a greater extent than CpG ODN and LPS under the conditions tested.

Although the results show that DC release MCP-1 in response to c-di-GMP, it is not believed that DC-derived MCP-1 is recruiting monocytes since MCP-1 release from activated macrophages is a more natural occurrence. The data suggests that c-di-GMP activates macrophages and granulocytes in vivo to a greater level than CpG and LPS at the concentrations tested. As the data suggested that intraperitoneal injection of c-di-GMP can activate monocytes and granulocyte recruitment, it is proposed that c-di-GMP activates resident peritoneal macrophages to produce or release monocyte chemoattractants, such as MCP-1.

c-diGMP Matures and Activates Murine and Human DCs

Murine splenic DCs were isolated from spleens of C57BL/6 mice. Briefly, spleens were dissected into small pieces and incubated at 37° C. in complete RPMI 1640. Cell suspension was obtained by vigorous pipetting and passage through a 70-uM nylon mesh filter. After red blood cell lysis, CD11c+ DCs were isolated using CD11c microbeads according to the manufacturer's instructions (Miltenyi Biotec). The cells were >95% CD11c+ as measured by FACS analysis. Murine IL-8 and TNF protein levels in the DC culture supernatant were measured by sandwich ELISA (R&D Systems).

Preparation and Treatment of Human Monocyte-Dendritic Cells (DCs)-Cytokine, Chemokine and Chemokine Receptor Analysis Buffy coats were obtained from healthy human volunteers and fractionated over Histopaque-1077. The peripheral blood mononuclear cells (PBMC) layer was recovered and erythrocyte-depleted by incubation in red blood cell lysis buffer for 5 minutes at room temperature. PBMCs were cultured in complete medium (RPMI 1640, 1% L-glutamine, 1% penicillin/streptomycin, and 10% low endotoxin FCS) for 2 hours in T75 flasks (Corning). Following incubation, nonadherent cells were removed by three washes with 1× PBS (Invitrogen, Carlsbad, Calif.). The remaining adherent cells were then cultured in complete medium supplemented with GM-CSF and IL-4 (50 ng/mL each). Human and murine IL-4 and GM-CSF were purchased from Peprotech (Rocky Hill, N.J.). On day 2 and day 4, the DC cultures received an additional dose of GM-CSF and IL-4 (50 ng/mL each). On day 5, nonadherent DC were harvested by gentle pipetting, counted, and plated in fresh medium containing GM-CSF and IL-4 (50 ng/mL each). On Day 6, some DC were matured by addition of 100 ng/ml LPS or 10-400 µM c-di-GMP for 1-24 hours.

Surface expression of various markers was assessed using CellQuest analysis software on a FACScalibur (Becton-Dickinson) flow cytometer. Surface expression was determined using the following FITC- and PE-conjugated antibodies: CD86-FITC (Research Diagnostics), CCR7-PE (R&D Systems), CD80-FITC, CD83-FITC, HLA-DR-FITC (BD Pharmingen). The isotype control antibodies were used accordingly in all experiments and were purchased from Pharmingen. Human DC were incubated in 1% human AB serum/PBS and were incubated with rat anti-CD16/CD32 (BD Phamingen) to block non-specific binding. Total RNA was extracted using the RNeasy kit according to the manufacturer's protocol (Qiagen). Briefly, after DNase I (Invitrogen) treatment, 1 µg of total RNA from each sample was used as template for the reverse transcription reaction. 50 ul of cDNA was synthesized using Oligo(dT)15, random hexamers, and multiscribe reverse transcriptase (Applied Biosystems). All samples were reverse transcribed under the same conditions (25° C. for 10 minutes, 48° C. for 30 minutes) and from the same reverse transcription master mix in order to minimize differences in reverse transcription efficiency. All oligonucleotide primers for QPCR were designed using Primer Express software 1.0 (PE Biosystems) and synthesized by Invitrogen. The 25 ul QPCR reaction contains 2 ul of cDNA, 12.5 ul of 2× SYBR Green master mix (Stratagene), and 250 nmol of sense and anti-sense primer. The reaction conditions were as follows: 50° C. for 2 minutes, 95° C. for 10 minutes then 40 cycles of 95° C. for 15 seconds and 60° C. for 1 minute. Emitted fluorescence for each reaction was measured during the annealing/extension phase, and amplification plots were analyzed using the MX4000 software version 3.0 (Stratagene). Quantity values (i.e., copies) for gene expression were generated by comparison of the fluorescence generated by each sample with standard curves of known quantities. Next, the calculated number of copies was divided by the number of copies of the housekeeping gene GAPDH.

Figure 9A:
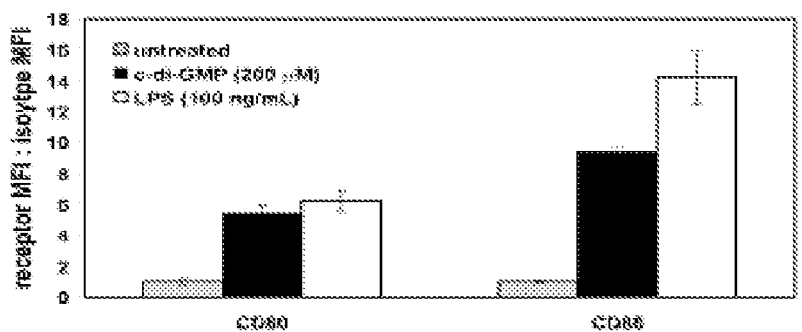
FIGS. 9A-9C are graphs showing that c-di-GMP activates murine DCs.
Figure 9B:
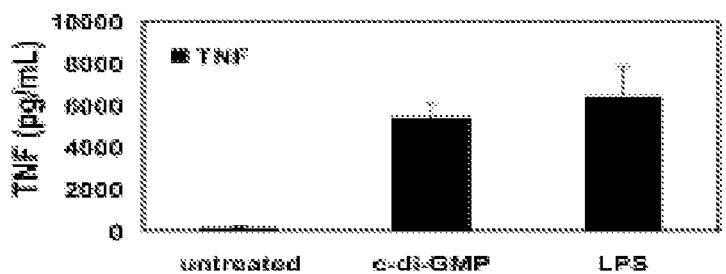
Figure 9C:
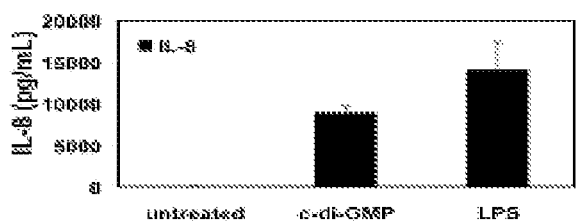

It was decided to test whether c-di-GMP could induce maturation of DCs. DCs are central in the immune response as they sense infection and respond appropriately in order to induce T cell immunity and promote a Th1 immune response. Maturation of DCs and their ability to become potent antigen-presenting cells is critical for initiation of immune responses. Primary murine CD11c$^+$ DCs were isolated from the spleen of C57BL/6 mice and treated with 200 uM c-di-GMP for 24 h. An increase in the surface expression of the co-stimulatory molecules CD80 and CD86 was observed (FIG. 9A). LPS-treated DCs were used as a positive control in this study and also induced a mature phenotype. To test whether c-di-GMP could induce the production of proinflammatory cytokines and chemokines, the supernatants of c-di-GMP treated DCs were analyzed. An increase in TNF and IL-8 protein in the supernatant of c-di-GMP treated murine DCs was observed (FIGS. 9B and 9C).

Figures 10A, 10B:
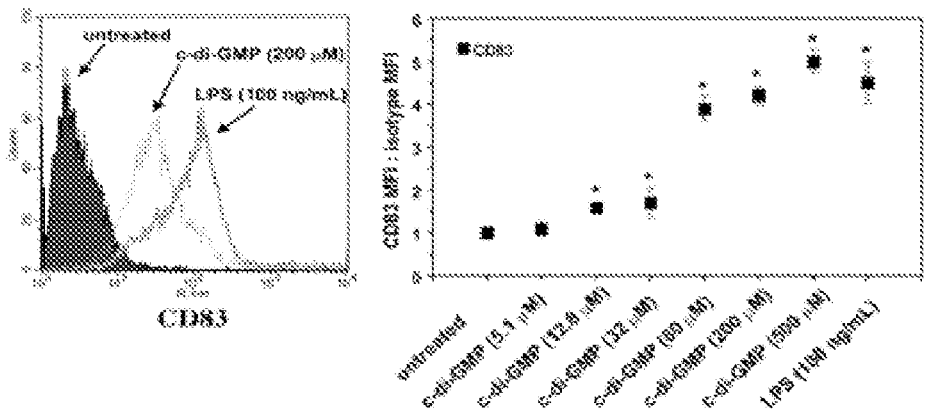
FIGS. 10A-10C show that c-di-GMP activates the maturation of human DCs.
Figure 10C:
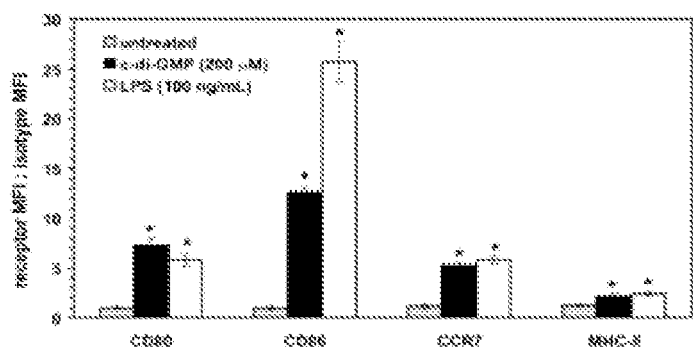

It was decided to also test whether c-di-GMP could induce the maturation and activation of human DCs. An in vitro culture system was used for the production of human monocyte-derived DCs in which adherent human monocyte-derived DCs prepared from adherent PBMCs cultured in IL-4 and GM-CSF for 5 days were used in these experiments. Immature DCs (defined by FAC analysis in which DCs expression no CD14 or CD83, but high levels of CD11c) were treated for 24 hours with 5 to 500 uM c-di-GMP. FIG. 10A shows a representative histogram comparing the increased expression of CD83 in DC treated with 200 uM c-di-GMP (net MFI=63.34) compared to that of untreated cells (net MFI=4.89) or cells treated with LPS (net MFI=141.22) used as negative and positive controls, respectively. A dose-dependent increase in surface CD83 expression was observed on cells treated with a wide-range of c-di-GMP concentrations, with significant increases beginning at 32 uM, and spiking at 500 mM -the highest concentration tested (FIG. 10B). An increase in the expression of other maturation markers (CD80, CD86, CCR7, and MHC class II) on DC treated with 200 uM c-di-GMP was also observed (FIG. 10C).

Figure 11A:
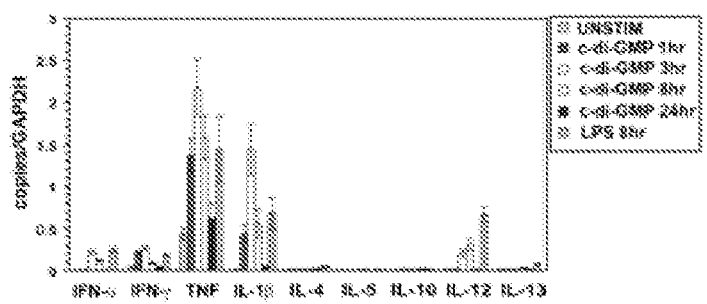
FIGS. 11A-11C are graphs showing cyokine, chemokine, and chemokine receptor expression during c-di-GMP-induced DC maturation. Expression of cytokines (A), chemokines (B), and chemokine receptors (C) were quantified by QPCR. Total RNA was extracted from 100,000 cells stimulated with 200 uM c-di-GMP for 1, 3, 8, and 24 hours or 100 ng/mL LPS for 8 hours and the number of transcripts is normalized to the number of copies of GAPDH. Error bars indicate standard deviation of triplicate measurements.
Figure 11B:
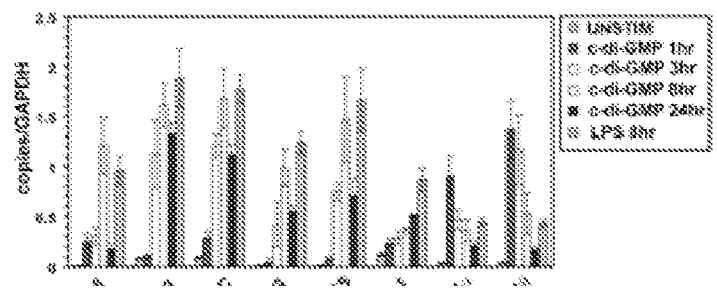

Cytokine, Chemokine and Chemokine Receptor Expression in c-di-GMP-Induced DC Maturation To examine the potential of c-di-GMP-treated DC in activating and/or recruiting other effector cells to sites of infection, we measured whether cytokine, chemokine, and chemokine receptor expression is altered in DC treated with c-di-GMP. FIG. 7B shows that treatment with c-di-GMP caused an increased mRNA expression of several chemokines in DC, notably IL-8/CXCL8, MIG/CXCL9, IP-10/CXCL10, I-TAC/CXCL11, MCP-1/CCL2, MIP-1a/CCL3, MIP-1b/CCL4, and RANTES/CCL5. In addition, c-di-GMP stimulated mRNA expression of the regulatory cytokine IFN-a, the proinflammatory cytokines IL-1b and TNF, as well as the TH1 cytokines IFN-g and IL-12 p40 (FIG. 11A). No evidence for the induction of Th2 cytokines (IL-4, IL-5, IL-10, IL-13) by c-di-GMP treated human DCs was found. To demonstrate that increases in IL-8 and IP-10 mRNA levels were accompanied by protein production, ELISA was performed on the supernatants of DCs stimulated with c-di-GMP stimulated for 24 hours. These data were consistent with the mRNA results (data not shown).

Figure 11C:
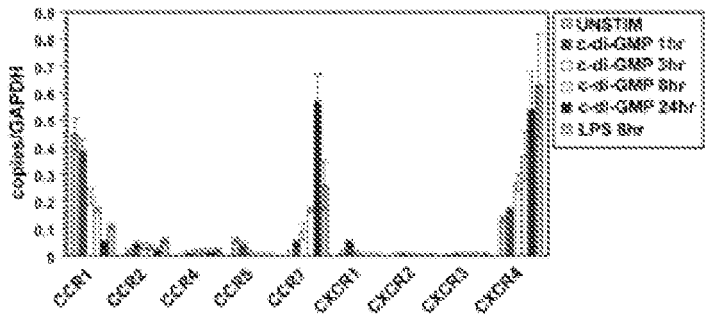

The migration of DCs from the periphery, where they encounter and take up foreign antigen, to the T cell area of the lymph nodes is an important aspect of immunity. To determine the potential c-di-GMP has in affecting DC trafficking, expression of chemokine receptors in cells stimulated with c-di-GMP was measured. The chemokine receptors CCR1 and CCR5 were found to be downregulated, while CXCR4 and the lymph node homing receptor CCR7 were upregulated on DCs following c-di-GMP treatment (FIG. 11C).

In order to rule out the possibility that the immunostimulatory effects of c-di-GMP was not due to the presence of LPS endotoxin contamination in the synthetic c-di-GMP preparation, a Limulus amebocyte lysate assay was performed. The highest dose of c-di-GMP (500 uM) used in the experiments were found not to contain LPS (<3 pg/mL LPS).

Consistent with an ability to act as an immunostimulator and immune enhancer, these results show that c-di-GMP stimulates both mouse and human DC maturation and differentiation, antigen-presenting capacity and enhanced T cell stimulatory activity, leading to an overall Th1 response. The immunostimulatory effect of c-di-GMP is more specific and not as overwhelming as that seen with LPS. Supporting an immune enhancer effect, it is known that IL-8 production results in enhanced migration of DCs and macrophages. These results suggest that TNF-a has a temporal pattern and peaks after 3 hours following c-di-GMP treatment then returns to a basal level after 24 hours. This is important as excessive and unchecked release of TNF-a can lead to tissue damage and sepsis. The ability of c-di-GMP to activate mouse and human DCs is consistent with the findings that pretreatment with c-di-GMP has a significant protective effect in the mouse model of mastitis and it has significant adjuvant properties when administered with an antigen.

c-di-GMP Enhances T Cell Stimulatory Activity

Another feature of DC maturation is an enhanced ability to stimulate T cells due to increased MHC and costimulatory receptor expression. Therefore, to determine whether c-di-GMP treated DCs have enhanced ability to stimulate T cells, a T cell proliferation assay was performed. Immature DCs, LPS-treated DCs, and c-di-GMP-treated DCs were co-cultured with T cells for 6 days, and allospecific T cell proliferation was measured by radiolabeled thymidine incorporation.

T-cell proliferation assay

Immature DC and c-di-GMP-treated DC were washed 3 times, diluted in fresh complete medium, and used as allogenic stimulators. Cells were seeded in 96-well round-bottom culture plates with APC serial dilutions ranging from 20,000 to 400 DC/well, and were mixed together with freshly purified CD3+ T cells (100,000/well). After 5 days of incubation, cells were pulsed with 1 uCi [$^3$H]-thymidine per well for 18 hours and were harvested on filter paper. Proliferative responses were measured as [$^3$H]-thymidine incorporation by an automatic beta-counter. Tests were performed in triplicates, and results were expressed as the mean count per minute (cpm).

Figure 12:
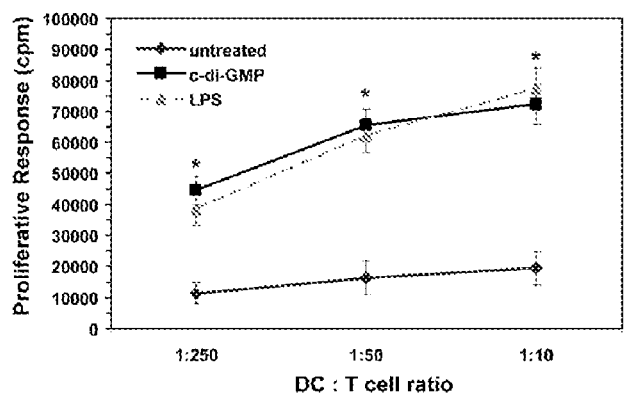
FIG. 12 is a graph showing c-di-GMP-matured DCs have enhanced T cell stimulatory activity in vitro. Immature DCs were stimulated with 200 µM for 24 hours. Purified T cells were then added to DCs at the ratio indicated and were allowed to incubate for an additional 5 days. On day 6, 1 uCi/well [$^3$H]thymidine was added and allowed to incubate for an additional 18 hours. T cell proliferation was measured by [$^3$H]thymidine uptake (cpm). *P<0.01, as determined by Student t test and error bars indicate standard deviation of triplicate measurements.

FIG. 12 shows that T cell proliferation was markedly upregulated (4 to 7 fold) in cocultures receiving DC pretreated with c-di-GMP, and this was identical to that seen in co-cultures receiving LPS stimulated DCs.

Effect on Human Plasmacytoid DCs

Since plasmacytoid DC represent a separate DC lineage compared to those of myeloid origin, it was tested whether c-di-GMP might also activate these cells for cytokine secretion, namely IFN-gamma secretion.

Preparation and Treatment of Human Plasmacytoid Dendritic Cells (pDC)

Venipuncture was performed on consenting adults using approved protocols. Plasmacytoid dendritic cells (pDCs) were prepared, as previously described (Schroeder et al., 2005), using a 2-step procedure involving Percoll density centrifugation followed with selection for Blood Dendritic Cell Antigen (BDCA)-4 positive cells (Miltenyi Biotec, Inc., Auburn, Calif.). The capacity of c-di-GMP to induce IFN-alpha from these cells was assessed using cell culture and ELISA protocols also previously described (Schroeder et al., 2005) and was simultaneously compared to the IFN-gamma produced by pDC in response to cells stimulated with CpG oligodeoxynucleotide (ODN)-2216 (Krieg, 2002).

In two independent experiments done in duplicate, c-di-GMP was negative for inducing this Type I IFN. In contrast, both pDC preparations produced IFN-gamma in response to stimulation with the Type A CpG oligo, ODN-2216 (data not shown).

c-di-GMP Activation of p38 MAPK in Human DCs

Human PBMC were isolated by Ficoll density gradient centrifugation from leukopacks supplied by the Department of Transfusion Medicine (Clinical Center, National Institute of Health, Bethesda, Md.). Monocytes were purified (>95%) from human PBMC with MACS CD14 monocyte isolation kit (Miltenyi Biotech Inc., Auburn, Calif.) according to the manufacturer's instruction. DCs were generated as described previously (Yang et al., 2001). In brief, DCs were generated by incubating purified monocytes at $2\times10^5$/ml in RPMI 1640 containing 10% FBS, 2 mM glutamine, 25 mM HEPES, 100 U/ml penicillin, 100 ug/ml streptomycin, 50 ng/ml recombinant human GM-CSF (PeproTech, Rocky Hill, N.J.), and 50 ng/ml recombinant human IL-4 (PeproTech) at 37° C. in a $CO_2$ (5%) incubator for 7 days. On day 3 and 5 of the incubation, half of the culture medium was replaced with pre-warmed (37° C.) fresh GM-CSF- and IL-4-containing medium. On day 7, DCs were collected, washed three times with PBS, and serum-starved for 8 hours by incubating in serum-free RPMI-1640 containing GM-CSF and IL-4 ($2\times10^5$/ml) at 37° C. in a $CO_2$ (5%) incubator. Subsequently, DCs ($2\times10^6$/sample) were incubated at 37° C. in the absence or presence of c-di-GMP or GMP (Sigma, St. Louis, Mo.) at concentrations specified for 5 or 30 minutes. At the end of incubation, the stimulation was immediately stopped by the addition of large amount of ice-cold PBS (10 folds). The cells were centrifuged at 1500 xg for 5 min at 4° C., washed with cold PBS and lysed by SDS sample buffer (62.5 mM Tris-HCl, pH 6.8 at 25° C., 2% w/v SDS, 10% glycerol, 50 mM dithiothretol, 0.01% bromophenol blue). The lysates were sonicated for 10 seconds to shear DNA, boiled for 5 min, and cooled down on ice.

The lysates were loaded (15 ul/lane) and separated on a 4-12% NuPAGE™ Bis-Tris Gel (Invitrogen, Carlsbad, Calif.) using 1× NuPAGE™ MES SDS Running Buffer (Invitrogen) as the electrode buffer. SeeBlue® Plus2 (Invitrogen) was used as molecular size marker. After electrophoresis, proteins in the gel were electrotransferred (25 V constant for 1 h) onto a piece of Immobilon™ membrane (Millipore, Bedford, Mass.) using 1× NuPAGE™ transfer buffer (Invitrogen). The membrane was sequentially washed, blocked for 1 h at room temperature, washed, and incubated at 4° C. overnight in the presence of 1:1000 dilution of rabbit anti-phospho-p38 MAPK antibody (Cell Signaling technology, Beverly, Mass.). On the next day, the membrane was washed and incubated with 1:2000 dilution of HPR-conjugated anti-rabbit IgG (Cell Signaling technology) for 1 h. After washing, and incubation with a working solution of ECL Plus Western Blotting Detection System (Amersham, Piscataway, N.J.) for 5 min at room temperature, the membrane was exposed to a piece of BioMax™ X-ray film (Kodak, Rochester, N.Y.). The X-ray film was developed using an automatic processor (Kodak X-OMAT 200A). The same membrane was stripped and probed for p38 MAPK protein essentially in the same manner except using rabbit anti-p38 antibody (Cell Signaling technology) as the primary antibody.

Figure 13A:
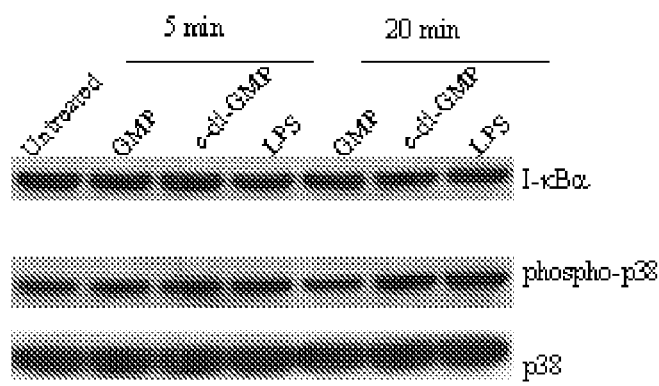
FIGS. 13A and 13B are gels showing that c-di-GMP induces signaling in DCs and macrophages.

To determine if c-di-GMP could activate intracellular signaling, the effect of c-di-GMP on the activation of p38 MAPK was investigated. As shown in FIG. 13A below, c-di-GMP did not activate NF-κB (since it did not activate I-κBα degradation), but activated p38 MAPK (as indicated by the increase in the phosphor-p38 at both 5 and 20 min treatment). LPS and GMP were used as positive and negative controls, respectively. In addition, c-di-GMP did not activate either ERK (data not shown). Since TNF expression is regulated by NF-κB and only up to 30 min after the addition of c-di-GMP was examined, activation of NF-κB at some later time point cannot be ruled out. These results were reproduced in four independent experiments using different donor-derived dendritic cells pERK Signaling in Human Macrophages Preparation of macrophages was performed as previously described (Akagawa et al., 1996). Briefly, fully differentiated macrophages from human PBMC were isolated from leukapheresis preparations obtained by the Blood Bank, Clinical Center, National Institutes of Health, Bethesda, Md. The leukocyte-rich preparation was overlaid on Accu-prep in 50 ml tubes and the tubes were centrifuged at 800 × g for 20 min at room temperature. PBMC fractions were collected, washed once with PBS at room temperature and twice with complete medium at 4° C. and resuspended in the same medium. Monocytes were further purified by using iso-osmotic Percoll gradient (Amersham Biosciences). At this stage, the purity of monocytes was higher than 90%. One and half million cells were placed on a 12-well plate in 1.5 ml RPMI1640 containing 50 ng/ml human M-CSF. On day 4, 1 ml of the medium was replaced with 1 ml of fresh medium containing 50 ng human M-CSF. On day 7, non-adherent cells were washed out and adherent cells were used as macrophages.

Western blot analysis of macrophages was performed as previously described (Matsuyama et al., 2003). Briefly, prepared macrophages were starved in RPMI 1640 without FCS for 10 h. Cells were rinsed three times with PBS, and treated with cyclic dinucleotide for various times. Cells were lysed on ice for 20 min in a buffer containing 50 mM NaCl, 20 mM Tris-HCl, 50 mM sodium fluoride, 30 mM Na4P2O7, 5 mM EGTA, 3 mM sodium orthovanadate, 1% Triton X-100, 1 mg/ml leupeptin, 1 mM PMSF, 1 mg/ml aprotinin, 1 mg/ml pepstatin A and 100 mM sodium orthovanadate pre-treated with H2O2. The lysates were spun in a microcentrifuge for 20 min and the supernatants were collected. Proteins were analyzed on 12% polyacrylamide gels by SDS-PAGE and transferred electrophoretically to nitrocellulose membranes at 150 mA for 1 h in a semi-dry system. The membranes were incubated with an antibody against either phosphorylated or nonphosphorylated p38 MAP kinase or ERK, followed by an appropriate secondary Ab coupled with horseradish peroxidase. Peroxidase activity was visualized using LumiGLO (Cell Signaling).

Figure 13B:
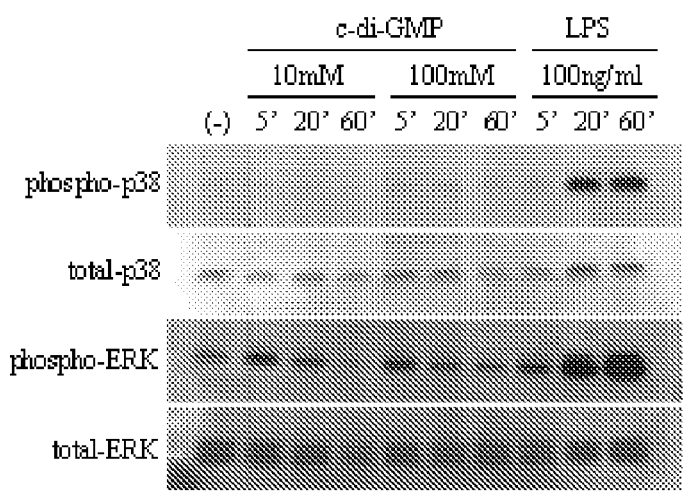

Based on three independent experiments, although there was no phosphorylation of p38 MAPK detected under the conditions tested, c-di-GMP (10- and 100 uM) was found to activate ERK phosphorylation in human M-CSF-induced monocyte-derived macrophages (FIG. 13B). The magnitude of c-di-GMP activation of ERK phosphorylation was weaker than that by LPS under the conditions tested. ERK phosphorylation peaked at 5 min and was absent at 20 min which was earlier than that compared to LPS-induced ERK phosphorylation.

Activation of the mitogen activated protein kinase (MAPK) pathways including p38, ERK and JNK are important for the differentiation/maturation of DCs and the NF-κB transcription factor is linked to the production of proinflammatory cytokines by DCs and has substantial impact on innate and adaptive immunity (Shkreta et al., 2004; Ardeshna et al., 2000; Bharadwaj et al., 2005; Lin et al., 2005; Boisleve et al., 2005; and Agrawal et al., 2004). The activation of p38 MAPK has been shown to play a critical role in the activation of DCs in response to a variety of stimuli (Arrighi et al., 2001; Puig-Kroger et al., 2001; Iijima et al., 2003; Yu et al., 2004; and Nakagawa eta l., 2004). In this study, the hypothesis that the action of c-di-GMP on the host immune response involves modulation of cell signaling pathways was tested. Since c-di-GMP did not activate ERK and JNK in DCs under the conditions tested, the exact mechanism by which c-di-GMP activates p38 MAPK awaits further investigation. However, the ability of c-di-GMP to activate p38 MAPK in DCs is consistent with its ability to induce the maturation of DCs, as evidenced by the upregulation of DC surface costimulatory molecules, cytokines chemokines and chemokine receptors, and its capacity to stimulate allogeneic MLR.

The results showing that mouse intraperitoneal injection of cyclic dinucleotide activates recruitment of monocytes and granulocyte recruitment suggested that c-di-GMP activated resident macrophages may produce and release monocyte chemoattractants, such as monocyte chemoattractant protein-1 (MCP-1/CCL2) (Yoshimura et al., 1996). MCP-1 plays a major role in the recruitment of monocytes into inflammatory sites and its production is dependent on activation of p38 MAPK (Goebeler et al., 1999; and Saccani et al., 2002). Based on the ability of c-di-GMP to activate monocytes and granulocyte in vivo, whether c-di-GMP could activate human monocyte-derived macrophages in vitro by evaluating the phosphorylation of two MAPKs, ERK and p38 MAPK in response to c-di-GMP was examined. However, although a transient phosphorylation of ERK in macrophages was detected, no obvious change in p38 MAPK phosphorylation in macrophages under the conditions tested was detected. One possible explanation for this difference is that macrophages (p38 MAPK is not induced) and DC (p38 MAPK is induced) respond differently to c-di-GMP. Since no effect on p38 MAPK was found in macrophages, these results suggest that the in vivo recruitment of monocytes and granulocytes macrophages by c-di-GMP does not result from production of MCP-1.

c-di-GMP-Induced Cell Activation is TLR-and Nod-Independent

It has been previously shown that lipopeptides, LPS, dsRNAs, flagellin, ssRNAs, and CpG DNA induce cellular activation via TLRs and that these pathogen-associated factors can induce DC maturation. Since various nucleotide structures have been shown to stimulate DCs through TLRS, it was hypothesized that c-di-GMP may also induce cellular activation through a TLR-dependent mechanism.

To test this hypothesis, human embryonic kidney (HEK) cells, which are normally unresponsive to TLR ligand stimulation, were stably transfected with TLR1/2, TLR3, TLR4/MD2, TLR5, TLR2/6, TLR7, TLR8, and TLR9. HEK 293 cells were cultured in Dulbecco's modified Eagle's medium supplemented with 10% fetal bovine serum. Cells were plated in 24-well tissue culture plates ($1 \times 10^5$ cells/well) and maintained in the above medium for 24 h. The following day, cells were either left untreated or incubated with the indicated amount of TLR ligand. After the 3 hour treatment period, cells were harvested for total RNA using the Qiagen RNeasy kit per the manufacturer's protocol. The total RNA was converted to cDNA and QPCR was performed to determine the number of copies of IL-8.

For Nod studies, experiments examining the synergistic activation of NF-kB by c-di-GMP in cells over-expressing Nod1 or Nod2 were carried out as previously described (Inohara et al., 2001). Briefly, HEK293T cells were transfected overnight with 30 ng of Nod1 or Nod2 plus 75 ng of IgB, luciferase reporter plasmid. Ten nanograms of a constitutive Renilla luciferase reporter was also transfected into cells to adjust for transfection efficiency. At the same time, 200 uM c-di-GMP, N-acetyl muramyl-L-Ala-γ-D-Glu-meso-DAP (M-triDAP; Nod1 ligand) or muramyl dipeptide (Nod2 ligand) were added and the synergistic NF-kB-dependent luciferase activation was then measured following 24h of co-incubation. NF-kB-dependent luciferase assays were based on two independent experiments performed in duplicate.

Figure 14:
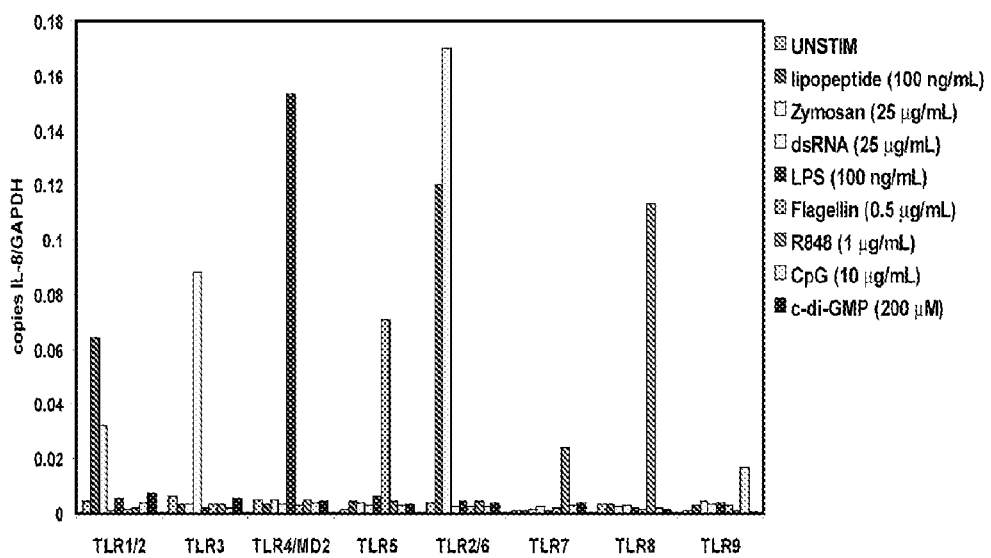
FIG. 14 is a graph showing that TLRs fail to confer response to c-di-GMP. HEK cells stably transfected with TLR proteins were stimulated for 3 hours with 200 uM c-di-GMP. Cells were harvested for RNA and IL-8 transcripts were quantified by QPCR.

As expected, these cell lines responded to TLR ligands according to their TLR expression profile (i.e., TLR3: dsRNA, TLR4/MD2: LPS), however, none of the TLR expressing cell lines were activated by c-di-GMP (FIG. 14). In addition to the earlier results showing no LPS contamination by the Limulus amebocyte lysate assay, by failing to confer TLR responsiveness to c-di-GMP (i.e., c-di-GMP failed to stimulate the LPS-sensitive MD2/TLR4-HEK cell line), the data confirm that the immune-enhancing activity of c-di-GMP is not due to any LPS contamination. Furthermore, neither Nod1 or Nod2 was found to respond to c-di-GMP (data not shown). These results suggest that c-di-GMP immunostimulation does not involve any known TLR or Nod.

One primary host mechanism for detection of pathogens or microbial products ("danger signals") is mediated by plasma membrane bound pathogen recognition receptors (PRRs) called Toll-like receptors (TLRs). TLRs interact with various microbe-associated molecules, and subsequent activation induces up-regulation of costimulatory molecule expression, production of antimicrobial effector molecules, and secretion of proinflammatory cytokines and chemokines. However, it is also possible that instead of innate immune signaling at the cell surface, signaling might occur in the cytosol in a TLR-independent manner. An emerging family of PRRs, called NODs (nucleotide-binding oligomerization domain) also appears to be involved in the recognition of bacterial products and can trigger an innate immune response. Nods are cytosolic proteins involved in innate immune defense, through pathways that are likely to be independent of TLR signaling. Although c-di-GMP is an immunostimulatory molecule derived from bacteria, the TLR and Nod tests suggest that immune activation does not appear to involve TLRs 1-9 or NODs 1-2. In addition, the pDC data also indicates that TLR9 is not likely involved. Therefore, while the exact receptor-mediated mechanism of c-di-GMP immune activation is not yet known, it does not act through any currently known TLR or NOD.

c-di-GMP is Stable in Human Serum

Commercially supplied pooled human serum (100 uL) (Cambrex Bio Science Walkersville, Inc.) was diluted in ion-exchanged water. An aliquot of the resulting human serum solution was subjected to HPLC analysis (conditions: COSMOSIL 5C18-AR-II column (4.6×200 mm); buffer A; buffer B, 80% acetonitrile in water; gradient, 0-10 min A 100%, 10-60 min A:B=100:0 to A:B=40:60 in 50 min; detection 254 nm, flow rate, 1.0 mL/min, temperature 40° C.). Separately, a 100 uM of c-di-GMP solution in human serum was prepared by adding 100 uL of a 500 uM c-di-GMP aqueous solution to a mixture of 390 uL of human serum and 10 uL of 40 mM 2-methylbenzimidazole (an internal standard for estimating the extent of decomposition of c-di-GMP) in methanol. An aliquot of the test solution was diluted immediately after the preparation solution and then heated at 100° C. for 5 min to quench activity of enzymes. The resulting test sample was subjected to HPLC analysis after 24 h treatment. Peaks that appeared in both analyses were compared. Results are based on 3 independent experiments.

HPLC analysis of the stability of c-di-GMP in human serum after 24 h at 37° C. showed only one eminent peak due to a nucleotide at the same retention time, which is identical with the retention time of monomeric c-di-GMP (data not shown). These results indicate that 100 uM c-di-GMP underwent no change in size and two-dimensional structure. Similar results were obtained with 500 uM c-di-GMP in which the ratio of the peaks due to c-di-GMP and the internal standard 2-methylbenzimidazole were ~100%, further indicating that no decomposition of c-di-GMP had taken place in human serum (data not shown). No peaks due to linear GpGp or pGpG and 5'-GMP were detected. The results of the HPLC analysis of human serum only (data not shown) show that three peaks were observed at $t_R$ (retention time) ca. 5, 20, and 50 min. However, these peaks did not overlap with those due to c-di-GMP and 2-benzimidazole used for the internal standard. The internal standard, 2-methylbenzimidazole was used because our data shows this compound is fairly soluble in water, methanol, and acetonitrile (solvents used for the preparation of the test solution and HPLC analysis), does not react with c-di-GMP, and is stable in human serum. Overall, these results suggest that c-di-GMP is stable in serum in addition to tissues (e.g., mammary gland).

If cyclic dinucleotides (like c-di-GMP) are to be used clinically, it is important to know their stability in vivo since serum might contain mammalian phosphodiesterases that could potentially cleave and degrade the molecule. The results clearly demonstrate that c-di-GMP is stable in pooled human serum and is an advantageous property for potential clinical use.

Due to its microbial origin and its effect on the host response, c-di-GMP can be considered as a "danger signal" or novel pathogen-associated molecular pattern (or PAMP). The findings with c-di-GMP have some features in common with other immunostimulatory molecules. Bacterial DNA containing unmethylated CpG motifs is also known to stimulate production of polyclonal Ig and Th1-associated immunomodulatory cytokines including IFN-γ, IL-12, and TNF-α, which provide some protection against intracellular pathogens (Halpern et al., 1996; Portnoy et al., 1992; and Elkins et al., 1999). CpG-containing oligodeoxynucleotides which act as TLR9 agonists, are recognized as adjuvants modulating mucosal immune responses (Cox et al., 2006). Like CpG, c-di-GMP itself can stimulate an immune response, however, the immunostimulatory ability of c-di-GMP is TLR-independent. The results show that c-di-GMP also enhances a Th1 response: i) pretreatment of mice with c-di-GMP inhibits bacterial infection; ii) c-di-GMP preferentially promotes the Ag-specific IgG2a over IgG1; ii) c-di-GMP upregulates IL-12, not IL-10; iii) c-di-GMP preferentially stimulates p38 MAPK in DCs.

A potential mechanism of action is that c-di-GMP may interact with a putative receptor, trigger an intracellular signal transduction cascade resulting in the up- and down-regulation of genes leading to the mobilization and activation of monocytes and granulocytes and DCs, and hence the inhibition of infection and enhancement of antigen-specific immune responses. The data does indicate the triggering of intracellular signal transduction cascades. While, the exact receptor (membrane or intracellular) c-di-GMP utilizes is currently under investigation, the data rule out the involvement of all known TLRs and Nods.

The findings from various in vivo models (infection, adjuvant and monocyte and granulocyte recruitment) using different routes of administration (intramammary, intramuscular and intraperitoneal) demonstrate that c-di-GMP molecule is an immunomodulatory (immunostimulatory) molecule triggering innate and adaptive immune responses. c-di-GMP augments the innate and adaptive immune response and has flexibility in its route of administration. Using in vitro models it was also shown that c-di-GMP activates human monocyte-derived DCs, acts like an adjuvant, and stimulates monocyte-derived DCs. It is proposed that c-di-GMP has broad activity and can be used clinically in humans and animals as an immune enhancer, immunotherapeutic, immunoprophylactic agent or vaccine adjuvant to inhibit infection and disease.

EXAMPLE 2

Use of Cyclic Dinucleotides to Inhibit Bacterial Pneumonia Caused by *Klebsiella pneumoniae*

To determine the effect of c-di-GMP pretreatment on survival in mice challenged with *K. pneumoniae* (a Gram-negative bacterial pathogen), female specific pathogen-free 6 to 8 week-old Balb/c mice were treated with c-di-GMP (200 nmoles) or vehicle i.n. or s.q. at both 48- and 24 hrs prior to the i.t. administration of *K. pneumoniae* ($5 \times 10^3$ CFU), then assessed for survival. The virulent *K. pneumoniae* strain 43816, serotype 2 (ATTC, Manassas, Va.) was used. For i.n. administration, c-di-GMP, the nucleotide control c-GMP, or vehicle (phosphate buffered saline (PBS)) was administered i.n. in a 10 ul volume. For i.t. administration of bacteria, the trachea was exposed, and 30 ul of inoculum was administered via a sterile 26-gauge needle. The skin incision was closed using surgical staples. Survival curves were compared using the log rank test.

Figure 15:
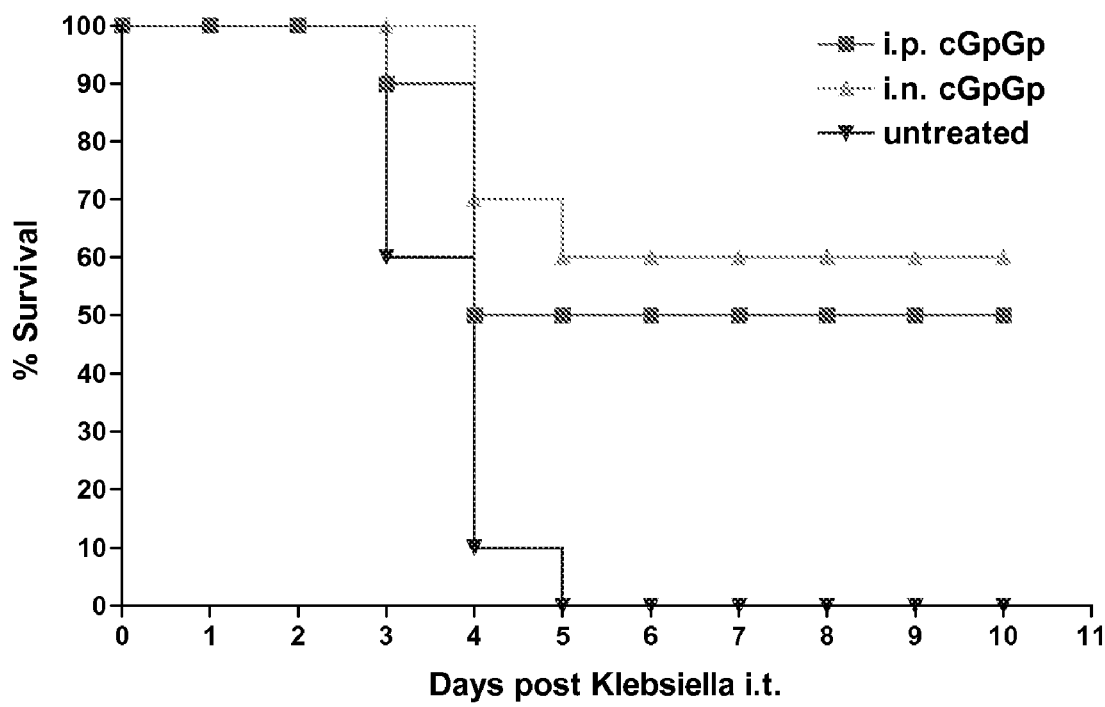
FIG. 15 is a graph showing survival following pretreatment with either i.n. or s.q. c-di-GMP in *Klebsiella*-infected animals. Animals were administered i.n. or s.q. c-di-GMP or vehicle (saline) control 48 and 24 h prior to days prior to i.t. *Klebsiella*, then assessed for survival through day 10 following infection. *p<0.05 by two-tailed log rank test compared to control *Klebsiella*-infected mice (10-11 animals per group; composite results from 2 separate experiments). % survival is shown on x-axis.

In previously published studies, it was shown that the maximal benefit of c-di-GMP was observed at an in-vivo dose of 200 nmoles/animal (Brouillette et al., 2005). In the current studies, *Klebsiella*-infected animals pretreated with vehicle only had a long term survival of approximately 10%. In contrast, survival of mice pretreated with c-di-GMP either locally (i.n.) or systemically (s.q.) was significantly increased at both early and late time points following i.t. *Klebsiella* challenge (FIG. 15, $p<0.05$), with the i.n. route of delivery being equally as efficacious as the s.q. route. Importantly, the survival benefits observed required pretreatment, as no increase in survival was observed in animals in which c-di-GMP administration was concomitantly given and 6 hrs post *K. pneumoniae* administration (data not shown).

c-di-GMP Pretreatment Improves Clearance of *K. pneumoniae* in a Mouse Model of Pneumonia Experiments were performed to determine if the beneficial effect of c-di-GMP was attributable to improved bacterial clearance and decreased dissemination. Because the survival benefits of c-di-GMP when given i.n. were equivalent to that observed with s.q. administration, subsequent studies were performed using the i.n. route of c-di-GMP delivery. In these studies, female specific pathogen-free 6 to 8 week-old Balb/c mice were pretreated with c-di-GMP (200 nmole) or control c-GMP i.n. at 48 and 24 hrs prior to i.t. *K. pneumoniae* ($5 \times 10^3$ CFU) challenge, then bacterial burden in lung and blood determined 48 hrs after bacterial challenge. The virulent *K. pneumoniae* strain 43816, serotype 2 (ATTC, Manassas, Va.) was used. At designated time points, the mice were euthanized by $CO_2$ inhalation. Prior to lung removal, the pulmonary vasculature was perfused by infusing 1 ml of PBS containing 5 mM EDTA into the right ventricle. Whole lungs were removed, taking care to dissect away lymph nodes. The lungs were then homogenized in 1 ml of PBS with protease inhibitor (Boehringer Mannheim, Indianapolis, Ind.). Homogenates were then serially diluted 1:5 in PBS and plated on blood agar to determine lung CFU. The remaining homogenates were sonicated, and then centrifuged at 1400 xg for 15 minutes. Supernatants were collected, passed through a 0.45 um-pore-sized filter, and then stored at $-20°$ C for assessment of cytokine levels. Blood was collected in a heparinized syringe from the right ventricle at designated time points, serially diluted 1:2 with PBS, and plated on blood agar to determine blood CFU.

Figure 16A:
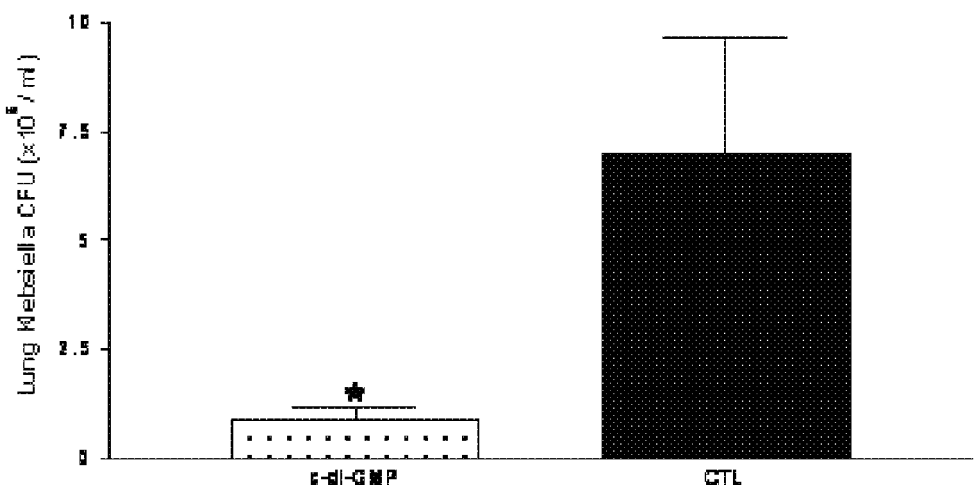
FIGS. 16A and 16B are graphs showing bacterial clearance of *K. pneumoniae* after i.n. pretreatment. Mice were administered i.n. c-di-GMP or saline control 48 and 24 hrs prior to days prior to i.t. *Klebsiella*, then *K. pneumoniae* determined in lung and blood 48 hrs later.
Figure 16B:
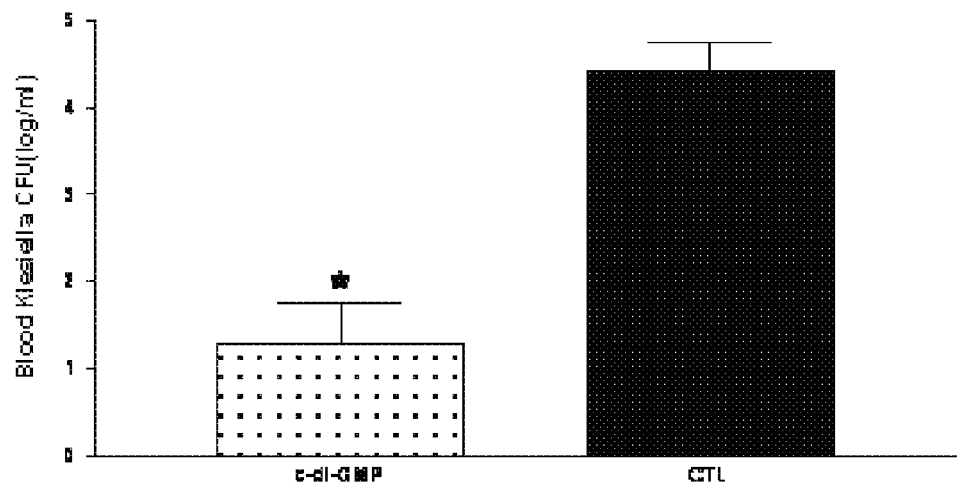

Intranasal pretreatment with c-di-GMP resulted in an approximately 5-fold reduction in *K. pneumoniae* CFU in lung at 48 hrs post infection ($p<0.05$, FIG. 16). More striking was the finding that i.n. pretreatment with c-di-GMP resulted in a greater than 1000-fold reduction in *K. pneumoniae* CFU in blood, as compared to that observed in control infected animals ($p<0.01$).

c-di-GMP Pretreatment Affects Lung Leukocyte Influx and Antibacterial Host Defenses in a Mouse Model of *Klebsiella pneumonia*

The question of whether pretreatment with c-di-GMP enhanced bacterial clearance in murine *Klebsiella pneumonia* by altering the influx and/or activation of cells required for effective antibacterial host defense was next determined. To address this, female specific pathogen-free 6 to 8 week-old Balb/c mice were administered either c-di-GMP or equal concentrations of nucleotide control (c-GMP) i.n. 48 and 24 hr prior to i.t. *K. pneumoniae* challenge, then lungs harvested 48 hr post infection and total leukocyte populations quantitated by lung digestion. The virulent *K. pneumoniae* strain 43816, serotype 2 (ATTC, Manassas, Va.) was used. The 48 hr time point was chosen, as near maximal influx of leukocytes was observed at this time point post *Klebsiella* administration. Total lung leukocytes were isolated as previously described (Deng et al., 2004; and Greenberger et al., 1996). Briefly, lung tissue was minced to a fine slurry in 15 ml of digestion buffer (RPMI, 5% fetal calf serum, collagenase 1 mg/ml (Boehringer-Mannheim, Chicago, Ill.), and DNase 30 ug/ml (Sigma, St. Louis, Mo.)). Lung slurries were enzymatically digested for 30 minutes at $37°$ C. Undigested fragments were further dispersed by drawing the solution up and down through the bore of a 10-ml syringe. The total lung cell suspension was pelleted, resuspended, and spun through a 20% Percoll gradient to enrich for leukocytes for flow analysis. Cell counts and viability were determined on a hemacytometer using Trypan blue exclusion. Cytocentrifugation slides (Cytospin 2; Shandon Inc., Pittsburgh, Pa.) were prepared from lung digest leukocyte suspensions and stained with Diff-Quik (Dade Behring, Newark, Del.) for cell differential. Statistical significance was determined using the unpaired t-test or ANOVA for multiple comparisons as appropriate As shown in Table 2, i.t. administration of *K. pneumoniae* resulted in an increase in the total number of leukocytes, especially neutrophils, in whole lung digest, as compared to uninfected controls. Importantly, animals pretreated with c-di-GMP had a significant increase in the total number of lung leukocytes ($p<0.01$), which was largely attributable to the striking 3-fold increase in the number of neutrophils in the lungs of infected mice ($p<0.01$), as compared to animals pretreated with PBS control.

TABLE 2

Effect of c-di-GMP on lung leukocyte accumulation.

| | Uninfected | c-di-GMP + kp | CTL + kp |
|---|---|---|---|
| Total number lung cells | $2.7 \times 10^7$ | $4.67 \times 10^{7*}$ | $3.57 \times 10^7$ |
| PMN | $0.8 \times 10^6$ | $22 \times 10^{6**}$ | $7.35 \times 10^6$ |
| Mono/Macrophage | $2.3 \times 10^7$ | $1.9 \times 10^7$ | $2.88 \times 10^7$ |
| DX5$^+$ (NK) | $1.3 \times 10^6$ | $3.8 \times 10^6$ | $2.5 \times 10^6$ |
| DX5$^+$, CD69$^+$ | $0.78 \times 10^5$ | $5.98 \times 10^{5**}$ | $2.7 \times 10^5$ |
| DX5$^+$, $\alpha\beta\gamma\delta$Tcr$^+$(NK T$^+$) | $1.6 \times 10^5$ | $6.8 \times 10^{5*}$ | $4.7 \times 10^5$ |
| $\alpha\beta$Tcr$^+$ | $2.6 \times 10^6$ | $5.5 \times 10^{6**}$ | $3.38 \times 10^6$ |
| $\alpha\beta$Tcr$^+$, CD69$^+$ | $0.33 \times 10^5$ | $3.7 \times 10^{5*}$ | $2.7 \times 10^5$ |

Leukocytes were quantitated in lung digests 48 hrs after *K. pneumoniae* (kp) administration.
*p, 0.05,
**$p < 0.01$ as compared to *Klebsiella*-infected mice pretreated with CTL (c-GMP) i.n. N = 3 for uninfected, n = 6 for CTL and c-di-GMP-treated groups.

To determine if c-di-GMP administration altered the influx and/or activation of selected T cell and NK cell populations, animals were pretreated with c-di-GMP or vehicle control 48- and 24 hr prior to *K. pneumoniae* challenge, then the presence of specific T and NK cell populations determined by flow cytometry 48 hrs post bacterial challenge. Cellular activation was determined by expression of the activational marker CD69. *Klebsiella* administration in vehicle-pretreated animals resulted in an increase in the total number of NK cells and NK cells expressing CD69. Pretreatment with c-di-GMP in infected mice resulted in a trend toward increased numbers of NK cells and a significant increase in the accumulation of NK cells expressing CD69 (Table 2). Moreover, an increase was observed in the number of NKT and αβ T cells in lungs of infected mice pretreated with c-di-GMP as compared to controls, as well as a significantly greater number of activated αβ T cells (as indicated by CD69 expression) in animals pretreated with c-di-GMP.

c-di-GMP Administration Modulates the Expression of Chemotactic and Activating Cytokines in Uninfected and *Klebsiella*-Infected Mice The previous experiments indicated that the intrapulmonary administration of c-di-GMP resulted in a significant increase in lung neutrophils, as well as an accumulation and/or activation of NK, NKT, and αβ T cell populations in mice infected with *K. pneumoniae*. To define the mechanism of enhanced neutrophil recruitment and selected NK and T cell accumulation/activation, the time dependent expression of TNF-α, the neutrophil chemotactic cytokine MIP-2, and the type 1 cytokines IL-12 p40, IFN-gamma, and IP-10 were assessed in the lungs of mice pre-treated with c-di-GMP or control c-GMP.

Whole lung was harvested at designated time points, immediately "snap frozen" in liquid nitrogen, and then stored at −70° C. for RNA extraction. Total cellular RNA was isolated from frozen lungs as described previously. Measurement of gene expression was performed utilizing the ABI Prism 7000 Sequence Detection System (Applied Biosystem, Foster City, Calif.) as previously described (Yoshida et al., 2001). Briefly, primer and probe were designed using Shortcut to Primer Express software (Applied Biosystems). The primers, placed in different exons, were tested not to amplify genomic DNA. Primers and probe nucleotide sequences for mIP-10 were as follow: forward primer 5'-CCA-GTG-AGA-ATG-AGG-GCC-ATA-3' (SEQ ID NO:1), reverse primer 5'-CTC-AAC-ACG-TGG-GCA-GGA-T-3' (SEQ ID NO:2), TaqMan probe 5'(FAM)-TTT GGG CAT CAT CTT CCT GGA-(TAMR)3' (SEQ ID NO:3); for mTNF-α, forward 5'-CAG CCG ATG GGT TGT ACC TT-3' (SEQ ID NO:4), reverse 5'-TGT GGG TGA GGA GCA CGT AGT-3' (SEQ ID NO:5), probe 5'-TCC CAG GTT CTC TTC AAG GGA CAA GGC-3' (SEQ ID NO:6); for mMIP-2, forward 5'-GAA CAT CCA GAG CTT GAG TGT GA-3' (SEQ ID NO:7), reverse 5'-CCT TGA GAG TGG CTA TGA CTT CTG T-3' (SEQ ID NO:8), probe 5'-CCC CCA GGA CCC CAC TGC G-3' (SEQ ID NO:9); for mIL-12 p40, forward 5'AGA CCC TGC CCA TTG AAC TG-3' (SEQ ID NO:10), reverse 5'-GAA GCT GGT GCT GTA GTT CTC ATA TT-3' (SEQ ID NO:11), probe 5'-CGT TGG AAG CAC GGC AGC AGA A-3' (SEQ ID NO:12), for mβ-actin: forward 5'-CCG-TGA-AAA-GAT-GAC-CCA-GAT-C-3' (SEQ ID NO:13), reverse 5'-CAC-AGC-CTG-GAT-GGC-TAC-GT-3' (SEQ ID NO:14), probe 5'-TTT-GAG-ACC-TTC-AAC-ACC-CCA-GCC-A-3' (SEQ ID NO:15). Specific thermal cycling parameters used with the TaqMan One-Step RT-PCR Master Mix Reagents kit included 30 min at 48° C., 10 min at 95° C., and 40 cycles involving denaturation at 95° C. for 15 s, annealing/extension at 60° C. for 1 min. Relative quantitation of cytokine mRNA levels was plotted as fold-change compared to untreated control lung. All experiments were performed in duplicate. Total lung leukocytes were isolated as described previously (Deng et al., 2004; and Yoshida et al., 2001). Using FITC or PE-labeled antibodies (BD PharMingen, San Diego, Calif.), isolated leukocytes were then stained with the following: anti-CD4, anti-CD8, anti-β-Tcr (αβ-T-cell marker), anti-γδ-Tcr (γδ-T-cell marker), anti-DX5 (NK cell marker), and anti-CD69 antibodies. In addition, cells were stained with anti-CD45-Tricolor (Caltag Laboratories, South San Francisco, Calif.) to distinguish leukocytes from non-leukocytes. Cells were collected on a FACSCalibur cytometer (Becton Dickinson, San Jose, Calif.) using CellQuest software (Becton Dickinson). NK cells and T-cell subsets were analyzed after gating on CD45+ lymphocyte-sized cells, and then examining for FL-1 and FL-2 fluorescence expression.

Figure 17A:
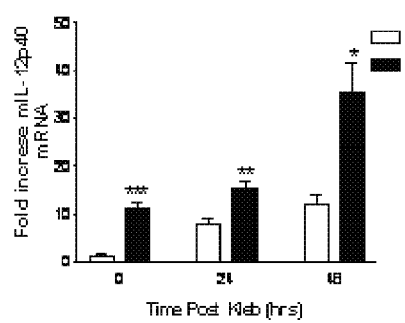
FIGS. 17A-17D are graphs showing cytokine mIL-12p40 (FIG. 17A), mIP-10 (FIG. 17B), mIFN-γ(FIG. 17C) and mIMIP-2 (FIG. 17D) mRNA levels in whole lung homogenates following i.t. *Klebsiella*. Mice were administered i.n. or s.q. c-di-GMP or control GMP 48 and 24 hrs prior to days prior to i.t. *Klebsiella*, then cytokine mRNA levels in lung homogenates determined at 0, 24, and 48 hrs post *K. pneumoniae* challenge by quantitative PCR. Values shown represent mean fold-increase over uninfected control mice and shown on x-axis. *, p<0.05, **p<0.01 compared to Ctl GMP-treated controls (4-5 animals per group).
Figure 17B:
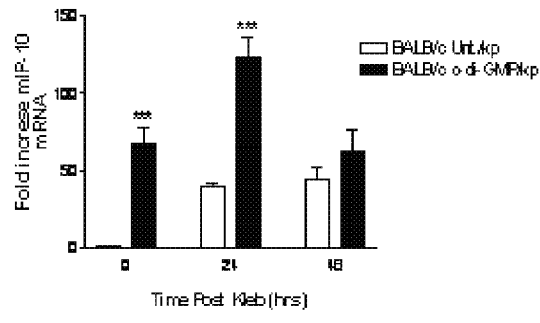
Figure 17C:
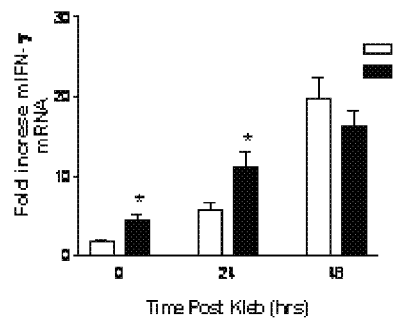
Figure 17D:
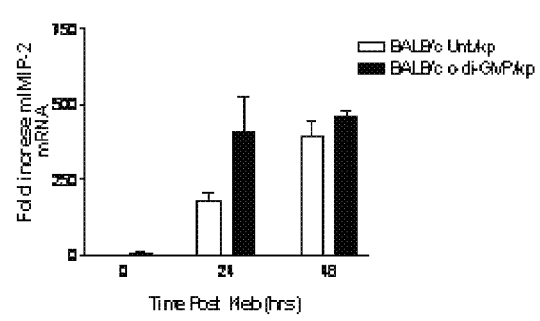

Pretreatment of mice with c-di-GMP did not significantly alter the induction of TNF-α in response to i.t. bacterial administration (data not shown). This is important as excessive and unchecked release of TNF-a can lead to tissue damage and sepsis. However, a significantly greater early induction of MIP-2 mRNA levels (at 24 hr post *Klebsiella* challenge) was observed, as compared to that observed in animals pretreated with c-GMP control (2-fold increase over infected control, FIG. 17D, $p<0.05$). In addition, pre-treatment with c-di-GMP i.n. resulted in induction of the type 1 cytokines IL-12 p40, IFN-gamma, and IP-10 in the lungs at time 0 (pre-infection). Moreover, IP-10 and IFN-gamma mRNA levels were significantly higher in c-di-GMP treated mice at 24 hrs post *K. pneumoniae* administration ($p<0.05$), whereas IL-12 p40 levels were increased at both 24 and 48 hrs post bacterial challenge, as compared to infected animals pretreated with control c-GMP.

Using a murine model of Gram-negative pneumonia, the local intranasal (i.n.) or systemic subcutaneous (s.q.) administration of c-di-GMP prior to intratracheal (i.t.) challenge with *Klebsiella pneumoniae* stimulates protective immunity against infection. Specifically, i.n. or s.q. administration of c-di-GMP (200 nmoles) 48- and 24 h prior to i.t. *K. pneumoniae* challenge resulted in increased survival, as compared to control animals pretreated with cGMP or saline. Pretreatment with c-di-GMP resulted in a 5-fold reduction in bacterial CFU in lung ($p<0.05$) and an impressive >1000-fold decrease in CFU in the blood ($p<0.01$) compared to control animals. c-di-GMP administration stimulated a robust innate response to bacterial challenge, characterized by enhanced accumulation of neutrophils, NKT cells, αβ T cells, as well as activated NK and αβ T lymphocytes, which was associated with earlier and more vigorous expression of macrophage inflammatory protein 2 (MIP-2), and type-1 cytokines and chemokines, including IL-12, IFN-gamma, and the IFN-gamma dependent ELR$^-$ CXC chemokines Interferon-gamma Inducible Protein-10 (IP-10). These findings demonstrate that c-di-GMP delivered in either a compartmentalized or systemic fashion stimulates protective innate immunity in the lung and protects mice against bacterial invasion.

In bacterial pneumonia, clearance of pathogens, especially virulent Gram-negative pathogens, is primarily dependent upon a vigorous innate immune response (Broug-Holub et al., 1997; Lipscomb et al., 1983; Toews et al., 1980; and Tsai et al., 2000). The present study clearly demonstrates that c-di-GMP administration enhances several key aspects of the cytokine-mediated innate immunity in the lung. In particular, c-di-GMP primes the host for enhanced early expression of MIP-2, a potent neutrophil-active chemokine that contributes to the recruitment of neutrophils in Gram-negative pneumonia. Moreover, c-di-GMP given i.n. directly stimulated the expression of type-1 cytokines/chemokines IL-12, IFN-gamma, and IP-10, and the expression of these cytokines was further enhanced during lung bacterial infection. This is of particular relevance as these cytokines are necessary for effective clearance of *K. pneumoniae* and other important bacterial pathogens from the lung (Greenberger et al., 1996; Zeng et al., 2005; and Yoshida et al., 2001). Collectively, the presence of these cytokines indicates that c-di-GMP functions as an immunostimulatory molecule that skews the immune system towards a type 1 phenotype, an effect which is clearly beneficial in host defenses against both intracellular and extracellular bacterial pathogens.

The cellular components of c-di-GMP-stimulated immunity have not been clearly defined in this model, but several candidate cell populations are likely involved. A more robust early influx of neutrophils in c-di-GMP pretreated animals post bacterial challenge was observed. Neutrophils represent an important phagocytic cell in the clearance of bacterial pathogens from the lung (Lipscomb et al., 1983; and Tsai et al., 2000). The c-di-GMP-induced upregulation of MIP-2 may contribute to increased neutrophil trafficking. Moreover NK, NKT and αβ T cells are cell populations that play an important role in innate immunity. For instance, NK cells are considered to be the primary source of IFN-gamma in the lung early in the course of bacterial infection (Deng et al., 2001; and Ferlazzo et al., 2003). Furthermore, NKT cells can be primed to secrete prodigious quantities of IFN-gamma in the setting of infection (Gonzalez-Aseguinolaza et al., 2000; Kawakami et al., 2001; and Taniguchi et al., 2003), and these cells have been shown to contribute to innate immunity against pulmonary *Streptococcus pneumoniae* challenge (Kawakami et al., 2003). Importantly, increased numbers of αβ-T-cells and NKT cells, as well as enhanced activation of NK and αβ T cells was found in the lungs of *Klebsiella*-infected animals pretreated with c-di-GMP, as compared to animals pretreated with control nucleotide. The accumulation and/or activation of these cell populations in the lungs of c-di-GMP -pretreated animals may be partially attributable to the enhanced expression of IP-10, which is a chemoattractant for these cells in vivo and in vitro (Ferrero et al., 2003; Johnston et al., 2003; and Romagnani et al., 2001). Thus, the recruitment and/or activation of several key immune cell populations likely contribute to improved bacterial clearance and outcome in animals pretreated with c-di-GMP.

The promotion of enhanced type 1 immunity in response to c-di-GMP administration supports the distinct possibility that c-di-GMP directly stimulates DC mediated responses. In fact, it was shown in Example 1 that c-di-GMP pretreatment has a protective effect and can inhibit bacterial infection in vivo, promote antigen-specific antibody responses (adjuvant effect), and that treatment of human monocyte-derived DC in vitro with c-di-GMP significantly induces DC cytokine and chemokine production and increases the cell-surface expression of maturation markers, including CD80, CD86, CCR7, and MHC class II. In addition, that study also showed that stimulation of human DC by c-di-GMP was associated with activation of p38 MAPK. The finding of enhanced IL-12 p40 expression in response to c-di-GMP is consistent with DC activation in the lung, although cells other than DC may also contribute to enhanced IL-12 expression, including lung macrophages. Notably, the i.n. administration of c-di-GMP did not alter trafficking of myeloid or plasmacytoid DC to the lung in response to bacterial challenge, nor did it change the expression of co-stimulatory molecules (CD40, CD80, or CD86) by lung myeloid DC (data not shown).

Consistent with the in vivo and in vitro findings, chemically synthesized c-di-GMP, a bacterial derived intracellular signaling molecule, is demonstrated to be an immunostimulator and can stimulate multiple aspects of innate immunity. Based on recent and current findings, uses for c-di-GMP in humans (and animals) include immmunoprophylaxis and as an adjuvant, as well as for increasing the immunity status of individuals or a population either at known risk of developing disease in order to reduce infection ("metaphylaxis"), or during periods of known disease susceptibility or immune suppression ("immune restoration") such cancer, AIDS, transplants, post-surgical and trauma patients. c-di-GMP treatment and its broad range of administration (oral, intransal, i.p, i.m., i.v, s.q) play a beneficial role in immunoprophylaxis as a general immune enhancer by activating innate host defenses in humans with pneumonia or in those who are at high-risk for the development of pneumonia.

EXAMPLE 3

Use of Cyclic Dinucleotides (e.g. c-di-GMP) to Inhibit *Francisella tularensis* Infection

*Francisella tularensis* is a Gram-negative bacterial pathogen and the cause of tularemia. An attenuated live vaccine strain, *F. tularensis* LVS, was developed almost 50 years ago, and remains the sole prophylactic against virulent strains of the pathogen. Two subspecies (type A and B strains) of the pathogen exist, the former being much more virulent than the latter for humans and other higher mammals. *F. tularensis* is an extremely virulent facultative intracellular bacterial pathogen of many mammalian species including mice and humans. In humans, intradermal or inhaled inocula of 10 cfu or less of the most virulent strains of the pathogen are sufficient to cause severe infection and possible death; in mice similar inocula are routinely lethal.

Using *F. tularensis* LVS as a model vaccine, it is possible to systemically immunize various mouse strains and protect them against subsequent massive (2000 cfu) intradermal (i.d.) challenge, but not against low dose (approximately 10 cfu) aerosol challenge, with virulent strains of the pathogen. This is troubling because the latter route is considered an important means of deliberately disseminating *F. tularensis* in a bioterrorist attack. Administering LVS to humans, guinea pigs and monkeys as an aerosol enhances protection against subsequent aerosol challenge with virulent *F. tularensis*.

In a mouse model of tularemia, interferon gamma (IFN-gamma) and CD4+ and CD8+ T cells are essential for the expression of anti-*Francisella* immunity in the lungs and limiting dissemination of the pathogen to internal organs. Early recruitment of inflammatory cells and production of proinflammatory cytokines (such as IFN-γ and TNF-α) are crucial for innate host defense against systemic infection (Elkins et al., 2003; and Leiby et al., 1992). *F. tularensis* strain LVS (type B) is a vaccine strain and *F. tularensis* subsp. *tularensis* (type A) strain SCHU S4 is a prototypic strain of the pathogen that is highly virulent for humans and other mammals. Its intradermal (i.d.) 50% lethal dose ($LD_{50}$) for mice is <10 CFU.

This suggests that stimulation of an effective immune response by cyclic dinucleotide molecules, such as c-di-GMP, either alone or as part of a vaccine, would have utility in inhibiting infection against this *F. tularensis*.

The following procedure using an animal model of infection may be employed to inhibit infection due to *F. tularensis* in humans and animals:

Mice (e.g., C57BL/6) are administered with a dose of c-di-GMP. Routes of administration include but are not limited to oral, intranasal, intradermal, s.q., i.p. i.v, prior to exposure with *F. tularensis*. Exposure may be either by aerosol or intradermal route of infection. Mice receiving an aerosol challenge with 20 CFU of *F. tularensis* (e.g., *F. tularensis* LVS (ATCC 29684 or Schu S4 strain) and not receiving c-di-GMP pretreatment are expected to develop clinical signs of severe disease, weight loss by day 4 of infection and death the next day. Histopathological findings in the lung will reveal acute inflammation and intense vasculitis and perivasculitis on day 4. Neutrophils, tumor necrosis factor alpha (TNF-α), and interferon gamma (IFN-γ) appear to be absolutely essential for effective control of primary murine tularemia in that the $LD_{50}$ of LVS plunges dramatically in their absence.

Mice are intradermally or aerosol inoculated to get bacteria into lower airways of mice inoculated with varying low doses (20 cfu) or moderate sublethal dose ($3 \times 10^5$ cfu) of *F. tularensis* LVS (ATCC 29684) and their survival monitored. In addition, blood of mice sacrificed at various times post-inoculation is collected for the determination of serum cytokine levels. The inguinal lymph nodes (LN), lungs, spleens and livers are removed, homogenized and used for quantitative bacteriology or fixed immediately by immersion in 10% neutral buffered formalin for histopathology. Serum cytokine levels (e.g. IFN-γ, TNF-α, IL-12p40 and IL-6) are measured by sandwich enzyme-linked immunosorbent assays (ELISA).

A comprehensive examination of the course of a sublethal LVS infection in mice shows that the course of infection proceeds by outgrowth of the pathogen in both inguinal LN (the regional draining LNs for the inoculation site) and systemic organs (spleens and lungs).

Mice are susceptible to a moderate sublethal intradermal challenge with LVS ($10^5$ cfu) as seen by mortality, median time to irreversible moribundity, bacterial burdens in the regional draining lymph nodes, spleens, livers and lungs, tissue damage, and the circulating levels of proinflammatory cytokines (TNF-α, IL-12p40 and IFN-γ). Intradermal inoculation of mice with a moderate sublethal dose of LVS induces a substantial increase of serum IFN-γ levels and a moderate increase of serum IL-12p40 levels over the course of the infection.

Mice that recover from sublethal infection with the c-di-GMP vaccine are expected to survive when challenged 2 months later with *F. tularensis*. In both human and animal studies, systemic vaccination with LVS provided only suboptimal protection against aerosol challenge with type A *F. tularensis* (Eigelsbach et al., 1961; and Hornick et al., 1966). For these reasons, LVS has never been fully licensed as a vaccine and, in turn, this has motivated a search for better-defined vaccines of equal or greater efficacy (Conlan et al., 2004; and Sojöstedt, 2003). c-di-GMP given alone (orally, intranasally, intradermally, s.q., i.p. or i.m.) or as part of a vaccination approach (intranassaly, intradermally, s.q., i.p. or i.m.) with a suitable *F. tularensis* antigen(s) or as adjuvant and part of a live attenuated or whole cell (live or dead) vaccine approach can be used to effectively protect mice against challenge with a highly virulent type A strain, and the protective efficacy is expected to be at least as good as that of *F. tularensis* LVS, an empirically attenuated strain which has been used as an efficacious human vaccine.

BALB/c mice challenged intradermally with $10^2$ to $10^8$ CFU of LVS display overt signs of illness between days 4 and 11 (hunched gait, pilo-erection, lethargy), and some mice inoculated with $10^7$ or $10^8$ CFU died by day 8 of infection. C-di-GMP treated mice would exhibit increased survival.

BALB/c mice intradermally challenged with $10^6$ CFU strain LVS and then killed on day 4 of infection show LVS present at a greater level in the skin and liver and 20-fold-higher levels in the spleen than c-di-GMP treated mice. Moreover, large macroscopic skin lesions were visible at the site of inoculation of LVS but not in c-di-GMP treated mice. Histologically, these LVS-induced lesions consist of large areas of degenerative and necrotic dermatitis containing degenerating and necrotic epidermal cells with detachment of the epidermis from the subdermal layer and, in places, the complete disappearance of the epidermal layer. Large numbers of mixed inflammatory cells, predominantly polymorphonuclear leukocytes, infiltrate the adjacent subdermal region which also contain large numbers of necrotic inflammatory cells and debris. The epidermis adjacent to these severely affected areas is thickened with increased amounts of keratin. Less extensive destruction of skin and inflammation is expected at the site of inoculation of c-di-GMP treated mice.

In humans, intradermal or inhaled inocula of 10 cfu or less of the most virulent strains of the pathogen are sufficient to cause severe infection and possible death; in mice similar inocula are routinely lethal. Intranasal or intradermal c-di-GMP treated or c-di-GMP vaccinated (immunized) mice are expected to show increased survival, less bacterial organ dissemination and excellent protection following aerosol or intradermal challenge with *F. tularensis* several weeks to months later. Similar protective findings as well as an increased immune response and increased antigen-specific antibodies against *F. tularensis* are expected not only in animals but also in humans treated with c-di-GMP alone or as part of a vaccine.

EXAMPLE 4

Use of Cyclic Dinucleotides (e.g. c-di-GMP) to Inhibit *Cryptococcus neoformans* Infection Respiratory infections are the third leading cause of death worldwide. Complications arise directly as a consequence of pathogen replication or indirectly due to aberrant or excessive immune responses. *C. neoformans* is a fungus and is a serious human respiratory pathogen that replicates in the lung causing pulmonary eosinophilia in immunocompromised hosts but may disseminate systemically leading to meningitis, particularly in immunocompromised individuals. Recent interest in this organism results from an increasing incidence of human cryptococcal infections, mostly associated with the worldwide AIDS epidemic. In immune deficient patients, dissemination of the pathogen occurs due to the inability of the host to limit the infection (Levitz, 1991; and Currie et al., 1994). Protection from *C. neoformans* infection depends on both $CD4^+$ and $CD8^+$ T cells (Hill et al., 1991; Huffngle et al., 1991a and 1991b; and Mody et al., 1993). Although both lymphocyte subsets may affect the pathogen directly, indirect immune activation of NK cells (Horn et al., 1995), neutrophils, and macrophages (Collins et al., 1992) may also confer host resistance.

The following procedures using an animal model of infection may be employed to demonstrate inhibition of inhibit infection due to *C. neoformans*:

In mice, protection from *C. neoformans* infection depends on the genetic background of the inbred strain used. Resistant mice (CBA, C.B-17, BALB/c) generally produce higher concentrations of type 1 cytokines in response to *C. neoformans* infection (Yuan et al., 1997; Decken et al., 1998; and Kawakami et al., 2000). In contrast, susceptible strains (C57BL/6, C3H, and B10.D2) develop a Th2-driven pulmonary eosinophilia, produce low IFN-γ and IL-12 and at the peak of pathogen burden up to 40% of airway cells are eosinophils. This response is nonprotective and results in tissue damage resulting from degranulation and crystal deposition by eosinophilia (Huffnagle et al., 1998).

Using a murine model of *C. neoformans* infection, c-di-GMP alone or as part of a vaccine can be administered either nasally, i.p., s.q., i.m. or intradermally to stimulate a Th1 immune response, inhibit infection, increase survival, and suppress the pathology associated with *C. neoformans* infection. C-di-GMP can be used to inhibit Th2 responses and pulmonary eosinophilic responses. It is proposed that c-di-GMP pretreatment or post-infection, can be used to prevent pulmonary and pathogen-driven eosinophilic disease, and increase survival of the host.

Eight- to 12-wk-old female C57BL/6 mice can be used as a model for *C. neoformans* infection. *C. neoformans* strain 52 can be used for infection and diluted in sterile nonpyrogenic saline to the required infective dose.

c-di-GMP pretreatment (e.g. 48- and 24 h) can be given prior to infection. On day 0, mice are anesthetized with halothane and intranasally infected with $2\times10^4$ CFU *C. neoformans* in 50 µl sterile PBS. Mice are then sacrificed at various time points after *C. neoformans* infection by injection of 3 mg pentobarbitone and exsanguinated via the femoral vessels. Bronchoalveolar lavage (BAL) fluid, lung tissue, and sera are to be recovered using methods described previously (Hussell et al., 1996).

Briefly, the lungs of each mouse are inflated six times with 1 ml 1 mM EDTA in DMEM and placed in sterile tubes on ice. A total of 100 µl BAL fluid from each mouse was cytocentrifuged onto glass slides. The remainder is centrifuged, and the supernatant removed and stored at −70° C. in 200-µl aliquots for analysis of cytokines by ELISA. Cell viability is assessed using trypan blue exclusion, and the pellet was resuspended in RPMI containing 10% FCS, 2 mM/ml L-glutamine, 50 U/ml penicillin, and 50 µg/ml streptomycin (R10F) at a final concentration of $10^6$ cells/ml. Eosinophils are enumerated as granulocytes by flow cytometry, using forward and side scatter. Identification is confirmed by counting eosinophils in H&E-stained cytocentrifuge preparations.

Lungs are homogenized by passage through 100-µm cell strainers (BD Labware, Bedford, Mass.). A total of 100 µl of cell suspension is diluted in PBS and incubated at room temperature for 48 h on Sabouraud dextrose agar plates (Sigma-Aldrich). The total CFU per lung is determined (number of colonies×dilution factor×original cell suspension volume).

A total of $2\times10^5$ CFU/ml heat-killed *C. neoformans* in PBS is used to coat 96-well microtiter plates overnight at room temperature on a shaker. After blocking with 3% BSA/PBS for 2 h at 37° C., dilutions of sample sera is added for a further hour at room temperature. Bound Ab is detected using peroxidase-conjugated rabbit anti-mouse Ig and O-phenylenediamine as a substrate. The reaction was stopped with 50 µl 2.5 M sulfuric acid. ODs is read at 490 nm, and mean blank values (ODs from normal mouse serum) subtracted from the OD values of test samples.

A significantly reduced pathogen burden is expected in c-di-GMP-treated mice compared with controls. Based on its immunostimulatory ability, c-di-GMP treatment can be used to reduce the percentage of eosinophilia in the lung.

Because eosinophilia in this model requires CD4[+] T cells secreting type 2 cytokines, only a few lung CD4[+] T cells express intracellular IFN-γ in control-treated mice, however, c-di-GMP treated mice are expected to show increased IFN-δ production and increased total numbers of CD4[+]/IFN-γ[+] cells. c-di-GMP treatment shifts the cytokines to a Th1 phenotype.

The potential reduction of *C. neoformans* burden by c-di-GMP treatment is also likely to be dependent on enhanced IFN-δ, which activates macrophages and increases their fungicidal activity (Flesch et al., 1989; Mody et al., 1991; and Kawakami et al., 2000). CD4[+] T cells play an important role in recruiting macrophages during virulent cryptococcal infection (Huffnagle et al., 1994). In previous studies, increased IFN-γ and an increase in the number of recruited macrophages were observed. This therefore provides an environment more equipped to manage fungal clearance. Previous studies have detailed the importance of IL-12 in protection from *C. neoformans* (Yuan et al., 1997; Decken et al., 1998; and Kawakami et al., 2000). Consistent with the ability of c-di-GMP to induce a Th1 immmune response and to inhibit *C. neoformans* infection, studies in the Examples above showed that c-di-GMP increases IL-12 production in human DCs.

Immunization of susceptible C57BL/6 mice with c-di-GMP would deviate the immune response from a Th2- toward a Th1-type response following infection with *C. neoformans*. C-di-GMP also induces IL-12, TNF, MCP-1. More importantly, pulmonary eosinophilia is expected to be significantly reduced, an effect that depends on IL-12 and CD8(+) T cells but not NK cells. An equivalent beneficial effect is expected when c-di-GMP treatment is delivered during established cryptococcal disease. Activation of innate immunity has clear therapeutic potential and may even be beneficial in patients with acquired immune deficiency. Oral, intranasal, i.p., i.v., s.q., or i.m. c-di-GMP administration is expected to increase survival and to reduce infection-induced lung eosinophilia for prolonged periods. This effect is accompanied by a change in type 1 and type 2 cytokines.

Eight- to twelve-week-old female C57BL/6 mice can be treated with c-di-GMP prior to infection. For infections, mice can be infected intranasally with $2\times10^4$ CFU of *Cryptococcus* per mouse. Animals are sacrificed by intraperitoneal injection of a lethal dose of pentobarbital 13 days later, followed by exsanguination via the femoral arteries.

Bronchoalveolar lavage (BAL) fluids, lung tissues, and serum samples are harvested. Briefly, the lungs of each mouse are inflated six times with 1 ml of 12 mM lidocaine in Eagle's minimal essential medium and BAL fluid kept on ice. BAL fluid (100 µl) is cytocentrifuged onto glass slides and stained with hematoxylin and eosin (H&E). The remainder of the BAL fluid is centrifuged, the supernatant is retained at −80° C., and the pellet is resuspended at a concentration of $10^6$ cells/ml. Lungs and spleens are homogenized by passage through 100-µm-pore-size cell strainers, red blood cells are lysed in ammonium chloride buffer, and the remaining cells washed and resuspended in RPMI medium with 10% fetal calf serum. Cell numbers are determined by counting cells on hemocytometer slides by using a microscope and trypan blue exclusion to identify viable cells.

IL-4, IL-5, IFN-γ, transforming growth factor β (TGF-β), and TNF can be assessed in lung lavage supernatants and serum samples by using enzyme-linked immunosorbent assay (ELISA) according to the manufacturer's instructions (Becton Dickinson-Pharmingen). Total (acid-activated) and bioactive (not acid-activated) TGF-β levels can be determined. Briefly, Immunosorb ELISA plates (Nunc) are coated with capture antibody and left overnight at 4° C. Wells are then washed five times with PBS-0.05% Tween 20 and blocked with PBS-10% fetal bovine serum for 1 h at room temperature. One hundred microliters of sample (undiluted) or standard is added to blocked wells for 2 h at room temperature. Bound cytokine is detected by using biotinylated anti-cytokine antibody, Avidin horseradish peroxidase, and tetramethylbenzidine. Color development is blocked with 2 N H$_2$SO$_4$, and optical densities read at 450 nm. The concentration of cytokine in each sample is determined from the standard curve.

*Cryptococcus* infection alone results in extensive eosinophilia, and can be dramatically reduced by prior c-di-GMP. Prominent neutrophil recruitment into the BAL fluid is expected in the *C. neoformans* (alone) infected group but not in those treated with c-di-GMP. c-di-GMP treatment is expected to decrease total cell recruitment and BAL fluid eosinophilia after fungal infection. The effect of prior c-di-GMP treatment on *Cryptococcus*-induced BAL fluid eosinophilia is expected to be still apparent when *C. neoformans* is introduced several months after c-di-GMP inoculation.

Since *Cryptococcus*-induced eosinophilia relies on IL-5, and c-di-GMP treatment does not induce IL-5 production, eosinophilia is expected to be low in c-di-GMP treated mice. IFN-γ plays a central role in alteration of the Th2 immune response and *C. neoformans* infection. C-di-GMP treated mice are expected to have elevated serum IFN-γ levels leading prolonged elevation of type 1 cytokines and successfully controlled *C. neoformans* infection.

c-di-GMP treatment can be used to suppress *Cryptococcus*-induced airway eosinophilia, an effect that is long lasting. Early cytokine production during pulmonary *Cryptococcus* infection determines susceptibility (Hoag et al., 1997). Th1-type cell-mediated immunity with IL-12, IFN-γ, (Hoag et al., 1997) and TNF production (Huffnagle et al., 1996) is critical for clearance of the organism. IL-5, on the other hand, is required for eosinophil and mononuclear cell recruitment during infection in susceptible C57BL/6 mice (Huffnagle et al., 1998) that produce less of the type 1 cytokines. The increase in intracellular IFN-γ production by lung cells and in IFN-γ secretion in serum and BAL fluid seen in c-di-GMP treated immune animals presumably reciprocally inhibits *C. neoformans*-induced Th2 cells.

EXAMPLE 5

Use of Cyclic Dinucleotides to Inhibit Viral Pneumoniae (Influenza Virus) and Secondary Pneumonia Vaccination represents the most effective form of protection against influenza infection. It is well appreciated that upper respiratory tract viral infections are often complicated by more serious bacterial diseases. While influenza virus is most commonly thought of in this context, other respiratory viruses, including respiratory syncytial virus, measles virus, parainfluenza viruses, adenovirus, and rhinoviruses may also predispose to secondary infections. Several different bacteria have also been implicated, including *Haemophilus influenzae, Staphylococcus aureus, Streptococcus pyogenes, Mycoplasma pneumoniae*, and the pneumococcus. A lethal synergism exists between influenza virus and pneumococcus, which likely accounts for excess mortality from secondary bacterial pneumonia during influenza epidemics. While neutralizing antibodies are typically measured as a correlate of vaccine-induced protective immunity against influenza, non-neutralizing antibodies may contribute to protection or amelioration of disease. Expression of IgG2a antibodies would correlate with clearance of virus and increased protection against lethal influenza challenge.

c-di-GMP can be used either alone or as part of an influenza vaccine regimen that selectively enhances IgG1 or IgG2a antibodies. After c-di-GMP vaccination, neutralizing antibodies can be detected by both in vitro (microneutralization) and in vivo (lung viral titer) methods and are associated with increased IgG1 expression by enzyme-linked immunosorbent assay (ELISA).

A mouse model of synergy reveals that influenza infection preceding pneumococcal challenge primes for pneumonia and leads to 100% mortality. This effect is specific for viral infection preceding bacterial infection, because reversal of the order of administration leads to protection from influenza and improved survival. Using a mouse model of secondary pneumococcal pneumonia after influenza, c-di-GMP can be used to increase survival and inhibit secondary pneumonia, even when therapy is delayed for several days after infection with influenza virus. Pre-treatment or post-treatment of the predisposing influenza-virus infection with c-di-GMP may also improve the efficacy of antibiotics and increase survival in persons who are at high risk for complications and mortality during influenza.

Mice (e.g., female balb/c mice, 8-10 weeks of age, average weight around 18-20 g) pretreated (e.g., orally, intranasally, i.p., i.m., i.v., s.q.) with c-di-GMP at 48- and 24 h prior to infection with either 100, 3000 TCID$_{50}$ of the mouse-adapted Mount Sinai strain of influenza virus A/Puerto Rico/8/34 (H1N1, PR8 are expected to show increased survival, less weight loss, less viral and increased viral clearance (lung viral titers) compared to control mice not treated with c-di-GMP.

To study the effects of c-di-GMP on inhibiting pneumonia, two strains of bacteria will be utilized: *S. pneumoniae* strain D39 (type 2), and *S. aureus* strain NCH57 (a PVL+ clinical isolated from a patient with necrotizing pneumonia). D39 causes pneumonia and bacteremia in mice and is lethal with an MLD$_{50}$ of 5×10$^5$ CFU/mouse when administered alone, and 500 CFU/mouse when administered following influenza. D39 has been engineered to express luciferase so infections can be followed using bioluminescent imaging with the Xenogen system. NCH57 causes a lethal, toxin/inflammatory response lung infection in mice with an MLD$_{50}$ of 1×10$^9$ CFU/mouse. Influenza lowers this MLD$_{50}$ by 2-3 logs.

Groups of 6 mice can be infected with 1×10$^5$ CFU of D39 following c-di-GMP pretreatment 24- and 48 hours (e.g., orally, intransal, i.p, s.q. i.m.) prior to infection with 200 nmol of either c-di-GMP or c-GMP as a control and euthanized 24 hours later for enumeration of bacterial counts in the lungs. C-di-GMP treated mice are expected to show decreased bacterial counts, an increased immune response and inhibition of pneumonia.

Groups of 6 mice will be infected with 1×10$^9$ CFU of NCH57 following c-di-GMP pretreatment (e.g., orally, intransal, i.p, s.q. i.m.) 24- and 48 hours prior to infection with 200 nmol of either c-di-GMP or c-GMP (control) and followed for weight loss and mortality. C-di-GMP treated mice are expected to show greater survival, an increased immune response and inhibition of pneumonia.

To show the effect of c-di-GMP secondary bacterial pneumonia following influenza infection, groups of 6 mice are infected with 100 TCID$_{50}$ of PR8 and challenged 7 days later with either 1000 CFU of D39, or 1×10$^7$ CFU of NCH57 and followed twice daily for weight loss, development of secondary bacterial infections by bioluminescent imaging, and mortality. One group of mice is treated with c-di-GMP 24- and 48 hours (e.g., orally, intransal, i.p, s.q. i.m.) prior to bacterial challenge with 200 nmol/animal. C-di-GMP treated mice are expected to less weight loss, show greater survival and less mortality, an increased immune response and inhibition of secondary pneumonia.

To show the effect of c-di-GMP in an influenza vaccination model, groups of 10 mice are vaccinated by one of 4 vaccines twice 3 weeks apart. Vaccines include standard inactivated whole influenza virus, live attenuated influenza vaccine, DNA vaccine delivered i.m., and DNA vaccine delivered via gene gun. Influenza virus B/Yamanashi/166/98 is used as the vaccine virus and challenge virus. The study design involves 3 groups for each vaccine type: no adjuvant, alum as an adjuvant, and c-diGMP as an adjuvant. Blood is drawn 2-3 weeks after the primary and secondary vaccinations for assessment of the antibody response by hemagglutination-inhibition, micro-neutralization, and ELISA including IgG1 and IgG2a subclasses. 3 weeks after secondary vaccination mice are challenged with $1\times10^6$ $TCID_{50}$ of mouse-adapted BYamanashi (~3 $MLD_{50}$) and followed for weight loss and survival. C-di-GMP treated mice are expected to less weight loss, show greater survival and less mortality, an increased immune response, increased strain and antigen-specific antodies and heterologous immunity, and inhibition of influenza virus infection including viral lung titer. c-di-GMP can be used alone or as part of a vaccine to inhibit influenza virus infection as well as secondary pneumonia after influenza.

EXAMPLE 6

Use of Cyclic Dinucleotides to Inhibit *Candida albicans* Infection

Systemic infection with *Candida albicans* is a significant cause of morbidity in immunocompromised hosts, including transplant recipients and AIDS patients. The organs affected and the major sites of fungal replication during disseminated candidiasis are the kidney, heart, and brain, and death follows multiple-organ failure (Kullber et al., 2002; and Parker et al., 1976). The mouse model of acute infection with *C. albicans* is a valuable experimental model for studying microbial pathogenesis, as it includes many of the clinical features of the human condition (Ashman, 1998; and Tuite et al., 2004). The treatment of patients with high-dose immunosuppressive regimens, broad-spectrum antibacterial antibiotics, or cancer chemotherapy contributes to the prevalence of candidiasis (Anaissie et al., 1993 and 1990; cole et al., 1996; Mahfouz et al., 2003; O'Brien et al., 2003; Pappas et al., 2004; Rex et al., 1998; and Samonis et al., 1992). Treatments to clear colonized oral mucosa or the gastrointestinal tract can be difficult, and these patients may progress to develop disseminated disease, likely of gastrointestinal origin. Thus, the availability of a model that mimics these manifestations becomes invaluable in for the study of therapeutics as well as pathogenesis.

Systemic candidiasis is a significant cause of nosocomial infections and the mechanisms of defense against *Candida albicans* in humans remain poorly understood. Studies in animal models have demonstrated the importance of innate immunity in controlling the response to infection. Although Th1 cytokines have been shown to direct the overall outcome of infection, the precise role of the Th1/Th2 response and, more generally, the adaptive immune response as a whole, in systemic candidiasis, appears to apply mainly to the development of resistance to reinfection.

An early immune response to infection is a crucial component of a host's ability to control the growth of the invading microorganisms and eradicate them. In particular, proinflammatory cytokines, such as TNF-α, form part of an early detection system, and they provide immediate signals that allow the host to discriminate between self and nonself. The recognition of invading pathogens triggers a series of signal transduction cascades and associated inflammatory and early immune responses. Under normal conditions, these responses are strictly regulated to produce optimal antimicrobial effects while minimizing collateral damage to the host. However, under certain conditions, either due to the strength of the danger signal or due to failure of negative regulatory mechanisms, the inflammatory response overwhelms the host and causes significant damage, including morbidity. These and other studies have shown that both a functional complement pathway and robust inflammatory response are critical for resistance to *C. albicans*.

Inbred strains A/J and C57BL/6J (B6) have been used to study the susceptibility to acute infection with *C. albicans* (Mullick et al., 2004). The A/J mouse strain is exquisitely sensitive to candidiasis with high fungal loads in target tissues, and rapid death occurs within 24 h following intravenous injection of $3\times10^5$ *C. albicans* blastospores.

To show the efficacy of c-di-GMP in inhibiting *C. albicans* infection, 8- to 12-week-old A/J and C57BL/6J mice are infected with *C. albicans* strain SC5314. The blastospores are washed twice in phosphate-buffered saline (PBS) and resuspended in PBS at the required density. For experimental infections, A/J and C57BL/6J mice are inoculated via the tail vein with 200 μl of a suspension containing $3\times10^5$ *C. albicans* blastospores in PBS. One group of mice will be pretreated with c-di-GMP (intranasally, i.p., i.m., s.q.). Mice are to be closely monitored for clinical signs of disease, such as lethargy, loss of appetite, hunched back, and ruffled fur. Mice treated with c-di-GMP (either orally, intranasally, i.p, i.m., i.v, or s.q) are expected to show an increased immune response, less lethargy, less mortality, less systemic spread, and overall less clinical signs of disease.

The levels of TNF-α and IL-6 in tissue extracts are determined using "two-site sandwich" assays with commercially available enzyme-linked immunosorbent assay (ELISA) kits (BD Biosciences). Tissue extracts are prepared by homogenization in lysis buffer (20 mM Tris [pH 7.5], 0.3 M NaCl, 2% sodium deoxycholate, 2% Triton X-100, protease inhibitor cocktail [Roche Diagnostics]). Additional determinations of the levels of 32 cytokines and chemokines are carried out by using cardiac tissue extracts and RayBio mouse cytokine array II membranes (RayBiotech Inc., Norcross, Ga.). Incubation, washing, and detection are performed according to the instructions of the manufacturer. All values are normalized to the protein content and determined using the Bradford reagent. C-di-GMP treated mice would exhibit an increased immunological response toward a Th1 immune response, consistent with a protective effect and ability to inhibit *C. albicans* infection.

Candidiasis of the oral mucosal surfaces and the intestinal tract is problematic for a variety of patient populations. Those at the highest risk include those with AIDS and those on immunosuppressive therapy (e.g., cancer chemotherapy or high-dose steroids). Disseminated candidiasis in cancer chemotherapy patients is thought to arise from the translocation of *C. albicans* across gut mucosa damaged from chemotherapy treatment. A murine model of gastrointestinal candidiasis mimicking this situation and resulting in systemic dissemination and death has been previously reported (Sandovsky-Losica et al., 1992). However, attempts to replicate this model resulted in minimal or inconsistent dissemination and little to no lethality due to *Candida albicans* (Bendel et al., 2002; DeMaria et al., 1976; Ekenna et al., 1987; Samonis et al., 1996; Wingard et al., 1982; and Wingard et al., 1980). A modified mouse model has been further developed and standardized as a model of disseminated disease arising from translocation from gut colonization, to induce oral mucosal disease, and to determine the utility of this model for the study of therapeutic intervention.

To test the efficacy of c-di-GMP to inhibit Candidaiasis of the oral mucosal surfaces and the intestinal tract, *C. albicans* given to mice in the drinking water results in oral infection by day 3 that significantly increased from days 10 to 15 and mucosal infection with 4 to 7 $\log_{10}$ *Candida* CFU in the esophagus, stomach, small intestine, and cecum. Dissemination to livers occurs and is 100% on days 5 to 15. The median kidney or liver CFU were 2 or 3 $\log_{10}$ CFU, respectively, on day 15; despite this, mortality was low through 21 days of infection. Based on its ability to stimulate an immune response, c-di-GMP treatment can be used to reduce mucosal infection and infection in the stomach, small intestine and cecum as well as dissemination to the liver and kidneys and reduced tongue CFU compared to untreated controls.

EXAMPLE 7

Use of Cyclic Dinucleotides to Inhibit *Pneumocystic carinii* Infection

*Pneumocystis carinii* produces a life-threatening pneumonia in immunocompromised patients, especially those with AIDS. The clinical syndrome of *P. carinii* pneumonia (PCP) has been well described in terms of presentation, diagnostic and therapeutic interventions, as well as morbidity and mortality. The clinical severity of *Pneumocystis carinii* pneumonia (PCP) correlates closely with the appearance of pulmonary markers of inflammation.

A model system has been developed whereby physiological studies can be performed on live mice to determine the extent to which pulmonary inflammation contributes to respiratory impairment during PCP. *P. carinii*-infected severe combined immunodeficient mice display little evidence of pulmonary inflammation and exhibited normal oxygenation and dynamic lung compliance. When comparably infected littermates are immunologically reconstituted, however, an intense immune-mediated inflammatory response was observed that resulted in significant decreases in both lung compliance and oxygenation. As the pneumonia resolves, pulmonary function returns toward normal. The host's response to *P. carinii* directly impairs pulmonary function and contributes to the pathogenesis of PCP. Furthermore, CD8+ T cells likely contribute to the respiratory compromise observed during PCP.

To demonstrate the ability of c-di-GMP to inhibit *P. carinii* infection, female C57BL/6 mice, 4 weeks of age, are either infected with *P. carinii* or pretreated with c-di-GMP (orally, intransally, i.p, i.m., i.v., s.q.) 48- and 24 h prior to infection. Lungs from CB.17 SCID mice maintained in a *P. carinii*-infected colony were used as a source of *P. carinii*. Recipient mice were anesthetized with halothane gas and given intratracheal inoculations of 100 μL of lung homogenates containing 108 *P. carinii* nuclei/mL with a blunted 20-gauge needle inserted into the trachea through the oral pharynx. C-di-GMP treated mice are expected to show increased survival, an increased immunological response and overall less clinical disease.

Immunoprophylaxis is one method used to protect patients against infection if they are unable to mount an adequate active immune response. C-di-GMP treatment prior to infection may be effective against infections at mucosal sites. Using a SCID mouse model of *Pneumocystis carinii* pneumonia, c-di-GMP treatment (orally, intransaaly, i.p, i.m., i.v., s.q.,) can be used to provide protection against an airborne challenge with *P. carinii*. C-di-GMP treatment has utility in protecting at-risk patients from infection with *P. carinii*. Because *Pneumocystis carinii* pneumonia (PCP) is an opportunistic infection affecting individuals with significantly compromised immune systems, c-di-GMP treatment is a preventive strategy that would be well suited for at-risk patients. CD4 T-cell-dependent immunity to *P. carinii* is a critical factor in the host's normal resistance to overwhelming infection with this organism (Harmsen et al., 1990; and Shellito et al., 1990), and this immunity can be expressed through antibody-mediated protection (Gigliotti et al., 1988; and Roths et al., 1993). The use of passive antibody immunoprophylaxis together with c-di-GMP in humans with compromised immunity would also be effective in protecting against clinical disease. MAbs specific for gpA have been shown to decrease the severity of infection when administered systemically (Gigliotti et al., 1996 and 1988).

*P. carinii*-free SCID mice are challenged with *P. carinii* by cohousing them with *P. carinii*-infected "seed" mice. For these experiments, *P. carinii*-free SCID mice are lightly anesthetized with halothane and c-di-GMP alone or c-di-GMP with antibody is instilled by touching a 50-μl drop to their noses and allowing the drop to be inhaled by each mouse's respiratory effort. Beginning with day 1 of treatment, the mice are housed four to five per microisolator cage with two *P. carinii*-infected seed mice added to each cage. C-di-GMP alone or with antibody is administered once daily during 14 days of cohousing. After 14 days, the mice are separated from the seed mice, placed in clean microisolator cages, and given three additional once-daily antibody treatments as described above. Six to seven weeks after the commencement of cohousing, the mice were sacrificed and analyzed for the presence of *P. carinii*.

To enumerate *P. carinii* nuclei, mouse lungs are homogenized by mincing and passing them through a fine stainless steel mesh screen in 5 ml of Hanks' balanced salt solution (GIBCO, Grand Island, N.Y.). The homogenate is prepared for staining by cytospinning 0.1 ml of a 1:10-diluted aliquot onto a slide. Organisms were stained with Diff Quik (Baxter, Miami, Fla.), and the numbers of *P. carinii* nuclei in 50 to 100 fields are counted. The lower limits of detection by this method are approximately 3.76 log10 units when 100 fields are counted and 4.3 log10 units if only 50 fields are counted. Based on its immunostimulatory activity, c-di-GMP treatment can be used to provide protection to SCID mice exposed to *P. carinii*. In addition to *P. carinii*, c-di-GMP treatment is expected to be protective for other fungi which enter the respiratory tract via inhalation, such as *Cryptococcus* spp., *Histoplasma* spp., *Blastomyces* spp., and *Coccidioides* spp. The potential value of considering such an approach for humans may be dependent on the ability to identify high-risk groups who will benefit from such therapy and on comparison with other available means of protection against any of these infections. This approach offers an alternative for prophylaxis of patients against PCP by the use of nasal sprays or nebulization devices.

EXAMPLE 8

Use of Cyclic Dinucleotides to Modulate the Allergic Response.

Basophils are a significant source of IL-4 and very likely IL-13, key factors influencing the allergic response. It is known that cells from allergic subjects secrete more in response to IL-3 than do cells from normal subjects. Also, cells from allergic subjects spontaneously produce IL-13 following repeated allergen challenge, so there are systemic effects (that is referred to as "priming"). It may be that basophil priming (partly determined by IL-13 secretion) correlates with low IFN-a production by pDC.

Figure 18A:
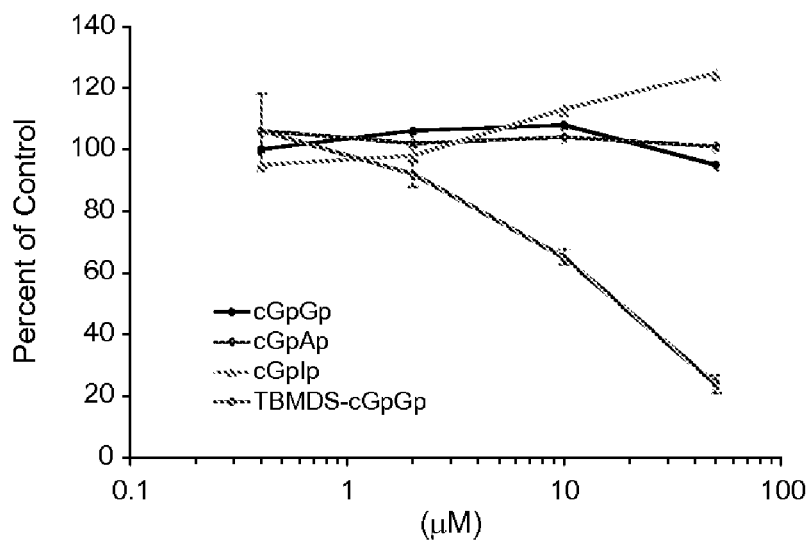
FIGS. 18A and 18B are graphs showing the effect of cyclic dinucleotides on IL-3 dependent IL-13 secretion (FIG. 18A) and on IgE-dependent IL-4 secretion (FIG. 18B) by human basophils.

The ability of cyclic dinucleotide analogs to inhibit the allergic response was tested. At least 5 independent basophil IL-13 experiments using the TBDMS-cGpGp analog (IL-13 induced by IL-3 during an 18-20 h culture) was conducted and all have shown 70-80% inhibition of IL-13 induced by IL-3 at 50 micromolar and 30-40% inhibition at 10 micromolar (FIG. 18A). IL-3 not only induces IL-13 from basophils but also maintains their survival in culture. Note that this survival is not due to proliferation-mature basophils are an end-stage cell with essentially no capacity to proliferate. Checking basophil viability using Trypan blue exclusion might show the TBDMS-GpGp analog does not kill basophils, and therefore must be counter-regulating the effect IL-3 has on basophil cytokine secretion through some other unknown mechanism(s).

At least 4 independent basophil IL-13 experiments have been completed using cGpGp (c-di-GMP), with essentially no inhibition seen under the conditions tested. It may be expected that cGpGp would likely work better to inhibit IL-13 if a pre-incubation period is performed before activating the cells for IL-13 secretion using IL-3. So, if cells are first incubated with cGpGp for 1 or 18 hours and then IL-3 added for an additional 18 h, even more inhibition would likely be observed. Interestingly, a consistent 25% enhancement has been seen with the cGpIp analog in two experiments. Another analog, cGpAp, has little effect. Further tests are needed to determine whether the TBDMS analog affects IgE-mediated release of histamine and IL-4.

The cytokine IL-13 values are the average of duplicate cultures, which are usually within 5-10% of one another. Overall levels vary depending on the donor. In these, the basophils used were from leukopheresis packs, so the allergic status of the donors is unknown (either allergic or non-allergic).

Figure 18B:
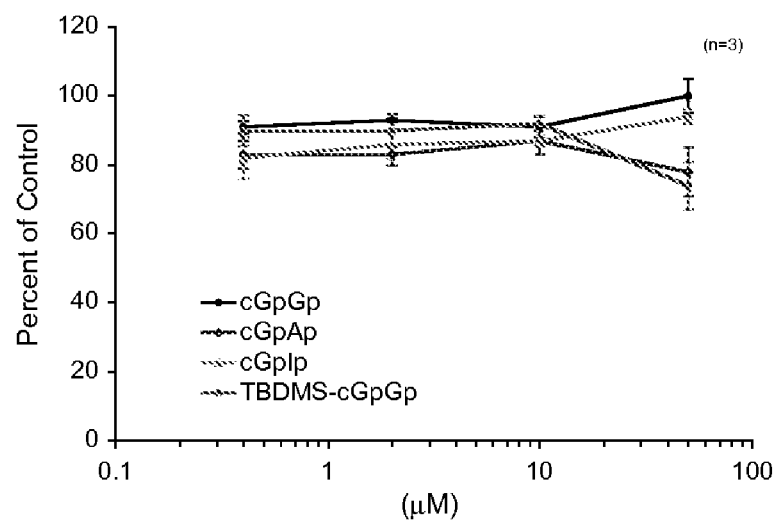

Studies investigating the effect of the TBDMS-cGpGp analog on IgE-dependent IL-4 and histamine secretion induced by cross-linking were then performed. There was essentially no effect on histamine release and IL-4 was inhibited (30%) at the 50 uM concentration (FIG. 18B). The inhibition of IL-4 was evident using the TBDMS-cGpGp analog as well as the cGpAp analog. Note that IgE-mediated histamine release is 90% complete within 20 minutes after stimulation- histamine is preformed and store in cytoplasmic granules. Although IL-4 is not preformed, it is rapidly generated denovo and secreted within 3-6 hours. In performing these experiments, a standard protocol for testing various anti-allergic drugs was used.

Specifically, the basophils were pretreated 15 minutes with the analogs before adding anti-IgE antibody for activation. Culture supernatants were analyzed for histamine and IL-4 three hours later. Thus, unlike the IL-13 induced by IL-3 during an 18-20 h culture, the release of histamine and IL-4 are far more rapid under IgE crosslinking conditions. It may be that inhibition would be greater if a greater pre-incubation time was performed with the analogs. Additional experiments will test different pre-incubation times to determine whether greater inhibition is observed. It is important to note that neither analog induced histamine release or IL-4 when used alone at the 50 uM concentration. T this is additional evidence that the inhibitory effect in not due to toxicity- histamine would most likely be released if the analogs were causing cell lysis.

IL-4 measurements were made in an experiment where the cyclic dinucleotide analogs were tested in a 1 hour pretreatment of basophils before activating with anti-IgE antibody. The control release to anti-IgE antibody was 262 pg/106 basophils (a relatively robust response being that cell responsiveness decreases the longer the wait before activating). Both the TBMDS-cGpGp and cGpAp analogs produced ~30% inhibition at the 50μM concentration. These data are consistent with the previous IL-4 experiment where cGpAp and TBMDS-cGpGp also produced inhibition after 15 minutes pretreatment. It may be that overnight incubation with cyclic dinucleotide (similar to the IL-13 inhibition studies) would show even greater inhibition.

With regard to other drugs and their effects on basophil responses: IgE-mediated release of histamine, IL-4 and IL-13 are potently inhibited by FK506 and CsA. This is particularly true for IL-4 (and IL-13) which are inhibited by FK506 in the picomolar range. A 100-fold greater concentrations of these drugs will inhibit histamine release. Interestingly, neither of these drugs inhibit IL-13 induced by IL-3, or the response that is inhibited by the TBDMS-cGpGp analog. As a result, the IgE-dependent pathway for the induction of IL-4 and IL-13 is most likely dependent on NFAT (nuclear factor of activated T cells). Basophils constitutively express NFAT2, but not NFAT1—the latter being found in essentially every other immune cell thus far examined. As noted previously, the IL-13 induced by IL-3 (an IgE-independent pathway) is inhibited by IFN-a (but not by any other cytokines thus far tested) and various anti-allergic drugs (e.g., steroids and antihistamines in the micromolar to sub micromolar range). These drugs also inhibit the IgE-dependent pathways (more so for cytokine than for mediator release).

Whether or not TBDMS would directly induce (or affect CpG-dependent) cytokine (IL-6, TNF-alpha, IL-10) secretion was then tested. Overall, there was little to no effect on TNF-alpha and IL-10. IL-6 was not measured. When used by itself, TBDMS-cGpGp did not cause IL-10 secretion (n=3). Cells from one of the 3 subjects did secrete 100-200 pg/10^6 cells more TNF-alpha than the ~400 secreted in medium alone. The same pattern was seen using these cells when the combination of CpG and TMDMS was used. However, these effects were not evident for the other two pDC preparations. Nonetheless, it does not look as if the pDC are affected by the TBDMS to the extent that basophils are affected.

SOCS-1 (and SOCS-3), when induced, have been shown to bind JAK kinases, preventing the subsequent "docking" of STAT molecules, and thus disrupting signaling pathways. For IL-3-mediated signaling, it is generally well accepted that JAK2/STAT5 pathways are initiated. SOCS activity was originally described with evidence that it blocks JAK2 kinase. An inhibitory effect of cyclic dinucleotides on IL-3-induced IL-13 secretion would found to be similar to that mediated by IFN-a. Since it is well known that SOCS-1 binds and inhibits JAK2 kinase (the first signaling element induced by IL-3), then induction by cyclic dinucleotide may explain the inhibition of IL-13.

Whether or not cyclic dinucleotides affected induction of SOCS (Suppresser Of Cytokine Synthesis) expression in basophils treated with CDN's was then tested. Several of the cyclic dinucleotides were found to induce SOCS genes after a 16-18 h incubation using real-time PCR. The results indicate that SOCS-1 mRNA is induced by TBDMS-cGpGp and by cGpGp. Cells were treated for 18 h, total RNA isolated, and RT-PCR performed for SOCS-1, SOCS-3, and the HPRT housekeeping gene. The fact that cGpGp also induces SOCS-1 may explain why some inhibition of IL-3-induced IL-13 secretion is observed with this cyclic dinucleotide analog. However, it likely has slower kinetics compared to TBDMS-cGpGp in that if one first treats with this CDN for 18 h and then stimulates with IL-3, more inhibition of IL-13 is expected. In the current IL-13 assay, the cyclic dinucleotide is added simultaneously with IL-3. The TBDMS-cGpGp likely induces SOCS-1 expression faster and thus accounts for greater inhibition of IL-13. Therefore, the data suggest that the most active analog with regard to inhibiting IL-13 secretion (TBDMS-cGpGp) may be inducing SOCS more quickly.

While modest inhibitory activity with cGpGp was observed, evidence that cGpGp induces SOCS-1 and sometimes better than TBDMS-cGpGp at this particular time point was observed. These differences might be explained by kinetics and it may be that SOCS gene expression would be higher following TBDMS-cGpGp treatment when examined at an earlier time point.

In this same experiment, TBDMS-cGpGp also induced SOC-3 mRNA—which is often not detected in basophils. Therefore, it appears that the mechanistic explanation for the cyclic dinucleotide-mediated inhibition of IL-3-induced IL-13 secretion might be based on the induction of SOCS.

A current hypothesis is that cyclic dinucleotides inhibit IL-13 by inducing SOCS-1, which is known to interfer with JAK2/STAT5 signaling through the IL-3 receptor (at least in cell lines). This makes sense, because neither IFN-a or CDN inhibit IgE-dependent responses, and these are not regulated through JAK/STAT pathways. Furthermore, no obvious evidence was found that cyclic dinucleotides induce IFN-a from basophil—not surprising since no evidence has been found that basophils have the capacity to secrete this cytokine. Future experiments will look at whether cyclic dinucleotides will induce STAT-1, prevent IL-3 from activating Erk phosphorylation, etc.

With regard to induction of SOCS, the kinetics using the cGpGp CDN is likely slower than using the TBDMS compound. It appears that SOCS mRNA peaks for cGpGp at ~18 h whereas message for SOCS peaks at an earlier time (~12 h) using TBDMS-cGp.

The cyclic dinucleotide analog TBDMS-cGpGp inhibits IL-3—dependent IL-13 secretion better than CpG inhibits IgE-mediated secretion of this cytokine. As such, the use of cyclic dinucleotides as an adjuvant-like substance or to inhibit the allergic response is attractive. The concern regarding the use of CpG centers on their extremely potent Th1-promoting activity, which has caused some to feel that they may actually induce autoimmune disease. Something with less Th1-promoting activity (yet capable of inhibiting Th2-like activity) may be attractive both as an adjuvant (like in cancer vaccines) as well as an anti-allergic immune modifier without the risk of inducing autoimmune disease. Cyclic dinucleotides represent such an anti-allergic immune modifier.

CpG-ODN (oligos of 6-20+ bases) have been of great interest during the past few years. These act like adjuvants and have proven clinical efficacy, inducing pDC and B cell responses through TLR9. Since cyclic dinucleotide analogs promote Th1-promoting responses in DCs, yet also inhibit basophil cytokine responses, their effects are very similar to what has been observed with CpG. However, cyclic dinucleotides do not appear to act through TLRs. Cyclic dinulceotide analogs which have strong Th1-promoting effects can be used to prevent or treat allergic disease to counter-regulate Th2-like responses.

EXAMPLE 9 c-di-GMP has Neuroprotective Properties

To assess the role of cyclic dinucleotides in modulating the neurological response, i.e., prevent cell death induced by staurosporine (STS) in primary hippocampal nerve cells, the effects of c-di-GMP on hippocampal cells was analyzed. Primary hippocampal cells were prepared according to previously described methods (Pereira et al., 1993). Briefly, the hippocampi were dissected from the brain of 18-day-old fetal rats. Following enzymatic and mechanical dissociation, cells were plated at a density of 100,000 cells/well in 96-well plates pre-coated with matrigel. At the $7^{th}$ day after plating, cultures were subjected to one of the following treatments: (i) vehicle (24 h), (ii) STS (100 nM, 22 h), (iii) c-di-GMP (24 h), (iv) c-di-GMP (2 h) followed by c-di-GMP -plus-STS (22 h), (v) c-di-GMP -plus-STS (24 h), or (vi) STS (2 h) followed by c-di-GMP -plus-STS (22 h). At the end of the treatments, cell viability was analyzed using CellTiter 96® $AQ_{ueous}$ Assay (Promega). The assay involves the spectrophotometric measurement (at 490 nm) of the mitochondrial conversion of a tetrazolium dye into a colorful product. The absorbance of the assay correlates with the number of metabolically active cells.

Figure 5:
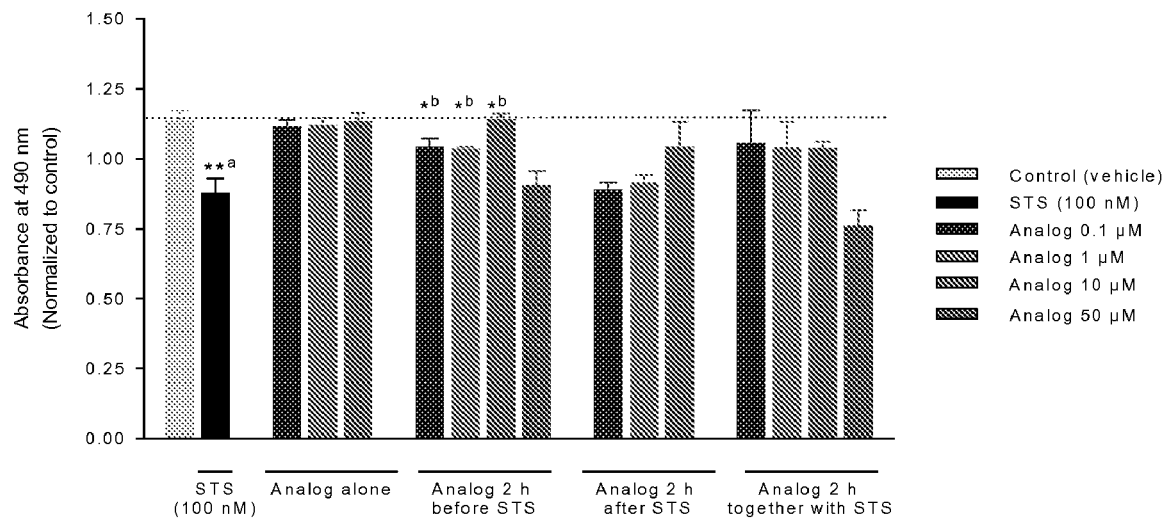
FIG. 5 is a graph showing neuroprotective activity of c-di-GMP on hippocampal cells, protecting cells from both pre-treatment and post-treatment damage by the nerve-damaging agent staurosporine.

The results obtained suggest that hippocampal cells are sensitive to c-di-GMP. Treatment of the primary cultures with STS caused significant cell death as expected. c-di-GMP was not toxic to the primary hippocampal cultures. Pre-treatment of the cultures with c-di-GMP (0.1-10 µM) prevented the STS-induced cell death (FIG. 5, where c-di-GMP is referred to as "Analog" in the figure). When c-di-GMP (0.1-10 µM) was applied to the cultures together with or after STS, the number of metabolic active cells was on average higher than that observed in cultures treated with STS alone.

The results show that the c-di-GMP has neuroprotective properties. A concentration of 0.1-10 µM protects hippocampal neuronal cells from damage by staurosporin, a nerve-damaging agent. More importantly, c-di-GMP shows striking neuroprotective activity post-treatment and appears to restore damaged or dying nerve cells to control levels. Using this molecule alone or in combination with other compounds or as part of a vaccine, it is expected that the protective immune response in acute and chronic insults of mechanical or biochemical origin can be safely boosted. Since this molecule is effective even when given after the insult, and because it protects against the toxicity of staurosporine (a very common mediator of secondary degeneration), it can be used clinically to inhibit or treat diseases such as (but not limited to) neurological, brain, or chronic neurodegenerative disorders such as stroke, glaucoma, Alzheimer's disease, Parkinson's disease, and amyotrophic lateral sclerosis.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Agrawal A, Lingappa J, Leppla S H, Agrawal S, Jabbar A, Quinn C, Pulendran B. 2003. Impairment of dendritic cells and adaptive immunity by anthrax lethal toxin. *Nature*. July 17, 2003; 424(6946):329-34.

Agrawal, A., and B. Pulendran. 2004. Anthrax lethal toxin: a weapon of multisystem destruction. *Cell Mol Life Sci.* 61:2859-2865.

Akagawa, K. S., N. Takasuka, Y. Nozaki, I. Komuro, M. Azuma, M. Ueda, M. Naito, and K. Takahashi. 1996. Generation of CD1+RelB+ dendritic cells and tartrate-resistant acid phosphatase-positive osteoclast-like multinucleated giant cells from human monocytes. *Blood* 88:4029-4039.

Alcon, V. L., M. E. Baca-Estrada, A. Potter, L. A. Babiuk, P. Kumar, and M. Foldvarim. 2006. Biphasic lipid vesicles as a subcutaneous delivery system for protein antigens and CpG oligonucleotides. *Curr. Drug Deliv.* 3:129-35.

Amikam, D., and M. Benziman. 1989. Cyclic diguanylic acid and cellulose synthesis in *Agrobacterium tumefaciens*. *J Bacteriol.* 171:6649-6655.

Anaissie, E. J., and G. P. Bodey. 1990. Fungal infections in patients with cancer. *Pharmacotherapy* 10:164S-169S.

Anaissie, E., and H. Pinczowski. 1993. Invasive candidiasis during granulocytopenia. *Recent Results Cancer Res.* 132:137-145.

Ardeshna, K. M., A. R. Pizzey, S. Devereux, and A. Khwaja. 2000. The PI3 kinase, p38 SAP kinase, and NF-kappaB signal transduction pathways are involved in the survival and maturation of lipopolysaccharide-stimulated human monocyte-derived dendritic cells. *Blood* 96:1039-1046.

Arrighi, J. F., M. Rebsamen, F. Rousset, V. Kindler, and C. Hauser. 2001. A critical role for p38 mitogen-activated protein kinase in the maturation of human blood-derived dendritic cells induced by lipopolysaccharide, TNF-alpha, and contact sensitizers. *J. Immunol.* 166:3837-3845.

Asadullah K, Volk H D, Friedrich M, Sterry W. 2002. Experimental therapies for psoriasis. *Arch Immunol Ther Exp* (Warsz). 50(6):411-20.

Ashman, R. B. 1998. *Candida albicans*: pathogenesis, immunity and host defense. *Res. Immunol.* 149:281-288.

Banchereau, J, and Steinman, R. M. 1998. Dendritic cells and the control of immunity. *Nature* 392:245-252.

Bazan et al, "Mediators of injury in neurotrauma: intracellular signal transduction and gene expression", *J. Neurotrauma* 12(5):791-814 (1995)

Bendel, C. M., S. M. Wiesner, R. M. Garni, E. Cebelinski, and C. L. Wells. 2002. Cecal colonization and systemic spread of *Candida albicans* in mice treated with antibiotics and dexamethasone. *Pediatr. Res.* 51:290-295.

Ben-Nun et al, "The rapid isolation of clonable antigen-specific T lymphocyte lines capable of mediating autoimmune encephalomyelitis", *Eur. J. Immunol.* 11(3):195-199 (1981a)

Bharadwaj, U., R. Zhang, H. Yang, M. Li, L. X. Doan, C. Chen, and Q. Yao. 2005. Effects of cyclophilin A on myeloblastic cell line KG-1 derived dendritic like cells (DLC) through p38 MAP kinase activation. *J Surg Res.* 127:29-38.

Boisleve, F., S. Kerdine-Romer, and M. Pallardy. 2005. Implication of the MAPK pathways in the maturation of human dendritic cells induced by nickel and TNF-alpha. *Toxicology* 206:233-244.

Bomchil, N., P. Watnick, and R. Kolter. 2003. Identification and characterization of a Vibrio cholerae gene, mbaA, involved in maintenance of biofilm architecture. *J Bacteriol.* 185:1384-1390.

Boyaka P N, McGhee J R. 2001. Cytokines as adjuvants for the induction of mucosal immunity. *Adv Drug Deliv Rev.* September 23;51 (1-3):71-9.

Bradney C P, Sempowski G D, Liao H X, Haynes B F, Staats H F. 2002. Cytokines as adjuvants for the induction of anti-human immunodeficiency virus peptide immunoglobulin G (IgG) and IgA antibodies in serum and mucosal secretions after nasal immunization. *J Virol.* January 2002; 76(2):517-24.

Brauner-Osborne et al, "A new structural class of subtype-selective inhibitor of cloned excitatory amino acid transporter, EAAT2" *Eur J Pharmacol*, 406:41-44 (2000)

Brenneman D E, Hauser J, Spong C Y, Phillips T M, Pert C B, Ruff M. 1999. VIP and D-ala-peptide T-amide release chemokines which prevent HIV-1 GP120-induced neuronal death. *Brain Res.* August 14;838(1-2):27-36.

Brieland, J. K., D. G. Remick, M. L. LeGendre, N. C. Engleberg, and J. C. Fantone. 1998. In vivo regulation of replicative *Legionella pneumophila* lung infection by endogenous interleukin-12. *Infect. Immun.* 66:65-69.

Broderson, J. R. 1989. A retrospective review of lesions associated with the use of Freund's adjuvant. *Laboratory Animal Science* 39:400-405.

Broug-Holub, E., G. B. Toews, J. F. van Iwaarden, R. M. Strieter, S. L. Kunkel, R. Paine, and T. J. Standiford. 1997. Alveolar macrophages are required for protective pulmonary defenses in murine *Klebsiella pneumonia*: elimination of alveolar macrophages increases neutrophil recruitment but decreases bacterial clearance and survival. *Infect. Immun.* 65:1139-1146.

Brouillette, E., A. Martinez, B. J. Boyll, N. E. Allen, and F. Malouin. 2004. Persistence of a *Staphylococcus aureus* small-colony variant under antibiotic pressure in vivo. *FEMS Immunol Med Microbiol.* 41:35-341.

Brouillette, E., and F. Malouin. 2005. The pathogenesis and control of *Staphylococcus aureus*-induced mastitis: Study models in the mouse. *Microbial Infection* 7:560-568.

Brouillette, E., M. Hyodo, Y. Hayakawa, D. K. R. Karaolis, and F. Malouin. 2005. 3'-5'-cyclic diguanylic acid reduces the virulence of biofilm-forming *Staphylococcus aureus* strains in a mouse model of mastitis infection. *Antimicrob. Agents Chemother.* 49:3109-3113.

Brouillette, E., P. Lacasse, L. Shkreta, J. Belanger, G. Grondin, M. S. Diarra, S. Fournier, and B. G. Talbot. 2002. DNA immunization against the clumping factor A (ClfA) of *Staphylococcus aureus*. *Vaccine* 20:2348-2357.

Buchanan R M, Arulanandam B P, Metzger D W. 1998. IL-12 enhances antibody responses to T-independent polysaccharide vaccines in the absence of T and NK cells. *J Immunol.* Nov. 15;161(10):5525-33.

Burns et al, "Isolation of myelin basic protein-reactive T-cell lines from normal human blood", *Cell Immunol.* 81(2):435-440 (1983)

Chapel, H. M. and August, P. J. 1976. Report of nine cases of accidental injury to man with Freund's complete adjuvant. *Clinical and Experimental Immunology* 24:538-541.

Cheminay, C., Mohlenbrink, A., Hensel, M. 2005. Intracellular salmonella inhibit antigen presentation by dendritic cells. *J Immunol* 174:2892-9.

Clemons K V, Stevens D A. 2001. Overview of host defense mechanisms in systemic mycoses and the basis for immunotherapy. *Semin Respir Infect.* Mar.;16(1):60-6.

Cole, G. T., A. A. Halawa, and E. J. Anaissie. 1996. The role of the gastrointestinal tract in hematogenous candidiasis: from the laboratory to the bedside. *Clin. Infect. Dis.* 22(Suppl. 2):S73-S88.

Collins, H. L., G. J. Bancroft. 1992. Cytokine enhancement of complement-dependent phagocytosis by macrophages: synergy of tumor necrosis factor-α and granulocyte-macrophage colony-stimulating factor for phagocytosis of *Cryptococcus neoformans. Eur. J. Immunol.* 22:1447.

Conlan, J. W. 2004. Vaccines against *Francisella tularensis*-past, present and future. *Expert Rev. Vaccines* 3:307-314.

Cox, E. F., F. Verdonck, D. Vanrompay, and B. Goddeeris. 2006. Adjuvants modulating mucosal immune responses or directing systemic responses towards the mucosa. *Vet. Res.* 37:511-539.

Currie, B. P., A. Casadevall. 1994. Estimation of the prevalence of cryptococcal infection among patients infected with the human immunodeficiency virus in New York City. *Clin. Infect. Dis.* 19:1029.

D'Argenio, D. A., and S. I. Miller. 2004. Cyclic di-GMP as a bacterial second messenger. *Microbiol.* 150:2497-2502.

D'Argenio, D.A., M. W. Calfee, P. B. Rainey, and E. C. Pesci. 2002. Autolysis and autoaggregation in *Pseudomonas aeruginosa* colony morphology mutants. *J. Bacteriol.* 184:6481-6489.

Dalpke, A., Zimmermann, S. and Heeg, K. 2002. *Biol Chem* 383:1491-500.

Dalpke, A. H., Schafer, M. K., Frey, M., Zimmermann, S., Tebbe, J. Weihe, E. and Heeg, K. 2002. *J Immunol* 168:4854-63.

D'Argenio, D. A., and S. I. Miller. 2004. Cyclic di-GMP as a bacterial second messenger. *Microbiology* 150:2497-2502.

D'Argenio, D. A., M. W. Calfee, P. B. Rainey, and E. C. Pesci. 2002. Autolysis and autoaggregation in *Pseudomonas aeruginosa* colony morphology mutants. *J Bacteriol.* 184:6481-6489.

Decken, K., G. Kohler, K. Palmer-Lehmann, A. Wunderlin, F. Mattner, J. Magram, M. K. Gately, G. Alber. 1998. Interleukin-12 is essential for a protective Th1 response in mice infected with *Cryptococcus neoformans. Infect. Immun.* 66:4994.

DeMaria, A., H. Buckley, and F. von Lichtenberg. 1976. Gastrointestinal candidiasis in rats treated with antibiotics, cortisone, and azathioprine. *Infect. Immun.* 13:1761-1770.

Deng, J. C., K. Tateda, X. Zeng, and T. J. Standiford. 2001. Transient transgenic expression of gamma interferon promotes *Legionella pneumophila* clearance in immunocompetent hosts. *Infect. Immun.* 69:6382-6390.

Deng, J. C., X. Zeng, M. W. Newstead, T. A. Moore, W. C. Tsai, V. J. Thannickal, and T. J. Standiford. 2004. STAT4 is a critical mediator of early innate immune responses against pulmonary *Klebsiella* infection. *J Immunol* 173:4075-4083.

Egeter O., Mocikat R, Ghoreschi K, Dieckmann A, Rocken M. 2000. Eradication of disseminated lymphomas with CpG-DNA activated T helper type 1 cells from nontransgenic mice. *Cancer Res*. Mar. 15;60(6):1515-20.

Eigelsbach, H., J. Tulis, E. Overholt, and W. Griffith. 1961. Aerogenic immunization of the monkey and guinea pig with live tularemia vaccine. *Proc. Soc. Exp. Biol. Med.* 108:732-734.

Ekenna, O., and R. J. Sherertz. 1987. Factors affecting colonization and dissemination of *Candida albicans* from the gastrointestinal tract of mice. *Infect. Immun.* 55:1558-1563.

Elkins K L, Cowley S C, Bosio C M. Innate and adaptive immune responses to an intracellular bacterium, *Francisella tularensis* live vaccine strain. *Microbes Infect.* 2003;5:135-42.

Elkins, K. L., T. R. Rhinehart-Jones, S. Stibitz, J. S. Conover, and D. M. Klinman. 1999. Bacterial DNA containing CpG motifs stimulates lymphocyte-dependent protection of mice against lethal infection with intracellular bacterial. *J. Immunol.* 162:2291-2298.

Faden et al, "Pharmacological strategies in CNS trauma", *Trends Pharmacol. Sci.* 13(1):29-35 (1992)

Faden, A. I., "Experimental neurobiology of central nervous system trauma", *Crit. Rev. Neurobiol.* 7(3-4):175-186 (1993)

Ferens, W. A., and G. A. Bohach. 2000. Persistence of *S. aureus* on mucosal membranes: superantigens and internalization by host cells. *J. Lab. Clin. Med.* 135:225-230.

Ferlazzo, G., B. Morandi, A. D'Agostino, R. Meazza, G. Melioli, A. Moretta, and L. Moretta. 2003. The interaction between NK cells and dendritic cells in bacterial infections results in rapid induction of NK cell activation and in the lysis of uninfected dendritic cells. *Eur. J. Immunol.* 33:306-313.

Ferrero, E., P. Biswas, K. Vettoretto, M. Ferrarini, M. Uguccioni, L. Piali, B. E. Leone, B. Moser, C. Rugarli, and R. Pardi. 2003. Macrophages exposed to *Mycobacterium tuberculosis* release chemokines able to recruit selected leukocyte subpopulations: focus on gammadelta cells. *Immunology* 108:365.

Flesch, I. E., G. Schwamberger, S. H. Kaufmann. 1989. Fungicidal activity of IFN-γ-activated macrophages: extracellular killing of *Cryptococcus neoformans. J. Immunol.* 142:3219.

Frank, I., Pope, M. 2002. The enigma of dendritic cell-immunodeficiency virus interplay. *Curr. Mol. Med.* 2,229-236

Galperin, M. Y. 2004. Bacterial signal transduction network in a genomic perspective. *Environ Microbiol.* 6:552-567.

Galperin, M. Y., A. N. Nikolskaya, and E. V. Koonin. 2001. Novel domains of the prokaryotic two-component signal transduction systems. *FEMS Microbiol Lett.* 203:11-21.

Garbi N, Arnold B, Gordon S, Hammerling G J, Ganss R. 2004. CpG motifs as proinflammatory factors render autochthonous tumors permissive for infiltration and destruction. *J Immunol. May* 15;172(10):5861-9

Garzino-Demo, A., DeVico, A. L., Conant, K. E. and Gallo, R. C. 2000. The role of chemokines in human immunodeficiency virus infection. *Immunol Rev* 177:79-87.

Gawlick U, Kranz D M, Schepkin V D, Roy E J. 2004. A conjugate of a tumor-targeting ligand and a T cell costimulatory antibody to treat brain tumors. *Bioconjug Chem.* Sep.-Oct.;15(5):1137-45.

Gigliotti, F., and W. T. Hughes. 1988. Passive immunoprophylaxis with specific monoclonal antibody confers partial protection against *Pneumocystis carinii* pneumonitis in animal models. *J. Clin. Investig.* 81:1666-1668.

Gigliotti, F., B. A. Garvy, and A. G. Harmsen. 1996. Antibody-mediated shift in the profile of glycoprotein A phenotypes observed in a mouse model of *Pneumocystis carinii* pneumonia. *Infect. Immun.* 64:1892-1899.

Goebeler, M., K. Kilian, R. Gillitzer, M. Kunz, T. Yoshimura, E.-B. Brocker, U. R. Rapp, and S. Ludwig. 1999. The MKK6/p38 stress kinase is critical for tumor necrosis-factor-alpha-induced expression of monocyte chemoattractant protein-1 in endothelial cells. *Blood* 93:857-865.

Gonzalez-Aseguinolaza, G., C. de Oliveira, M. Tomaska, S. Hong, O. Bruna-Romero, T. Nakayama, M. Taniguchi, A. Bendelac, L. Van Kaer, Y. Koezuka, and M. Tsuji. 2000. alpha-galactosylceramide-activated Valpha 14 natural killer T cells mediate protection against murine malaria. *Proc Natl Acad Sci USA* 97:8461.

Granucci, F., Vizzardelli, C., Pavelka, N., Feau, S., Persico, M., Virzi, E., Rescigno, M., Moro, G., Ricciardi-Castagnoli, P. 2001. Inducible IL-2 production by dendritic cells revealed by global gene expression analysis. *Nat. Immunol.* 2, 882-888.

Greenberger, M. J., S. L. Kunkel, R. M. Strieter, N. W. Lukacs, J. Bramson, J. Gauldie, F. L. Graham, M. Hitt, J. M. Danforth, and T. J. Standiford. 1996. IL-12 gene therapy protects mice in lethal *Klebsiella pneumonia*. *J. Immunol.* 157:3006-3012.

Gruet, P., P. Maincent, X. Berthelot, and V. Kaltsatos. 2001. Bovine mastitis and intramammary drug delivery: review and perspectives. *Adv. Drug Deliv. Rev.* 50:245-259.

Halpern, M. D., R. J. Kurlander, and D. S. Pisetsky. 1996. Bacterial DNA induced murine interferon-g production by stimulation of interleukin-12 and tumor necrosis factor-a. *Cell. Immunol.* 167:72-78.

Harmsen, A. G., and M. Stankiewicz. 1990. Requirement for CD4+ cells in resistance to *Pneumocystis carinii* pneumonia in mice. *J. Exp. Med.* 172:937-945.

Hayakawa, Y., R. Nagata, A. Hirata, M. Hyodo, and R. Kawai. 2003. A facile synthesis of cyclic bis(3'-5') diguanylic acid. *Tetrahedron* 59:6465-6471.

Hecht, G. B. and A. Newton. 1995. Identification of a novel response regulator required for the swarmer- to-stalked-cell transition in *Caulobacter crescentus*. *J. Bacteriol.* 177: 6223-6229.

Hickey, W. F. et al, "T-lymphocyte entry into the central nervous system", *J. Neurosci. Res.* 28(2):254-260 (1991)

Hill, J. O., A. G. Harmsen. 1991. Intrapulmonary growth and dissemination of an avirulent strain of *Cryptococcus neoformans* in mice depleted of CD4+ or CD8+ T cells. *J. Exp. Med.* 173:755.

Hirschberg et al, "Accumulation of passively transferred primed T cells independently of their antigen specificity following central nervous system trauma" *J. Neuroimmunol.* 89(1-2):88-96 (1998)

Hoag, K. A., M. F. Lipscomb, A. A. Izzo, and N. E. Street. 1997. IL-12 and IFN-gamma are required for initiating the protective Th1 response to pulmonary cryptococcosis in resistant C.B-17 mice. *Am. J. Respir. Cell Mol. Biol.* 17:733-739.

Horn, C. A., R. G. Washburn. 1995. Anticryptococcal activity of NK cell-enriched peripheral blood lymphocytes from human immunodeficiency virus-infected subjects: responses to interleukin-2, interferon-γ, and interleukin-12. *J. Infect. Dis.* 172:1023.

Hornick, R. B., and H. T. Eigelsbach. 1966. Aerogenic immunization of man with live tularemia vaccine. *Bacteriol. Rev.* 30:532-538.

Hovda et al, "Diffuse prolonged depression of cerebral oxidative metabolism following concussive brain injury in the rat: a cytochrome oxidase histochemistry study", *Brain Res.* 567(1):1-10 (1991)

Huffnagle, G. B., G. B. Toews, M. D. Burdick, M. B. Boyd, K. S. McAllister, R. A. McDonald, S. L. Kunkel, and R. M. Strieter. 1996. Afferent phase production of TNF-alpha is required for the development of protective T cell immunity to *Cryptococcus neoformans*. *J. Immunol.* 157:4529-4536.

Huffnagle, G. B., J. L. Yates, M. F. Lipscomb. 1991a. Immunity to a pulmonary *Cryptococcus neoformans* infection requires both CD4+ and CD8+ T cells. *J. Exp. Med.* 173: 793.

Huffnagle, G. B., J. L. Yates, M. F. Lipscomb. 1991b. T cell-mediated immunity in the lung: a *Cryptococcus neoformans* pulmonary infection model using SCID and athymic nude mice. *Infect. Immun.* 59:1423.

Huffnagle, G. B., M. B. Boyd, N. E. Street, and M. F. Lipscomb. 1998. IL-5 is required for eosinophil recruitment, crystal deposition, and mononuclear cell recruitment during a pulmonary *Cryptococcus neoformans* infection in genetically susceptible mice (C57BL/6). *J. Immunol.* 160: 2393-2400.

Huffnagle, G. B., M. F. Lipscomb, J. A. Lovchik, K. A. Hoag, N. E. Street. 1994. The role of CD4+ and CD8+ T cells in the protective inflammatory response to a pulmonary cryptococcal infection. *J. Leukocyte Biol.* 55:35.

Hussell, T., L. C. Spender, A. Georgiou, A. O'Garra, P. J. M. Openshaw. 1996. Th1 and Th2 cytokine induction in pulmonary T-cells during infection with respiratory syncytial virus. *J. Gen. Virol.* 77:2447.

Hyodo, M., and Y. Hayakawa. 2004. An improved method for synthesizing cyclic bis (3'5') diguanylic acid (-di-GMP). *Bull. Chem. Soc. Jpn.* 77:2089-2093.

Hyodo, M., Y. Hayakawa, and D. K. R. Karaolis. 2006. Organic Synthesis, Chemical Properties, and Biological Activities of Cyclic bis(3'-5') Diguanylic Acid (c-di-GMP) and Its Analogs. *J. Synth. Org. Chem., Jpn* 64:359.

Iijima, N., Y. Yanagawa, and K. Onoe. 2003. Role of early- or late-phase activation of p38 mitogen-activated protein kinase induced by tumour necrosis factor-alpha or 2,4-dinitrochlorobenzene during maturation of murine dendritic cells. *Immunology* 110:322-328.

Inohara, N., Y. Ogura, F. F. Chen, A. Muto, and G. Nunez. 2001. Human Nod1 confers responsiveness to bacterial lipopolysaccharides. *Journal of Biological Chemistry* 276: 2551-2554.

Isomura I, Yasuda Y, Tsujimura K, Takahashi T, Tochikubo K, Morita A. 2005. Recombinant cholera toxin B subunit activates dendritic cells and enhances antitumor immunity. *Microbiol Immunol.* 49(1):79-87.

Johnston, B., C. H. Kim, D. Soler, M. Emoto, and E. C. Butcher. 2003. Differential chemokine responses and homing patterns of murine TCR alpha beta NKT cell subsets. *J. Immunol.* 171:2960

Jones, H. A., J. W. Lillard, Jr., and R. D. Perry. 1999. HmsT, a protein essential for expression of the haemin storage (Hms+) phenotype of *Yersinia pestis*. *Microbiology* 145 (Pt 8):2117-2128.

Karaolis, D. K. R., K. Cheng, M. Lipsky, A. Elnabawi, J. Catalano, M. Hyodo, Y. Hayakawa, and J.-P. Raufman. 2005. 3',5'-Cyclic diguanylic acid (c-di-GMP) inhibits basal and growth factor-stimulated human colon cancer cell proliferation. *Biochemical and Biophysical Research Communications* 329:40-45.

Karaolis, D. K. R., M. H. Rashid, C. Rajanna, W. Luo, M. Hyodo, and Y. Hayakawa. 2005. c-di-GMP (3'-5'-cyclic diguanylic acid) inhibits *Staphylococcus aureus* cell-cell interactions and biofilm formation. *Antimicrobial Agents and Chemotherapy* 49:1029-1038.

Karaolis, D. K. R., M. H. Rashid, C. Rajanna, W. Luo, M. Hyodo, and Y. Hayakawa. 2005. c-di-GMP(3'-5'-cyclic diguanylic acid) inhibits *Staphylococcus aureus* cell-cell interactions and biofilm formation. *Antimicrob Agents Chemother.* 49:1029-38.

Karaolis, D. K. R., K. Cheng, M. Lipsky, A. Elnabawi, J. Catalano, M. Hyodo, Y. Hayakawa, and J. P. Raufman. 2005. 3',5'-cyclic diguanylic acid (c-di-GMP) inhibits basal and growth factor-stimulated human colon cancer cell proliferation. *Biochem. Biophys. Res. Comm.,* 329:40-45

Kaufman H L, Disis M L. 2004. Immune system versus tumor: shifting the balance in favor of DCs and effective immunity. *J Clin Invest. Mar.* ;113(5):664-7

Kawai R, Nagata R, Hirata A, Hayakawa Y. 2003. A new synthetic approach to cyclic bis(3'→5')diguanylic acid. *Nucleic Acids Res Suppl.* 3:103-4.

Kawakami, K., M. H. Qureshi, T. Zhang, Y. Koguchi, S. Yara, K. Takeda, S. Akira, M. Kurimoto, A. Saito. 2000. Involvement of endogenously synthesized interleukin (IL)-18 in the protective effects of IL-12 against pulmonary infection with *Cryptococcus neoformans* in mice. *FEMS Immunol. Med. Microbiol.* 27:191.

Kawakami, K., N. Yamamoto, Y. Kinjo, K. Miyagi, C. Nakasone, K. Uezu, T. Kinjo, T. Nakayama, M. Taniguchi, and A. Saito. 2003. Critical role of Valpha14+ natural killer T cells in the innate phase of host protection against *Streptococcus pneumoniae* infection. *Eur. J. Immunol.* 33:3322.

Kawakami, K., Y. Kinjo, S. Yara, Y. Koguchi, K. Uezu, T. Nakayama, M. Taniguchi, and A. Saito. 2001. Activation of Valpha14(+) natural killer T cells by alpha-galactosylceramide results in development of Th1 response and local host resistance in mice infected with *Cryptococcus neoformans*. *Infect. Immun.* 69:213.

Kawakami, K., Y. Koguchi, M. H. Qureshi, S. Yara, Y. Kinjo, A. Miyazato, A. Nishizawa, H. Nariuchi, A. Saito. 2000. Circulating soluble CD4 directly prevents host resistance and delayed-type hypersensitivity response to *Cryptococcus neoformans* in mice. *Microbiol. Immunol.* 44:1033.

Kikuchi, T., S. Andarini, H. Xin, K. Gomi, Y. Tokue, Y. Saijo, T. Honjo, A. Watanabe, and T. Nukiwa. Involvement of Fractalkine/CX3CL1 expression by dendritic cells in the enhancement of host immunity against *Legionella pneumophila*. 2005. 73:5350.

Klinman, D. M. 2003. CpG DNA as a vaccine adjuvant. *Expert Rev Vaccines* 2:305-15.

Kradin, R. L., H. Sakamoto, F. I. Preffer, D. Dombkowski, K. M. Springer, and C. P. Leary. 2000. Accumulation of macrophages with dendritic cell characteristics in the pulmonary response to *Listeria*. *Am. J. Respir. Crit. Care Med.* 161:535-542.

Kramer et al, "Gene transfer through the blood-nerve barrier: NGF-engineered neuritogenic T lymphocytes attenuate experimental autoimmune neuritis", *Nat. Med.* 1(11): 1162-1166 (1995)

Krieg AM. 2002. CpG motifs in bacterial DNA and their immune effects. *Annu Rev Immunol.* 20:709-60.

Kullberg, B. J., and S. G. Filler. 2002. Candidemia, p. 327-340. In R. A. Calderone (ed.), *Candida* and candidosis. *ASM Press*, Washington, D.C.

Lazarov Spiegler et al, "Transplantation of activated macrophages overcomes central nervous system regrowth failure", *FASEB J.* 10(11):1296-1302 (1996)

Lee, J. C. 1996. The prospects for developing a vaccine against *Staphylococcus aureus*. *Trends Microbiol.* 4:162-166.

Leiby D A, Fortier A H, Crawford R M, Schreiber R D, Nacy C A. In vivo modulation of the murine immune response to *Francisella tularensis* LVS by administration of anticytokine antibodies. *Infect Immun.* 1992;60:84-9.

Lentz, M. R. 1999. The role of therapeutic apheresis in the treatment of cancer: a review. *Ther Apher* 3:40-49.

Levitz, S. M. 1991. The ecology of *Cryptococcus neoformans* and the epidemiology of cryptococcosis. *Rev. Infect. Dis.* 13:1163.

Lin, Y. L., Y. C. Liang, S. S. Lee, and B. L. Chiang. 2005. Polysaccharide purified from *Ganoderma lucidum* induced activation and maturation of human monocyte-derived dendritic cells by the NF-kappaB and p38 mitogen-activated protein kinase pathways. *J Leukoc Biol.* 78:533-543.

Lipscomb, M. F., J. M. Onofrio, and E. J. Nash. 1983. A morphological study of the role of phagocytes in the clearance of *Staphylococcus aureus* from the lung. *J. Reticuloend. Soc.* 33:429-442.

Liu, C. H., Y. T. Fan, A. Dias, L. Esper, R. A. Corn, A. Bafica, F. S. Machado, and J. Aliberti. 2006. Cutting edge: dendritic cells are essential for in vivo IL-12 production and development of resistance against *Toxoplasma gondii* infection in mice. *J Immunol* 177:31-35.

Lowy, F. D. 2000. Is *S. aureus* an intracellular pathogen? *Trends Microbiol.* 8:341-343.

Lyke, N. 2004. ADP-ribosylating bacterial enzymes for the targeted control of mucosal tolerance and immunity. *Ann N Y Acad Sci* 1029:193-208.

Macpherson G, Milling S, Yrlid U, Cousins L, Turnbull E, Huang FP. 2004. Uptake of antigens from the intestine by dendritic cells. *Ann N Y Acad Sci.* Dec.;1029:75-82.

Mahfouz, T., and E. Anaissie. 2003. Prevention of fungal infections in the immunocompromised host. *Curr. Opin. Investig. Drugs* 4:974-990.

Martin et al, "Fine specificity and HLA restriction of myelin basic protein-specific cytotoxic T cell lines from multiple sclerosis patients and healthy individuals", *J. immunol.* 145(2):540-548 (1990)

Matsuyama, W., H. Kamohara, C. Galligan, M. Faure, and T. Yoshimura. 2003. Interaction of discoidin domain receptor 1 isoform b (DDR1b) with collagen activates p38 mitogen-activated protein kinase and promotes differentiation of macrophages. *FASEB J.* 17:1286-1288.

Mayer, R., P. Ross, H. Weinhouse, D. Amikam, G. Volman, P. Ohana, R. D. Calhoon, H. C. Wong, A. W. Emerick, and M. Benziman. 1991. Polypeptide composition of bacterial cyclic diguanylic acid-dependent cellulose synthase and the occurrence of immunologically crossreacting proteins in higher plants. *Proc Natl Acad Sci. USA* 88:5472-5476.

McCluskie, M. J. and Weeratna, R. D. 2001. Novel adjuvant systems. *Current Drug Targets-Infectious Disorders* 1:263-271.

McDevitt, D., T. Nanavaty, K. House-Pompeo, E. Bell, N. Turner, L. McIntire, T. J. Foster, and M. Hook. 1997. Characterization of the interaction between the *Staphylococcus aureus* clumping factor (ClfA) and fibrinogen. *European Journal of Biochemistry* 247:416-424.

McIntosh, T. K., "Novel pharmacologic therapies in the treatment of experimental traumatic brain injury: a review", *J. Neurotrauma* 10(3):215-261 (1993)

McWilliam, A. S., D. Nelson, J. A. Thomas, and P. G. Holt. 1994. Rapid dendritic cell recruitment is a hallmark of the acute inflammatory response at mucosal surfaces. *J. Exp. Med.* 179:1331-1336.

Meldrum, "Glutamate as a neurotransmitter in the brain: review of physiology and pathology", *J. Nutr.* 130: (4S Suppl):1007s-1015S (2000)

Michie, C. A. 2002. Staphylococcal vaccines. *Trends Immmunol.* 23:461-463.

Mody, C. H., C. L. Tyler, R. G. Sitrin, C. Jackson, G. B. Toews. 1991. Interferon-γ activates rat alveolar macrophages for anticryptococcal activity. *Am. J. Respir. Cell Mol. Biol.* 5:19.

Mody, C. H., G. H. Chen, C. Jackson, J. L. Curtis, G. B. Toews. 1993. Depletion of murine CD8+ T cells in vivo decreases pulmonary clearance of a moderately virulent strain of *Cryptococcus neoformans*. *J. Lab. Clin. Med.* 121:765.

Moore, T. A., B. Moore, and T. J. Standiford. γδ-T cells are critical for survival and early proinflammatory cytokine gene expression during murine *Klebsiella pneumonia*. 2000. *J. Immunol.* 165:2643-6450.

Moore, T. A., M. L. Perry, A. G. Getsoian, M. W. Newstead, and T. J. Standiford. 2002. Divergent role of gamma interferon in a murine model of pulmonary versus systemic *Klebsiella pneumoniae* infection. *Infect. Immun.* 70:6310-6318.

Mullick, A., M. Elias, S. Picard, L. Bourget, O. Jovcevski, S. Gauthier, A. Tuite, P. Harakidas, C. Bihun, B. Massie, and P. Gros. 2004. Dysregulated inflammatory response to *C. albicans* in a C5-deficient mouse strain. *Infect. Immun.* 72:5868-5876.

Nakagawa, S., T. Ohtani, M. Mizuashi, Z. U. Mollah, Y. Ito, H. Tagami, and S. Aiba. 2004. p38 Mitogen-Activated protein kinase mediates dual role of ultraviolet B radiation in induction of maturation and apoptosis of monocyte-derived dendritic cells. *J. Invest. Dermatol.* 123:361-370.

Nelson, S., C. M. Mason, J. Kolls, and W. R. Summer. 1995. Pathophysiology of pneumonia. *Clin. Chest Med.* 16:1-12.

Netea M G, Brouwer A E, Hoogendoorn E H, Van der Meer J W, Koolen M, Verweij P E, Kullberg B J. 2004. Two patients with cryptococcal meningitis and idiopathic CD4 lymphopenia: defective cytokine production and reversal by recombinant interferon-gamma therapy. *Clin Infect Dis.* Nov. 1;39(9):e83-7.

O'Brien, S. N., N. M. Blijlevens, T. H. Mahfouz, and E. J. Anaissie. 2003. Infections in patients with hematological cancer: recent developments. *Hematology* 1:438-472.

Ota et al, "T-cell recognition of an immunodominant myelin basic protein epitope in multiple sclerosis", Nature 346 (6280):183-187 (1990)

Ouaaz, F., Arron, J., Zheng, Y., Choi, Y., Beg, A. A. 2002. Dendritic cell development and survival require distinct NF-α B subunits. *Immunity* 16,257-270.

Pappas, P. G., J. H. Rex, J. D. Sobel, S. G. Filler, W. E. Dismukes, T. J. Walsh, and J. E. Edwards. 2004. Guidelines for treatment of candidiasis. *Clin. Infect. Dis.* 38:161-189.

Parker, J. C., J. J. McCloskey, and K. A. Knauer. 1976. Pathobiologic features of human candidiasis. A common deep mycosis of the brain, heart and kidney in the altered host. *Am. J. Clin. Pathol.* 65:991-1000.

Pereira E F, Reinhardt-Maelicke S, Schrattenholz A, Maelicke A, Albuquerque EX. 1993. Identification and functional characterization of a new agonist site on nicotinic acetylcholine receptors of cultured hippocampal neurons. *J Pharmacol Exp Ther.* Jun.;265(3):1474-91.

Pette et al, "Myelin basic protein-specific T lymphocyte lines from MS patients and healthy individuals", *Proc. Natl. Acad. Sci. USA* 87(2):7968-7972 (1990)

Peyrottes S, Egron D, Lefebvre I, Gosselin G, Imbach J L, Perigaud C. 2004. SATE pronucleotide approaches: an overview. *Mini Rev Med Chem.* May;4(4):395-408.

Pitt et al., "Glutamate excitotoxicity in a model of multiple sclerosis", *Nat Med,* 6:67-70 (2000)

Portnoy, D. A. 1992. Innate immunity to a facultative intracellular bacterial pathogen. *Curr. Opin. Immunol.* 4:20-24.

Puig-Kroger, A., M. Relloso, O. Fernandez-Capetillo, A. Zubiaga, A. J. Silva, C. Bernabeu, and A. Corbi. 2001. Extracellular signal-regulated protein kinase signaling pathway negatively regulates the phenotypic and functional maturation of monocyte-derived human dendritic cells. *Blood* 98:2175-2182.

Quaranta M G, Mattioli B, Giordani L, Viora M. 2004. HIV-1 Nef equips dendritic cells to reduce survival and function of CD8+ T cells: a mechanism of immune evasion. *FASEB J.* Sep.;18(12):1459-61.

Rapalino et al, "Implantation of stimulated homologous macrophages results in partial recovery of paraplegic rats", *Nat. Med.* 4(7) :814-821 (1998)

Rashid, M. H., C. Rajanna, A. Ali, and D. K. R. Karaolis. 2003. Identification of genes involved in the switch between the smooth and rugose phenotypes of Vibrio cholerae. *FEMS Microbiol. Letts.* 227:113-119.

Redlinger R E Jr, Shimizu T, Remy T, Alber S, Watkins S C, Barksdale E M Jr. 2003. Cellular mechanisms of interleukin-12-mediated neuroblastoma regression. *J Pediatr Surg.* February;38(2) :199-204.

Rex, J. H., T. J. Walsh, and E. J. Anaissie. 1998. Fungal infections in iatrogenically compromised hosts. *Adv. Intern. Med.* 43:321-371

Rimoldi M, Chieppa M, Vulcano M, Allavena P, Rescigno M. 2004. Intestinal epithelial cells control dendritic cell function. *Ann N Y Acad Sci. Dec.;*1029:66-74.

Romagnani, P., F. Annunziato, E. Lazzeri, L. Cosmi, C. Beltrame, L. Lasagni, G. Galli, M. Francalanci, R. Manetti, F. Marra, V. Vanini, E. Maggi, and S. Romagnani. 2001. Interferon-inducible protein 10, monokine induced by interferon gamma, and interferon-inducible T-cell alpha chemoattractant are produced by thymic epithelial cells and attract T-cell receptor (TCR) alphabeta+ CD8+ single-positive T cells, TCRgammadelta+ T cells, and natural killer-type cells in human thymus. *Blood* 97:601.

Römling, U., and D. Amikam. 2006. Cyclic di-GMP as a second messenger. *Curr. Opin. Microbiol.* 2:218-228.

Römling, U., M. Gomelsky, and M. Y. Galperin. 2005. C-di-GMP: the dawning of a novel bacterial signalling system. *Mol Microbiol.* 57:629-639.

Römling, U., M. Rohde, A. Olsen, S. Normark, and J. Reinkoster. 2000. AgfD, the checkpoint of multicellular and aggregative behaviour in *Salmonella typhimurium* regulates at least two independent pathways. *Mol Microbiol.* 36:10-23.

Ross, P., H. Weinhouse, Y. Aloni, D. Michaeli, P. Weinberger-Ohana, R. Mayer, S. Braun, E. de Vroom, G. A. van der Marel, J. H. van Boom, and M. Benziman. 1987. Regulation of cellulose synthesis in *Acetobacter xylinum* by cyclic diguanylic acid. *Nature* 325:279-281.

Ross, P., R. Mayer, and M. Benziman. 1991. Cellulose biosynthesis and function in bacteria. *Microbiol Rev.* 55:35-58.

Ross, P., R. Mayer, H. Weinhouse, D. Amikam, Y. Huggirat, M. Benziman, E. de Vroom, A. Fidder, P. de Paus, L. A. Sliedregt, and et al. 1990. The cyclic diguanylic acid regulatory system of cellulose synthesis in *Acetobacter xylinum*. Chemical synthesis and biological activity of cyclic nucleotide dimer, trimer, and phosphothioate derivatives. *J Biol Chem.* 265:18933-18943.

Ross, P., Y. Aloni, C. Weinhouse, D. Michaeli, P. Weinberger-Ohana, R. Meyer, and M. Benziman. 1991. An unusual guanyl oligonucleotide regulates cellulose synthesis in *Acetobacter xylinum. FEBS Letters* 186:191-197.

Roths, J. B., and C. L. Sidman. 1993. Single and combined humoral and cell-mediated immunotherapy of *Pneumocystis carinii* pneumonia in immunodeficient scid mice. *Infect. Immun.* 61:1641-1649.

Saccani, S., S. Pantano, Natoli, and Gioacchino. 2002. p38-dependent marking of inflammatory genes for increased NF-kB recruitment. *Nature Immunol.* 3:69-75.

Sallusto F, Lanzavecchia A. 1994. Efficient presentation of soluble antigen by cultured human dendritic cells is maintained by granulocyte/macrophage colony-stimulating factor plus interleukin 4 and downregulated by tumor necrosis factor alpha. *J Exp Med.* Apr. 1;179(4):1109-18.

Sallusto, F., Palermo, B., Lenig, D., Miettinen, M., Matikainen, S., Julkunen, I., Forster, R., Burgstahler, R., Lipp, M., Lanzavecchia, A. 1999. Distinct patterns and kinetics of chemokine production regulate dendritic cell function. *Eur. J. Immunol.* 29,1617-1625.

Samonis, G., and D. Bafaloukos. 1992. Fungal infections in cancer patients: an escalating problem. *In Vivo* 6:183-193.

Samonis, G., N. C. Karyotakis, E. J. Anaissie, E. Barbounakis, S. Maraki, Y. Tselentis, and G. P. Bodey. 1996. Effects of cyclophosphamide and ceftriaxone on gastrointestinal colonization of mice by *Candida albicans. Antimicrob. Agents Chemother.* 40:2221-2223.

Sandovsky-Losica, H., L. Barr-Nea, and E. Segal. 1992. Fatal systemic candidiasis of gastrointestinal origin: an experimental model in mice compromised by anti-cancer treatment. *J. Med. Vet. Mycol.* 30:219-231.

Scandella E, Men Y, Gillessen S, Forster R, Groettrup M. 2002. Prostaglandin E2 is a key factor for CCR7 surface expression and migration of monocyte-derived dendritic cells. *Blood.* Aug. 15;100(4):1354-61.

Schluesener et al, "Autoaggressive T lymphocyte lines recognizing the encephalitogenic region of myelin basic protein: in vitro selection from unprimed rat T lymphocyte populations", *J. Immunol.* 135(5);3128-3133 (1985)

Schmidt, A. J., D. A. Ryjenkov, and M. Gomelsky. 2005. The ubiquitous protein domain EAL is a cyclic diguanylate-specific phosphodiesterase: Enzymatically active and inactive EAL domains. *J. Bacteriol.* 187:4774-4781.

Schoepp et al., "Pharmacological agents acting at subtypes of metabotropic glutamate receptors", *Neuropharmacology,* 38:1431-76 (1999)

Schroeder, J. T., A. P. Bieneman, H. Xiao, K. L. Chichester, and M. C. Liu. 2005. TLR9- and FceRI-mediated responses oppose one another in plasmacytoid dendritic cells by down-regulating receptor expression. *J. Immunol.* 175:5724-5731.

Sewell, A. K., Price, D. A. 2001. Dendritic cells and transmission of HIV-1. *Trends Immunol.* 22,173-175.

Shellito, J., V. V. Suzara, W. Blumenfeld, J. M. Beck, H. J. Steger, and T. H. Ermak. 1990. A new model of *Pneumocystis carinii* infection in mice selectively depleted of helper T lymphocytes. *J. Clin. Investig.* 85:1686-1693.

Shimizu T, Berhanu A, Redlinger R E Jr, Watkins S, Lotze M T, Barksdale E M Jr. 2001. Interleukin-12 transduced dendritic cells induce regression of established murine neuroblastoma. *J Pediatr Surg.* Aug.;36(8):1285-92.

Shkreta, L., B. G. Talbot, M. S. Diarra, and P. Lacasse. 2004. Immune responses to a DNA/protein vaccination strategy against *Staphylococcus aureus* induced mastitis in dairy cows. *Vaccine* 23:114-126.

Shutt, D. C., Daniels, K. J., Carolan, E. J., Hill, A. C., Soll, D. R. 2000. Changes in the motility, morphology, and F-actin architecture of human dendritic cells in an in vitro model of dendritic cell development. *Cell Motil. Cytoskeleton* 46, 200-221.

Sjöstedt, A. 2003. Virulence determinants and protective antigens of *Francisella tularensis. Curr. Opin. Microbiol.* 6:66-71.

Skerrett, S. J., and T. R. Martin. 1994. Intratracheal interferon-gamma augments pulmonary defenses in experimental legionellosis. *Am. J. Resp. Crit. Care Med.* 149:50-58.

Stoll G, Jander S, Schroeter M. 2000. Cytokines in CNS disorders: neurotoxicity versus neuroprotection. *J Neural Transm Suppl.* 59:81-9.

Streilein, J. W., "Immune privilege as the result of local tissue barriers and immunosuppressive microenvironments", *Curr. Opin. Immunol.* 5(3):428-423 (1993)

Streilein, J. W., "Unraveling immune privilege", *Science* 270 (5239):1158-1159 (1995)

Swartz, M. 2003. Neuroprotection as a treatment for glaucoma: pharmacological and immunological approaches. *Eur J Ophthalmol.* Apr.;13 Suppl 3:S27-31.

Swartz, M. 2004. Vaccination for glaucoma: dream or reality? *Brain Res Bull.* Feb. 15;62(6):481-4.

Tal, R., H. C. Wong, R. Calhoon, D. Gelfand, A. L. Fear, G. Volman, R. Mayer, P. Ross, D. Amikam, H. Weinhouse, A. Cohen, S. Sapir, P. Ohana, and M. Benziman. 1998. Three cdg operons control cellular turnover of cyclic di-GMP in *Acetobacter xylinum*: genetic organization and occurrence of conserved domains in isoenzymes. *Journal of Bacteriol.* 180:4416-4425.

Taniguchi, M., M. Harada, S. Kojo, T. Nakayama, and H. Wakao. 2003. The regulatory role of Valpha14 NKT cells in innate and acquired immune response. *Ann. Rev. Immunol.* 21:483.

Tateda, K., T. A. Moore, J. C. Deng, M. W. Newstead, X. Zeng, A. Matsukawa, M. S. Swanson, K. Yamaguchi, and T. J. Standiford. 2001. Early recruitment of neutrophils determines subsequent T1/T2 host responses in a murine model of *Legionella pneumophila* pneumonia. *J. Immunol.* 166:3355-3361.

Tateda, K., T. Matsumoto, Y. Ishii, N. Furuya, A. Ohno, S. Miyazaki, and K. Yamaguchi. 1998. Serum cytokines in patients with *Legionella pneumonia*: relative predominance of Th1-type cytokines. *Clin. Diag. Lab. Immunol.* 5:401.

Toews, G. B., G. N. Gross, and A. K. Pierce. 1980. The relationship of inoculum size to lung bacterial clearance and phagocytic cell response in mice. *Am. Rev. Respir. Dis.* 120:559-566.

Tomioka H. 2004. Adjunctive immunotherapy of mycobacterial infections. *Curr Pharm Des.* 10(26):3297-312.

Tsai, W. C., R. M. Strieter, B. Mehrad, M. W. Newstead, X. Zeng, and T. J. Standiford. 2000. CXC chemokine receptor CXCR2 is essential for protective innate host response in murine *Pseudomonas aeruginosa* pneumonia. *Infect. Immun.* 68:289-296.

Tuite, A., A. Mullick, and P. Gros. 2004. Genetic analysis of innate immunity in resistance to *Candida albicans. Genes Immun.* 5:576-587.

Vives E, Dell'Aquila C, Bologna J C, Morvan F, Rayner B, Imbach J L. 1999. Lipophilic pro-oligonucleotides are rapidly and efficiently internalized in HeLa cells. *Nucleic Acids Res*. Oct. 15;27(20):4071-6.

Weigel B J, Rodeberg D A, Krieg A M, Blazar B R. 2003. CpG oligodeoxynucleotides potentiate the antitumor effects of chemotherapy or tumor resection in an orthotopic murine model of rhabdomyosarcoma. *Clin Cancer Res*. Aug. 1;9 (8):3105-14.

Werkele, H., in The Blood-Brain Barrier, Pardridge, Ed., Raven Press, Ltd. New York, pp. 67-85 (1993)

Wingard, J. R., J. D. Dick, W. G. Merz, G. R. Sandford, R. Saral, and W. H. Burns. 1982. Differences in virulence of clinical isolates of *Candida tropicalis* and *Candida albicans* in mice. *Infect. Immun.* 37:833-836.

Wingard, J. R., J. D. Dick, W. G. Merz, G. R. Sandford, R. Saral, and W. H. Burns. 1980. Pathogenicity of *Candida tropicalis* and *Candida albicans* after gastrointestinal inoculation in mice. *Infect. Immun.* 29:808-813.

Wu, D. et al, *J. Neurochem.* 62:37-44 (1994) Yang, D., Q. Chen, Y. Le, J. M. Wang, and J. J. Oppenheim. 2001. Differential regulation of formyl peptide receptor-like 1 expression during the differentiation of monocytes to dendritic cells and macrophages. *J. Immunol.* 166:4092-4098.

Yoshida, K., T. Matsumoto, K. Tateda, K. Uchida, S. Tsujimoto, Y. Iwakurai, and K. Yamaguchi. 2001. Protection against pulmonary infection with *Klebsiella pneumoniae* in mice by interferon-gamma through activation of phagocytic cells and stimulation of production of other cytokines. *J. Med. Microbiol.* 50:959.

Yoshimura, T., and A. Ueda. 1996. Monocyte chemoattractant protein-1. In Human Cytokines: Handbook for Basic and Clinical Research. B. B. Aggarwal, and J. U. Gutterman, eds. Blackwell Science, Cambridge, Mass., p. 198-221.

Yoshina, A. et al, *Brain Res.* 561:106-119 (1991)

Yu, Q., C. Kovacs, F. Y. Yue, and M. A. Ostrowski. 2004. The role of the p38 mitogen-activated protein kinase, extracellular signal-regulated kinase, and phosphoinositide-3-OH kinase signal transduction pathways in CD40 ligand-induced dendritic cell activation and expansion of virus-specific CD8+ T cell memory responses. *J. Immunol.* 172:6047-6056.

Yuan, R. R., A. Casadevall, J. Oh, M. D. Scharff. 1997. T cells cooperate with passive antibody to modify *Cryptococcus neoformans* infection in mice. *Proc. Natl. Acad. Sci. USA* 94:2483.

Zelenay, S., Elias, F. and Flo, J. 2003. Immunostimulatory effects of plasmid DNA and synthetic oligonucleotides. *Eur J Immunol* 33:1382-92.

Zeng, X., T. A. Moore, M. W. Newstead, J. C. Deng, S. L. Kunkel, A. D. Luster, and T. J. Standiford. 2005. IP-10, but not MIG, promotes protective type 1 immunity in murine *Klebsiella pneumonia. Infect. Immun.* 73:8226-36-8236.

Zhang D, Yang X, Lu H, Zhong G, Brunham RC. 1999. Immunity to *Chlamydia trachomatis* mouse pneumonitis induced by vaccination with live organisms correlates with early granulocyte-macrophage colony-stimulating factor and interleukin-12 production and with dendritic cell-like maturation. *Infect Immun*. Apr.;67(4):1606-13.

Zivin et al, "Stroke therapy", *Sci. Am.* 265(1):56-63 (1991)

What is claimed is:

1. A method for inhibiting or treating an immunological or inflammatory disorder or disease, comprising administering an effective amount of cyclic di-GMP or a cyclic dinucleotide analogue thereof to a patient, thereby stimulating or enhancing the immune or inflammatory response in the patient.

2. The method of claim 1, wherein the immunological or inflammatory disorder or disease is selected from the group consisting of arthritis, cancer, an autoimmune disorder or disease, a chronic infectious disease, an infectious disease in which the pathogen or toxin produced impairs the immune response, and an immunodeficiency disease or disorder.

3. The method of claim 1, wherein the immunological or inflammatory disorder or disease is an infectious disease.

4. The method of claim 3, wherein the infectious disease is caused by a fungi.

5. The method of claim 4, wherein the fungi is a *Cryptococcus* spp.

6. The method of claim 5, wherein the *Cryptococcus* species is *Cryptococcus neoformans*.

7. The method of claim 4, wherein the fungi is *Candida albicans*.

8. The method of claim 4, wherein the fungi is *Pneumocystis carinii*.

9. The method of claim 4, wherein the fungi is selected from the group consisting of *Histoplasma* spp., *Blastomyces* spp. and *Coccidioides* spp.

10. The method of claim 3, wherein the infectious disease is caused by a virus.

11. The method of claim 10, wherein the virus is a respiratory virus which causes an upper respiratory tract viral infection.

12. The method of claim 11, wherein the virus is an influenza virus.

13. The method of claim 3, wherein the infectious disease is caused by a bacteria.

14. The method of claim 13, wherein the bacteria is *Klebsiella pneumoniae*.

15. The method of claim 13, wherein the bacteria is *Francisella tularensis*.

16. The method of claim 13, wherein the infectious disease is secondary pneumonia following an upper respiratory tract viral infection.

17. The method of claim 16, wherein the bacteria is selected from the group consisting of *Haemophilus influenza, Staphylococcus aureus, Streptococcus pyogenes, Mycoplasma pneumoniae*, and *Streptococcus pneumoniae*.

18. A method for enhancing an immune response to a vaccine, comprising administering an effective amount of a cancer vaccine or antigen to a patient in need thereof in combination with an effective amount of cyclic di-GMP or a cyclic dinucleotide analogue thereof.

19. The method of claim 18, wherein the immune response is a cellular response.

20. The method of claim 18, wherein the cancer vaccine is an autologous cancer vaccine.

21. The method of claim 18, wherein the cancer vaccine is an allogeneic cancer vaccine.

22. A method for treating asthma, comprising administering an effective amount of cyclic di-GMP or a cyclic dinucleotide analogue thereof to a patient in need thereof to inhibit or treat asthma.

23. The method of claim 22, wherein an effective amount of cyclic di-GMP is administered to the patient in need thereof.

24. The method of claim 22, wherein an effective amount of a cyclic dinucleotide analogue of cyclic di-GMP is administered to the patient in need thereof.

25. The method of claim 24, wherein said cyclic dinucleotide analogue is selected from the group consisting of cyclic dinucleotide compounds (I)-(XX)

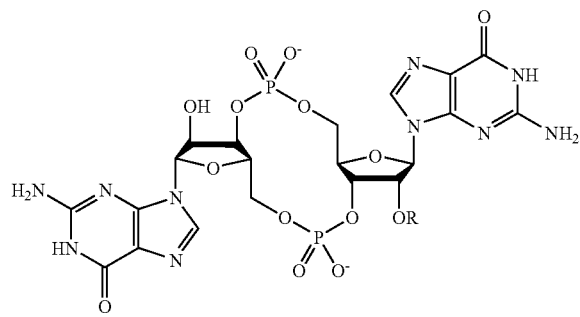

(III)
c-G(2'-OR)pGp
R = CH$_3$, C$_2$H$_5$, etc

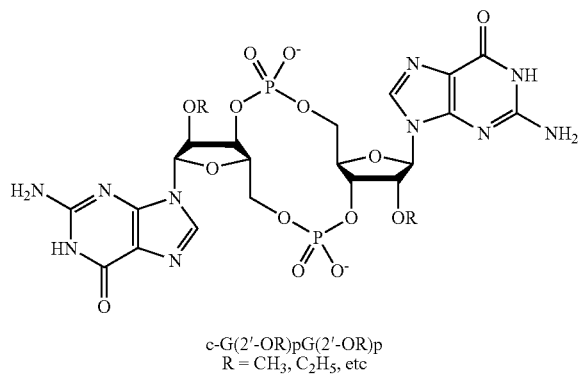

(IV)
c-G(2'-OR)pG(2'-OR)p
R = CH$_3$, C$_2$H$_5$, etc

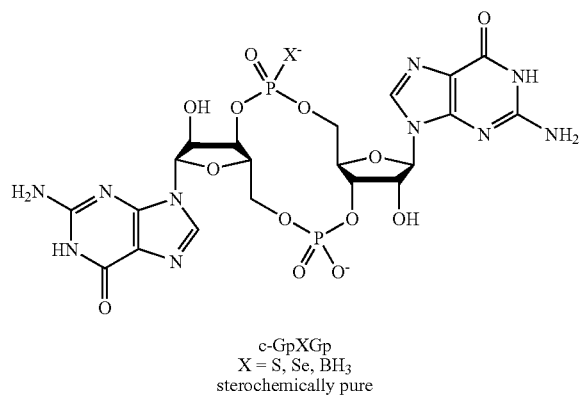

(V)
c-GpXGp
X = S, Se, BH$_3$
sterochemically pure

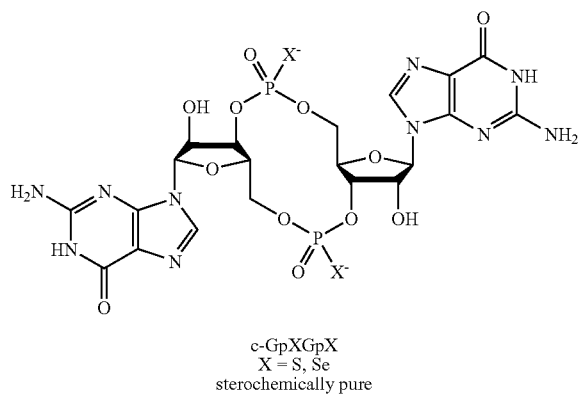

(VI)
c-GpXGpX
X = S, Se
sterochemically pure

-continued
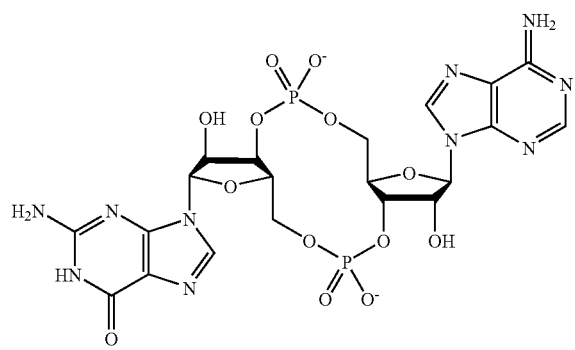
(VII) c-GpAp
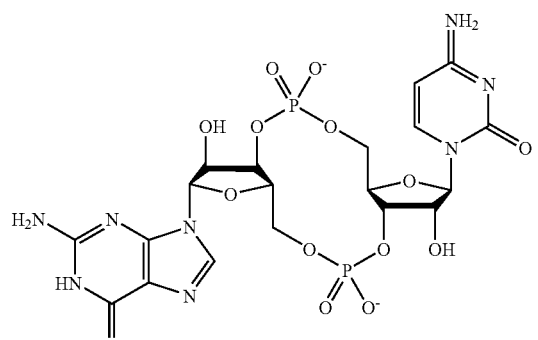
(VIII) c-GpCp
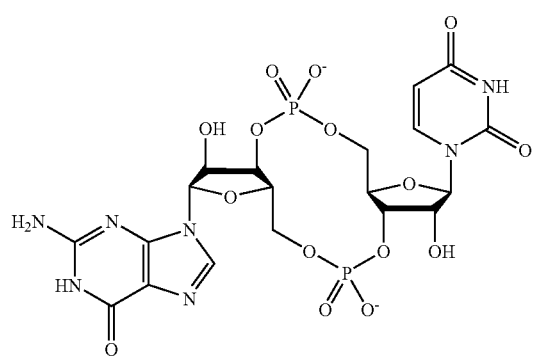
(IX) c-GpUp
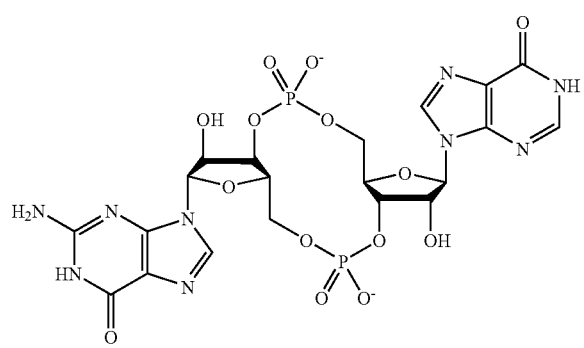
(X) c-GpIp
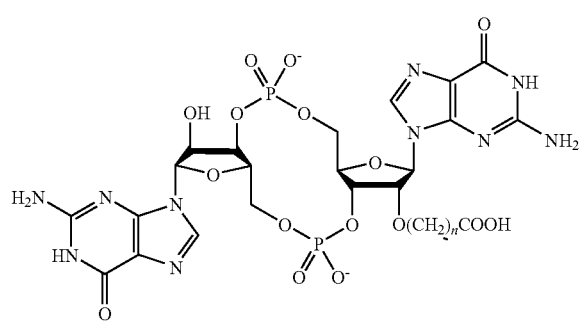
(XI)
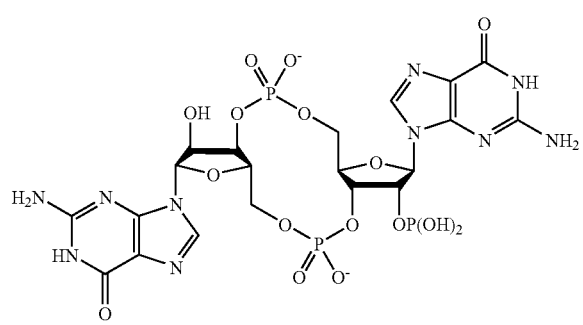
(XII)
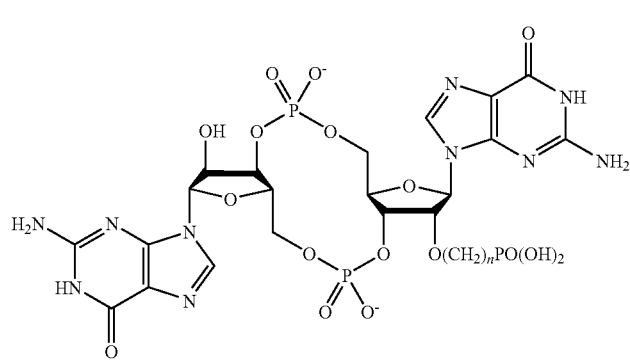
(XIII)

-continued
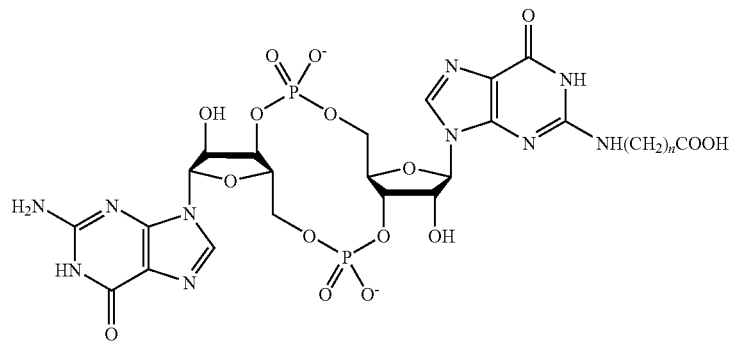
(XIV)
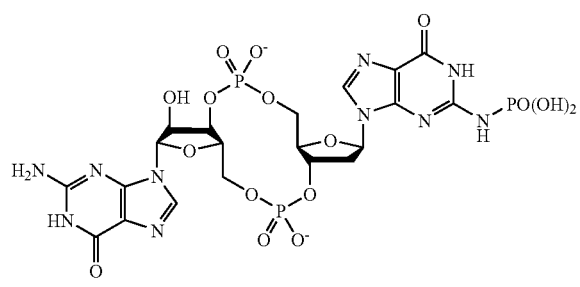
(XV)
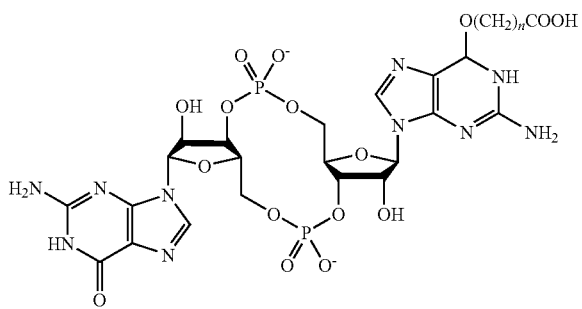
(XVI)
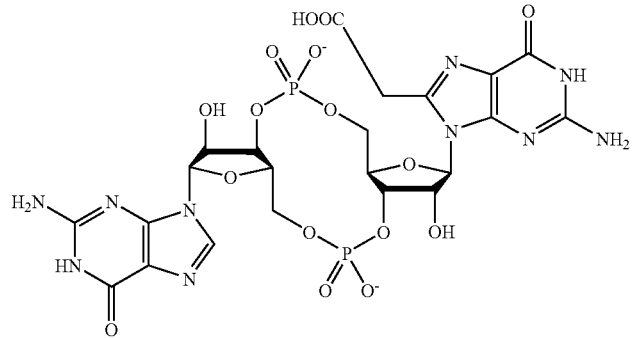
(XVII)
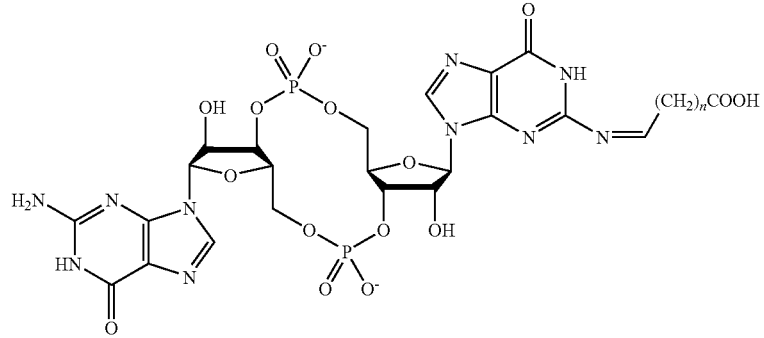
(XVIII)

-continued

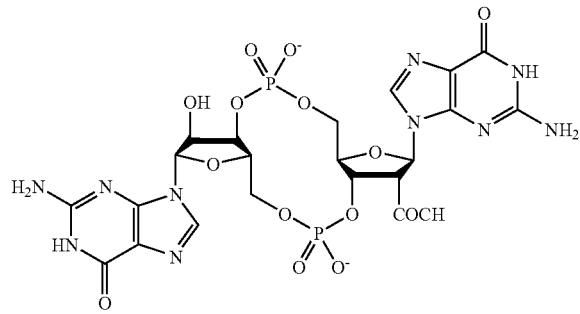
(XIX)

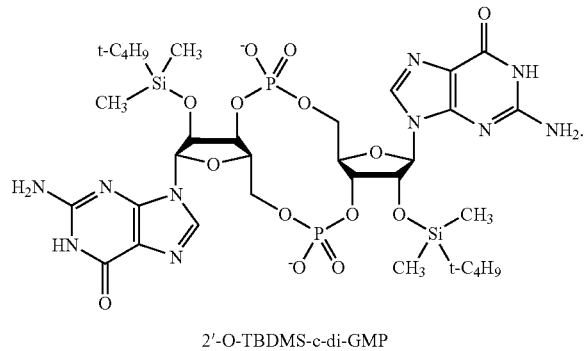
(XX)

2'-O-TBDMS-c-di-GMP

26. A method for stimulating or enhancing an immune response in a patient, comprising:
    activating dendritic cells or T cells with an antigen and with cyclic di-GMP or a cyclic dinucleotide analogue thereof; and
    administering the activated dendritic cells or T cells as a cellular vaccine to stimulate or enhance an immune response in the patient.

27. The method of claim 26, wherein said cyclic dinucleotide analogue is selected from the group consisting of cyclic dinucleotide compounds (I)-(XX)

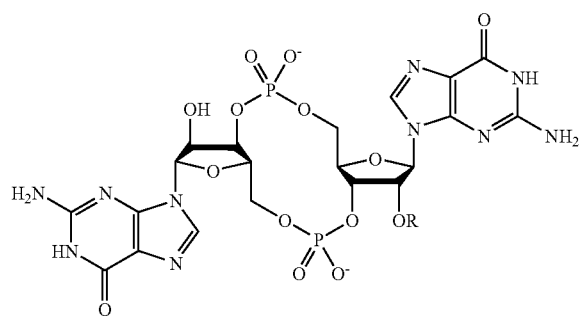
(III)

c-G(2'-OR)pGp
R = CH$_3$, C$_2$H$_5$, etc

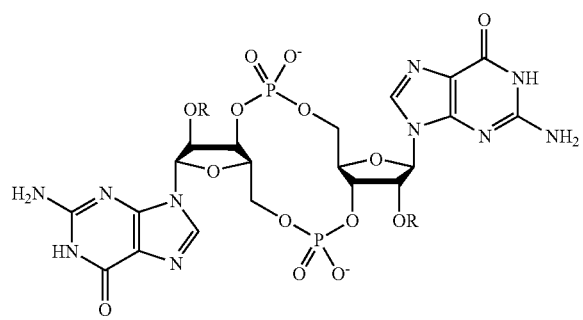
(IV)

c-G(2'-OR)pG(2'-OR)p
R = CH$_3$, C$_2$H$_5$, etc

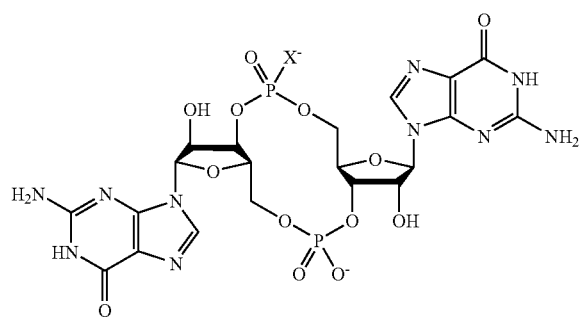
(V)

c-GpXGp
X = S, Se, BH$_3$
sterochemically pure

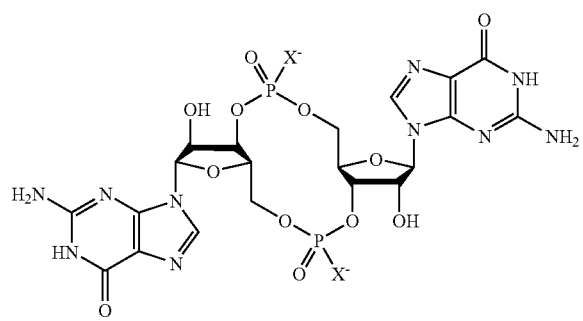
(VI)

c-GpXGpX
X = S, Se
sterochemically pure

-continued
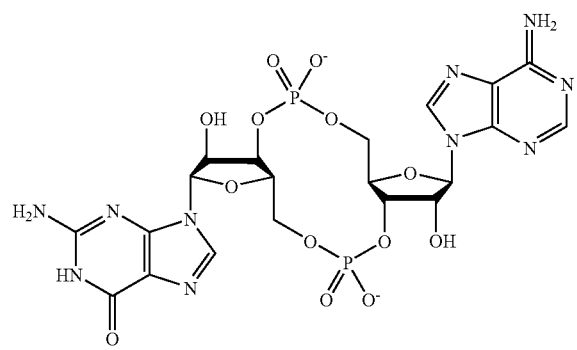
c-GpAp (VII)
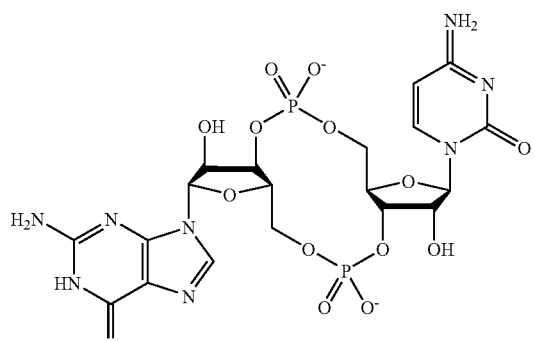
c-GpCp (VIII)
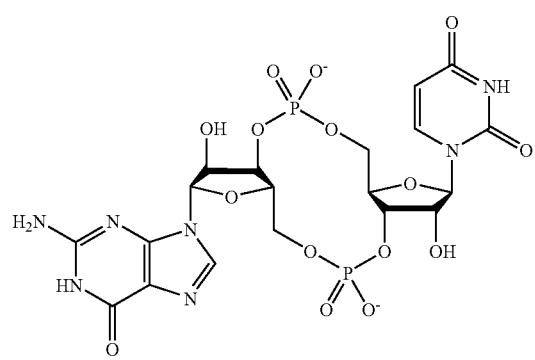
c-GpUp (IX)
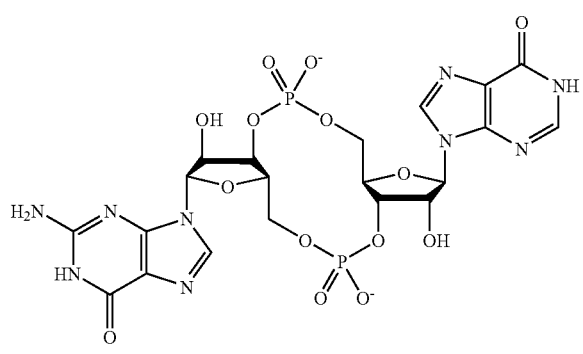
c-GpIp (X)
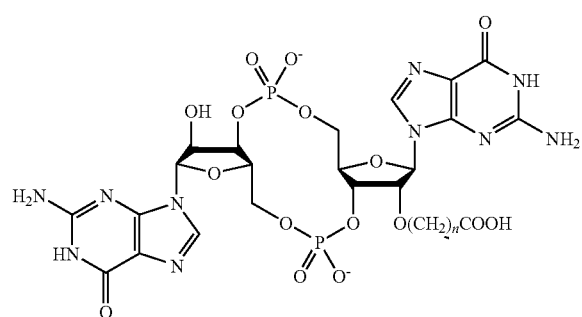
(XI)
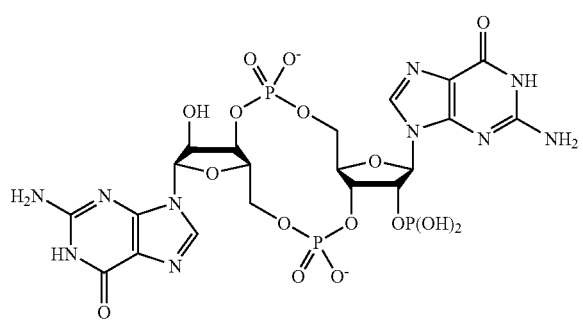
(XII)
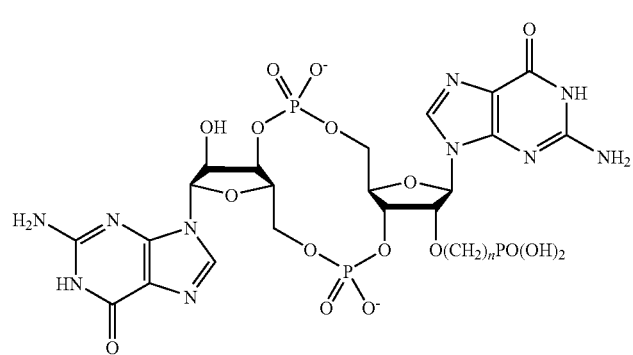
(XIII)

-continued
(XIV)
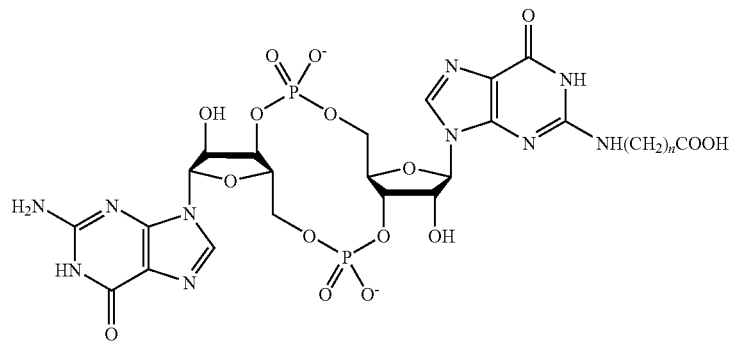
(XV)
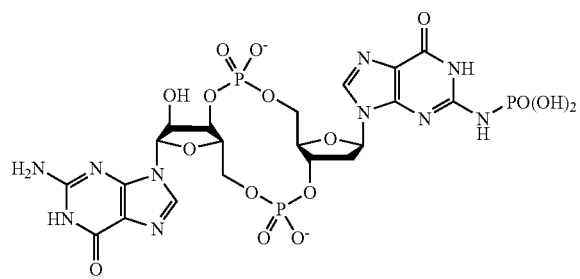
(XVI)
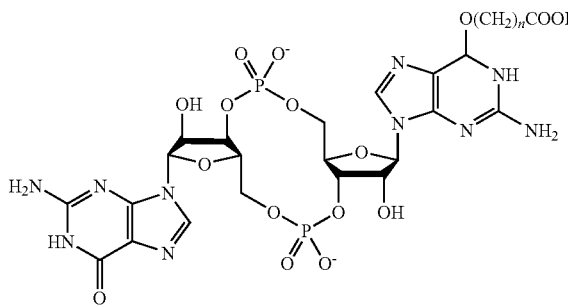
(XVII)
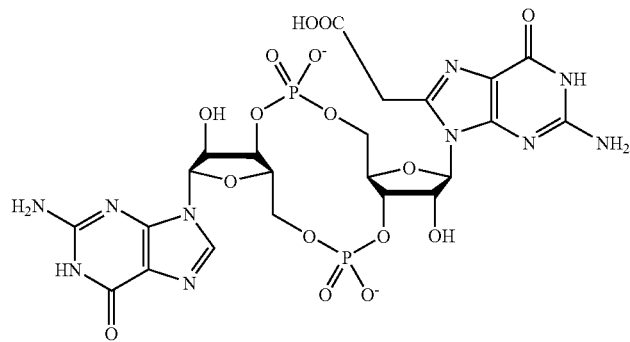
(XVIII)
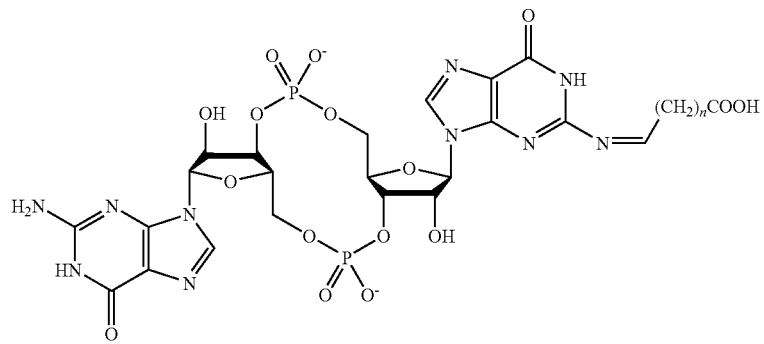

-continued
(XIX)
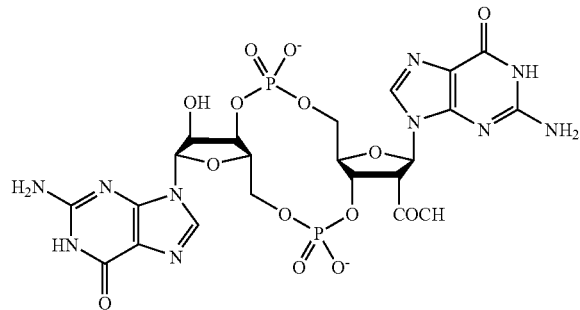
(XX)
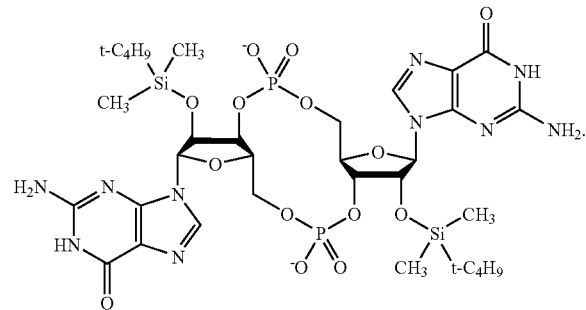
2'-O-TBDMS-c-di-GMP
28. The method of claim 18, wherein said cyclic dinucleotide analogue is selected from the group consisting of cyclic dinucleotide compounds (I)-(XX)
(III)
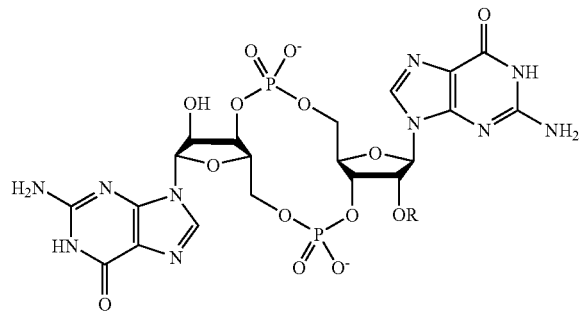
c-G(2'-OR)pGp
R = $CH_3$, $C_2H_5$, etc
(IV)
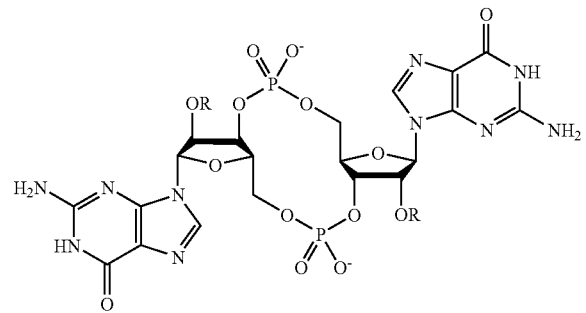
c-G(2'-OR)pG(2'-OR)p
R = $CH_3$, $C_2H_5$, etc
(V)
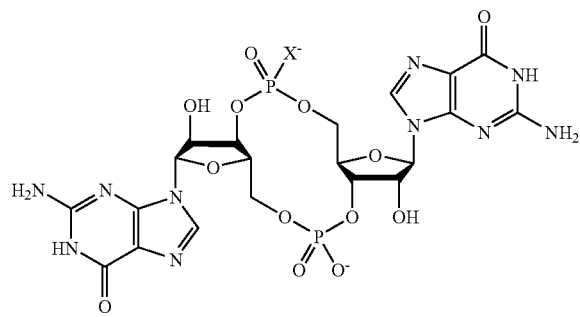
c-GpXGp
X = S, Se, $BH_3$
sterochemically pure
(VI)
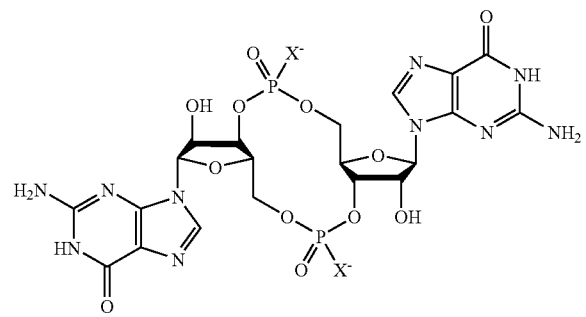
c-GpXGpX
X = S, Se
sterochemically pure -continued
(VII)
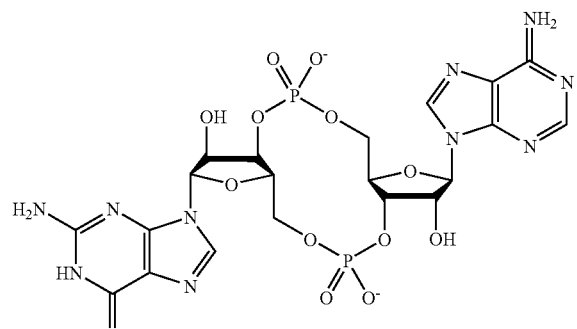
c-GpAp
(VIII)
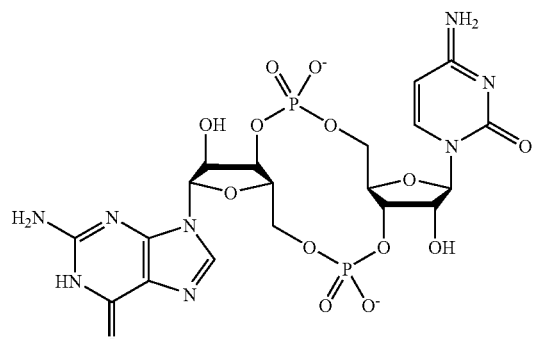
c-GpCp
(IX)
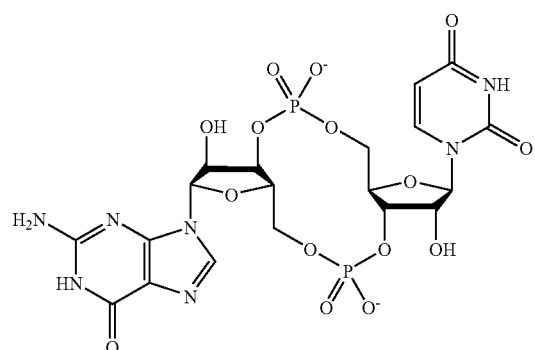
c-GpUp
(X)
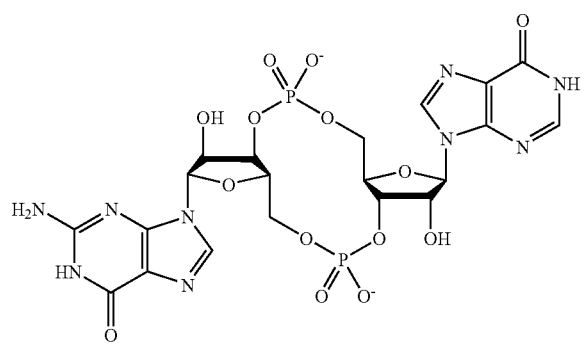
c-GpIp
(XI)
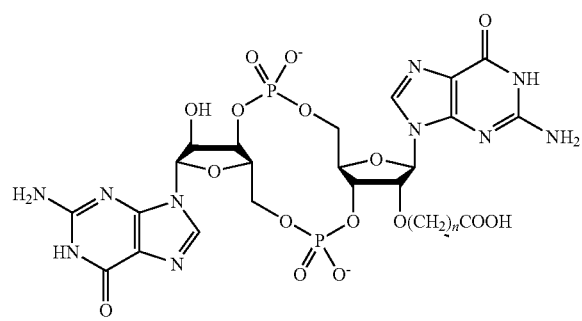
(XII)
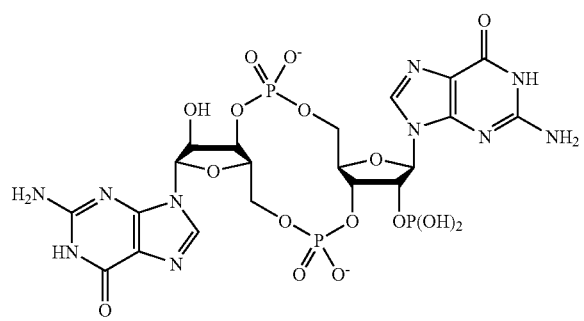
(XIII)
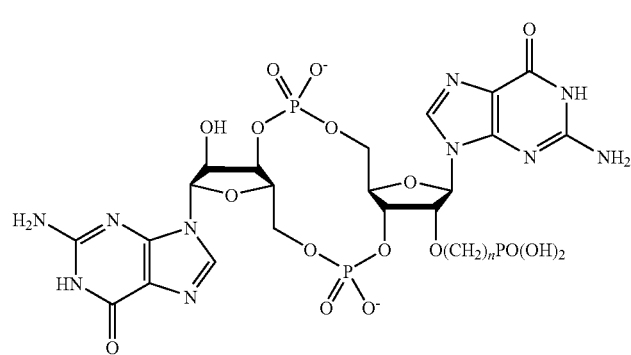

-continued
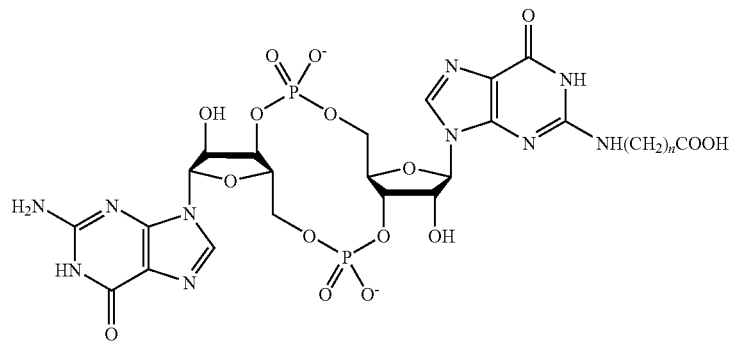
(XIV)
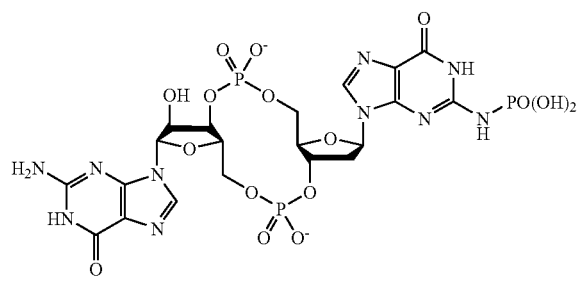
(XV)
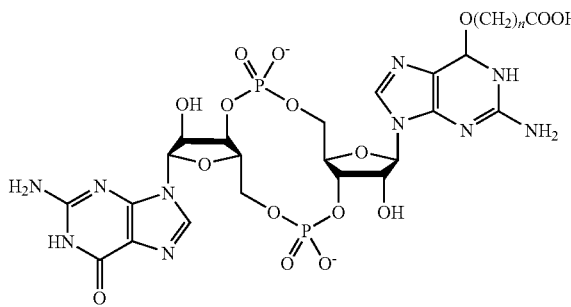
(XVI)
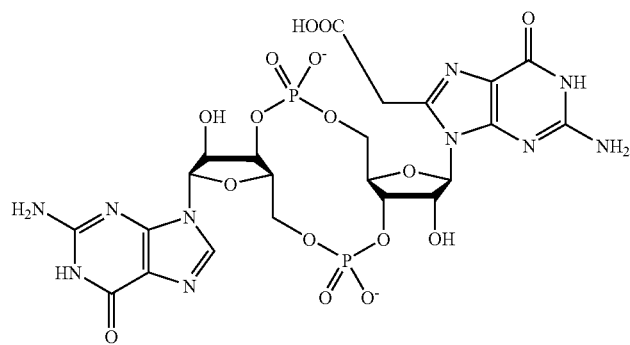
(XVII)
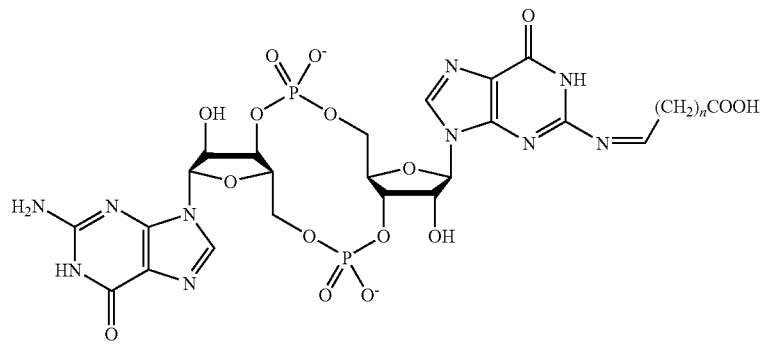
(XVIII)

-continued
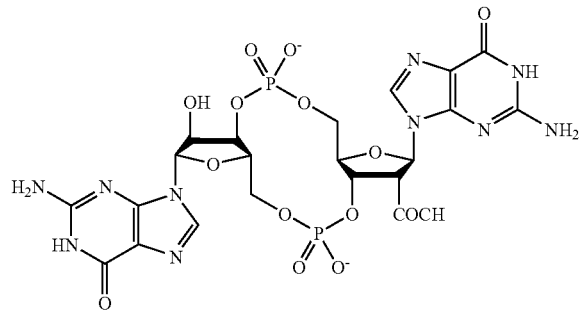
(XIX)
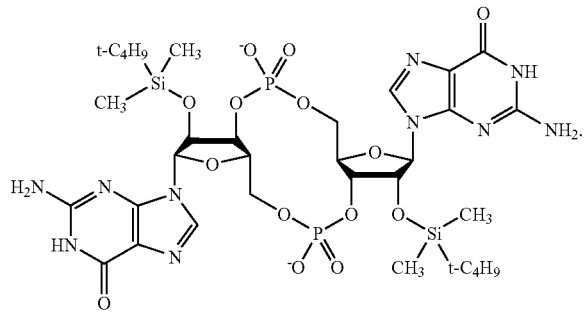
(XX)
2'-O-TBDMS-c-di-GMP
29. The method of claim 1, wherein said cyclic dinucleotide analogue is selected from the group consisting of cyclic dinucleotide compounds (I)-(XX)
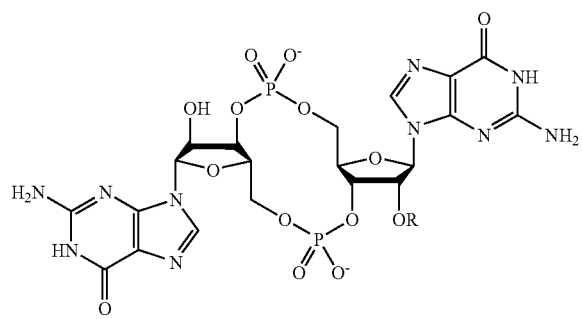
(III)
c-G(2'-OR)pGp
R = CH₃, C₂H₅, etc
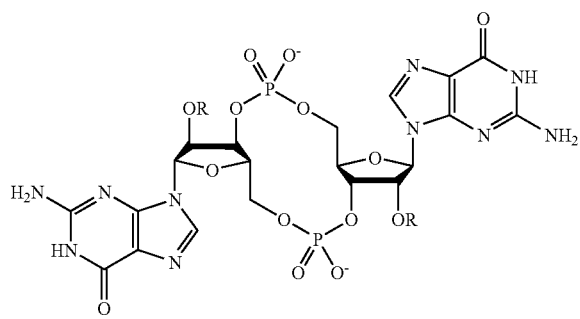
(IV)
c-G(2'-OR)pG(2'-OR)p
R = CH₃, C₂H₅, etc
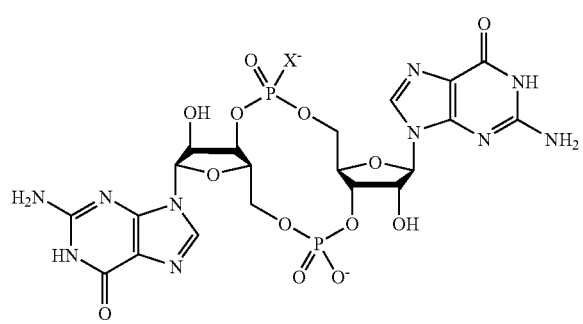
(V)
c-GpXGp
X = S, Se, BH₃
sterochemically pure
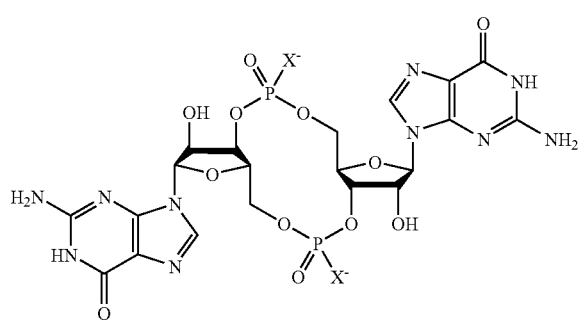
(VI)
c-GpXGpX
X = S, Se
sterochemically pure -continued
(VII)
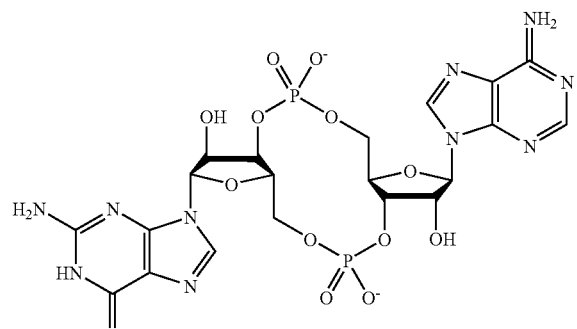
c-GpAp
(VIII)
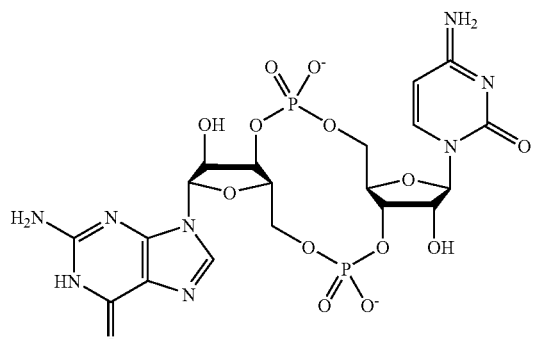
c-GpCp
(IX)
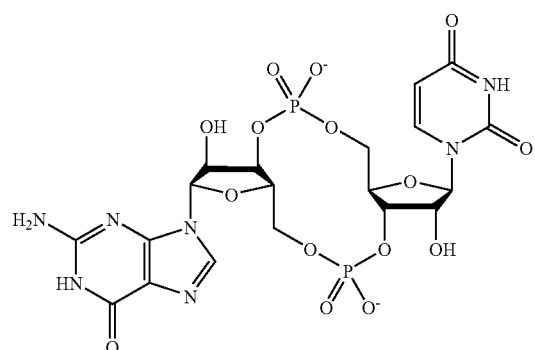
c-GpUp
(X)
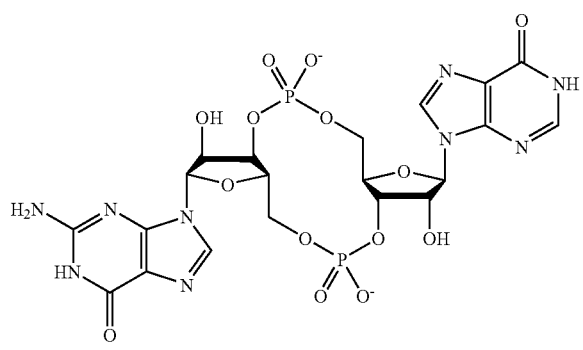
c-GpIp
(XI)
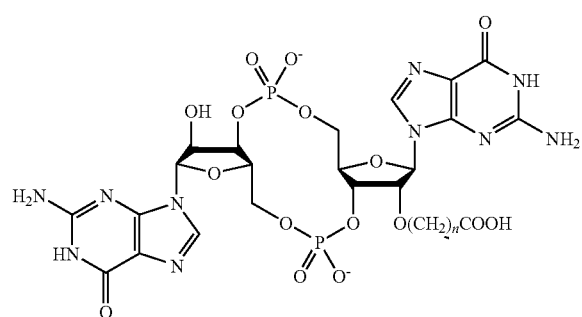
(XII)
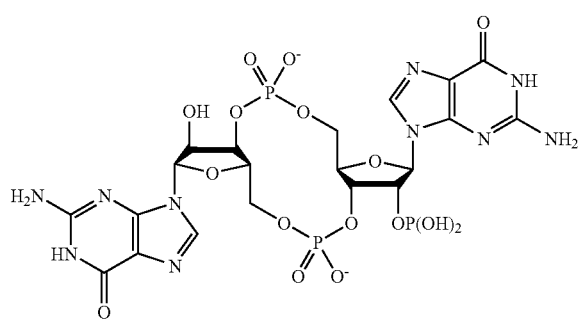
(XIII)
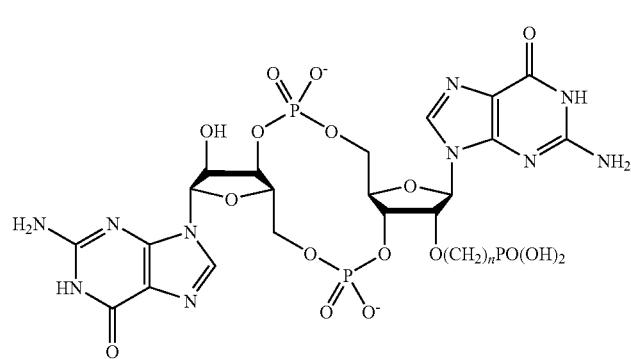

-continued
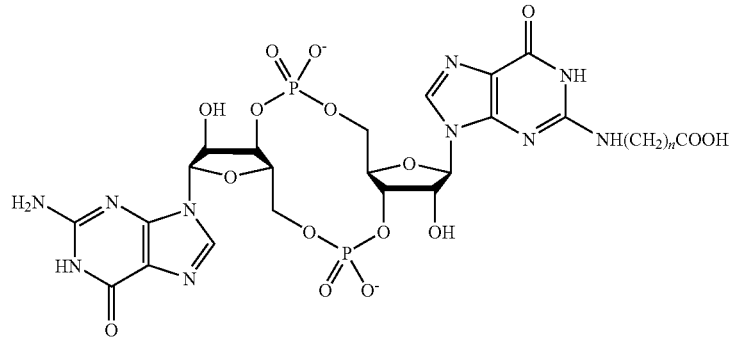
(XIV)
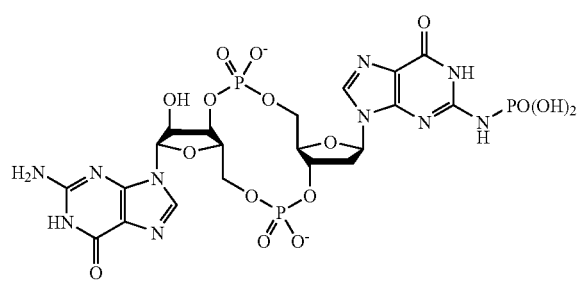
(XV)
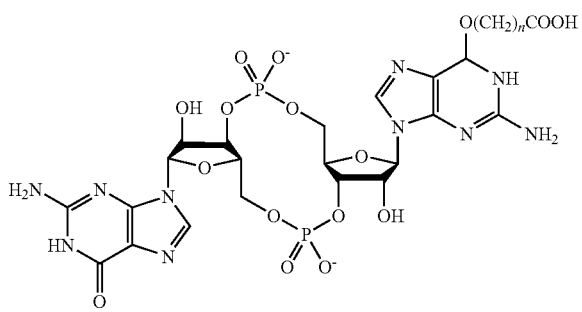
(XVI)
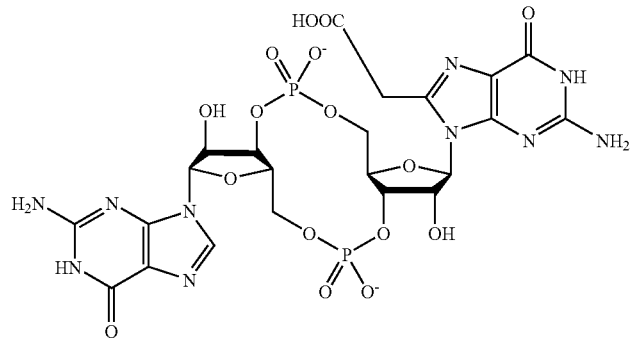
(XVII)
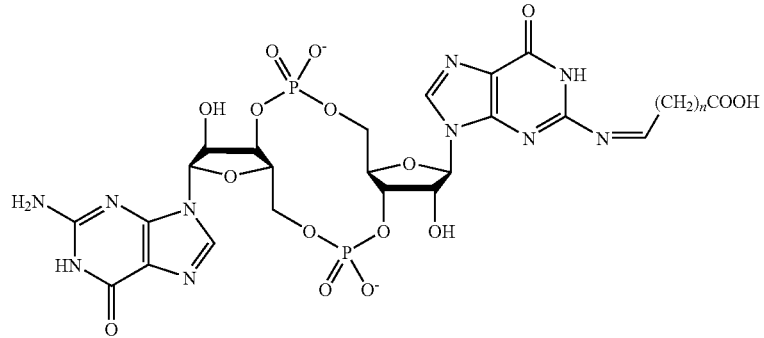
(XVIII)

-continued
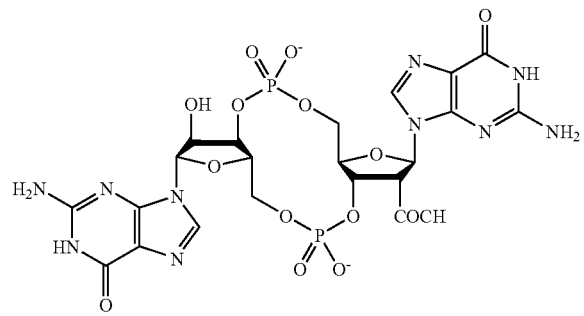
(XIX)
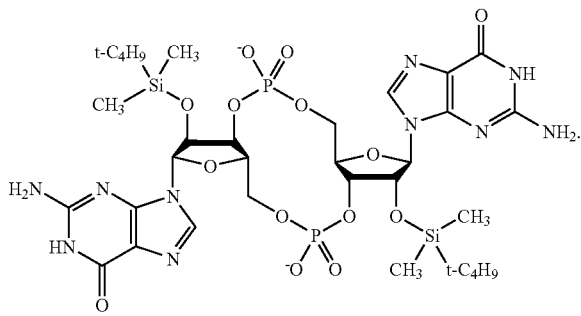
(XX)
2′-O-TBDMS-c-di-GMP
* * * * *